US008101782B2

(12) United States Patent
Rupniak et al.

(10) Patent No.: US 8,101,782 B2
(45) Date of Patent: Jan. 24, 2012

(54) COMPOUNDS THAT INHIBIT CHOLINESTERASE

(75) Inventors: Nadia M. J. Rupniak, Cary, NC (US); James F. White, Carlisle, MA (US); Kazumi Shiosaki, Wellesley, MA (US); J. David Leander, Indianapolis, IN (US); Shoucheng Du, Pittsburgh, PA (US); Daniel J. Coughlin, Hackettstown, NJ (US)

(73) Assignee: Colucid Pharmaceuticals, Inc., Durham, NC (US)

( * ) Notice: Subject to any disclaimer, the term of this patent is extended or adjusted under 35 U.S.C. 154(b) by 928 days.

(21) Appl. No.: 12/012,636

(22) Filed: Feb. 4, 2008

(65) Prior Publication Data

US 2008/0261950 A1 Oct. 23, 2008

Related U.S. Application Data

(60) Provisional application No. 60/899,111, filed on Feb. 2, 2007, provisional application No. 60/959,901, filed on Jul. 16, 2007.

(51) Int. Cl.
*C07D 333/22* (2006.01)
*C07D 267/16* (2006.01)
(52) U.S. Cl. ........................................ 549/22; 540/551
(58) Field of Classification Search .................... 549/77; 540/551
See application file for complete search history.

(56) References Cited

U.S. PATENT DOCUMENTS

| | | | |
|---|---|---|---|
| 3,600,427 A | 8/1971 | Verbiscar | |
| 4,791,107 A | 12/1988 | Hamer et al. | |
| 4,948,807 A | 8/1990 | Rosin et al. | |
| 5,187,165 A | 2/1993 | Hamer et al. | |
| 5,302,721 A | 4/1994 | Wong et al. | |
| 5,409,948 A | 4/1995 | Greig et al. | |
| 5,455,354 A | 10/1995 | Wong et al. | |
| 5,538,968 A | 7/1996 | Chiesi et al. | |
| 5,602,176 A | 2/1997 | Enz | |
| 5,665,880 A | 9/1997 | Lee et al. | |
| 5,677,457 A | 10/1997 | Lee et al. | |
| 2004/0192732 A1 | 9/2004 | Pratt et al. | |
| 2005/0038013 A1 | 2/2005 | Gold | |
| 2005/0096387 A1 | 5/2005 | Verheijen et al. | 514/478 |
| 2007/0275959 A1 | 11/2007 | Verheijen et al. | |

FOREIGN PATENT DOCUMENTS

| | | |
|---|---|---|
| AU | 2002226687 B2 | 8/2005 |
| DE | 3805744 A1 | 9/1988 |
| EP | 0 193 926 A2 | 9/1986 |
| EP | 0 513 703 A2 | 11/1992 |
| FR | 2719047 A1 | 10/1995 |
| JP | 3002155 A | 1/1991 |
| WO | WO 9602524 A1 | 2/1996 |
| WO | WO 97/14694 | 4/1997 |
| WO | WO 97/22339 | 6/1997 |
| WO | WO 97/23484 | 7/1997 |
| WO | WO 00/25821 | 5/2000 |
| WO | WO 02/59074 | 1/2002 |
| WO | WO 2004/034963 A2 | 4/2004 |
| WO | WO 2005/042475 A2 | 5/2005 |
| WO | WO-2008137923 A2 | 11/2008 |
| WO | WO-2009011901 A2 | 1/2009 |
| WO | WO-2010009316 A1 | 1/2010 |

OTHER PUBLICATIONS

Tumiatti et al. (J. Bioorg. Med. Chem., 8 (2000), 681-89).*
Rampa et al. (J. Med. Chem., 2001, 44, p. 3810-20).*
Kubinyi (3D QSAR in Drug Design: Ligand-Protein Interactions and Molecular Similarity, vol. 2-3, Springer, 1998, 800 pages) TOC and pp. 243-244 provided.*
Wermuth, The Practice of Medicinal Chemsitry, 2d ed. (2003), 768 pages; chapters 9-10 provided.*
Tumiatti et al., "[4[[N-(3-Chlorophenyl)carbamoyl]oxy]-2-butynyl]trimethylammonium (McN-A-343)-Related Compounds. Effect of the Butynyl Chain Inclusion into an Aromatic Unit on the Potency for Muscarinic Receptors", *Bioorg. Med. Chem.*, 8(4):681-689 (2000).
Weinstock et al., "Pharmacological activity of novel anticholinesterase agents of potential use in the treatment of Alzheimer's disease", *Advances Behavioral Biol.*, 29:539-549 (1986).
Amstutz et al., "Cyclische Phenyl-carbamate des Miotin-Typs und ihre Wirkung auf die Acetylcholinesterase", *Helvetica Chimica Acta*, 73:739-753 (1990) (English Abstract Only).
Brossi et al., "Invited Review. Phenserine, a Novel Anticholinesterase Related to Physostigmine: Total Synthesis and Biological Properties", *Aust. J. Chem.*, 49:171-181 (1996).
Cutler et al., "Muscarinic $M_1$-Receptor Agonists: Potential in the Treatment of Alzheimer's Disease", *CNS Drugs*, 3(6):467-481 (1995).
Database Beilstein, Beilstein Institut Fuer Chemische Wissenschaften, Frankfurt Am Main, DE, XP002331880. Database CA [Online] Chemical Abstracts Service, Columbus, Ohio, Koyama et al., "Pharmaceuticals Containing (hydroxybenzyl) Amines as Acetylcholine Esterase Inhibitors and Selective Serotonin Reuptake Inhibitors", XP002331878 Retrieved from STN Database Accession No. 2004:291183 Abstract & JP 2004 107322 A2 (BTG International Ltd., UK) Apr. 8, 2004.
Database CA [Online] Chemical Abstracts Service, Columbus, Ohio, Goto et al., "Preparation of Aromatic Carbamates as Choline Esterase Inhibitors for Improvement of Cerebral Function", XP002331879 Retrieved from STN Database Accession No. 1991:206818 Abstract & JP 03 002155 A2 (Takeda Chemical Industries, Ltd., Japan) Jan. 8, 1991.
De Sarno et al., "The Effect of Heptyl-Physostigmine, a New Cholinesterase Inhibitor, on the Central Cholinergic System of the Rat", *Neurochem. Res.*, 14(10):971-977 (1989).
Elmalem et al., "Antagonism of Morphine-Induced Respiratory Depression by Novel Anticholinesterase Agents", *Neuropharmacol.*, 30(10):1059-1064 (1991).

(Continued)

*Primary Examiner* — Robert Havlin
(74) *Attorney, Agent, or Firm* — Mintz, Levin, Cohn, Ferris, Glovsky and Popeo, P.C.; Ivor R. Elrifi; Heidi A. Erlacher

(57) ABSTRACT

Compounds that inhibit cholinesterase activity and, upon hydrolysis release a pharmacologically active agent. The compounds of the invention are employed in methods to treat an individual. The pharmacologically active agent obtained by hydrolysis of the compound can treat, for example, a nervous system condition, a cholinergic deficiency and conditions or diseases associated with a deficiency in a pharmacologically active agent, such as acetylcholine.

6 Claims, 1 Drawing Sheet

OTHER PUBLICATIONS

Fogelson et al., "Effects of Rivastigmine on the Quantitative EEG in Demented Parkinsonian Patients", *Acta Neurol. Scand.*, 107(4):252-255 (2003).

Froestl et al., "SGS742: The first $GABA_B$ Receptor Antagonist in Clinical Trials", *Biochem. Pharmacol.*, 68:1479-1487 (2004).

Gatto et al., "TC-1734: An Orally Active Neuronal Nicotinic Acetylcholine Receptor Modulator with Antidepressant, Neuroprotective and Long-Lasting Cognitive Effects", *CNS Drug Reviews*, 10(2):147-166 (2004).

Grace et al., "A Comparison of Sleep Profiles in Patients with Dementia with Lewy Bodies and Alzheimer's Disease", *Int J. Geriatr. Psychiatry*, 15(11):1028-1033 (2000).

Heinonen et al., "Desmethylselegiline, a Metabolite of Selegiline, Is an Irreversible Inhibitor of Monoamine Oxidase Type B in Humans", *J. Clin. Pharmacol.*, 37:602-609 (1997).

Janssen et al., "Does phenylethylamine Act as an Endogenous Amphetamine in Some Patients?", *Int. J. Neuropsychopharmacol.*, 2:229-240 (1999).

Kerr et al., "$GABA_B$ Receptors", *Pharmac. Ther.*, 67(2):187-246 (1995).

Korczyn, A.D., "Muscarinic M1 Agonist in the Treatment of Alzheimer's Disease", *Exp. Opin. Invest. Drugs*, 9(10):2259-2267 (2000).

Kupsch, A., "Rasagiline Teva Pharmaceutical", *Curr. Opin. Investig. Drugs*, 3(5):794-797 (2002).

Land et al., "D-Cycloserine: Effects on Long-Term Retention of a Conditioned Response and on Memory for Contextual Attributes", *Neurobiol. Learning Mem.*, 72(3):158-168 (1999).

Lipiello et al., "RJR-2403 is an Efficacious Agonist for Human $α4β2$ Neuronal Nicotinic Acetylcholine Receptors with Lower Efficacy for Other Human Receptor Subtypes", *Soc. Neurosci.*, 24:88 (Abstract 39.26) (1998).

Obinu et al., "Brain Selective Stimulation of Nicotinic Receptors by RJR 1734 Enhances ACH Transmission From Frontoparietal Cortex and Enhances Memory in Rodents", *Internatl. J. Neuropyschopharamology*, 3(Suppl. 1):S361 (2003) (Abstract Only).

Obinu et al., "Brain Selective Stimulation of Nicotinic Receptors by TC-1734 Enhances Ach Transmission from Frontoparietal Cortex and Enhances Memory in Rodents", *Progress Neuropsychopharmacol. Biol. Psychiatry*, 26:913-918 (2002).

Parsons et al., "Memantine is a Clinically Well Tolerated *N*-Methyl-D-Aspartate (NMDA) Receptor Antagonist—A Review of Preclinical Data", *Neuropharmacol.*, 38(5):735-767 (1999).

Patani et al., "Bioisosterism: A Rational Approach in Drug Design", *Chemical Reviews*, vol. 96, 3147-3176 (1996).

Rampa et al., "Acetylcholinesterase Inhibitors: SAR and Kinetic Studies on $ω$-[*N*-Methyl-*N*-(3-alkylcarbamoyloxyphenyl)methyl]aminoalkoxyaryl Derivatives", *J. Med. Chem.*, 44:3810-3820 (2001).

Schredl et al., "The Effect of Rivastigmine on Sleep in Elderly healthy Subjects", *Experimental Gerontol.*, 35(2):243-249 (2000).

Siatra-Papastaikoudi, T., et al., "Synthesis of Carbamate Esters of Phenethylamines and their Pharmacological Action on the Central Nervous System", *Chimika Chronika*, 10(4), 307-13 (1981).

Sterling et al., "Novel Dual Inhibitors of AChE and MAO Derived from Hydroxy Aminoindan and Phenethylamine as Potential Treatment for Alzheimer's Disease", *J. Med. Chem.*, 45:5260-5279 (2002).

Trabace et al., "CHF2819: Pharmacological Profile of a Novel Acetylcholinesterase Inhibitor", *CNS Drug Reviews*, 8(1):53-69 (1992).

White et al., "On the Physostigmine-Like Action of Certain Synthetic Urethanes," *J. Pharmacol.*, vol. 41, 259-288 (1931).

Yang et al., "β-Phenylethylamine: A Specific Substrate for Type B Monoamine Oxidase of Brain", *J. Pharmacol. Exp. Ther.*, 187(2):365-371 (1973).

Davis et al. "Circadian Cholinergic Rhythyms: Implications cof Cholinesterase Inhibitor Therapy." *Dement. Geriatr. Cogn. Disord.* 21.2(2006):120-129.

Gao et al. "An Efficient O-Dealkylation Procedure for the Synthesis of (3aS,cis)-1,2,3,3a,8,8a-hexahyrdo-1,3a,8-trimethylpyrrolo[2,3-b]indol-5-yl-3,4-dihydro-2(1H)-isoquinolinecarboxylate." *J. Heterocyclic. Chem.* 37(2000):331-333.

Kogen et al. "Design and Synthesis of Dual Inhibitors of Acetylcholinesterase and Serotonin Transporter Targeting Potential Agents for Alzheimer's Diseases." *Org. Lett.* 4.20(2002):3359-3362.

Mustazza et al. "Synthesis and Cholinesterase Activity of Phenylcarbamates Related to Tivastigmine, a Therapeutic Agent for Alzheimer's Disease." *Eur. J. Med. Chem.* 37(2002):91-109.

Schimelpfening, N., About.com:Depression. Top 9 Depression Symptoms, (available online at http://depression.about.com) updated Jun. 11, 2009.

Toda et al. "Design, Synthesis and Structure-Activity Relationships of Dual Inhibitors of Acetylcholinesterase and Serotonin Transporter as Potential Agents for Alzheimer's Disease." *Bioorg. Med. Chem.* 11(2003):1935-1955.

\* cited by examiner

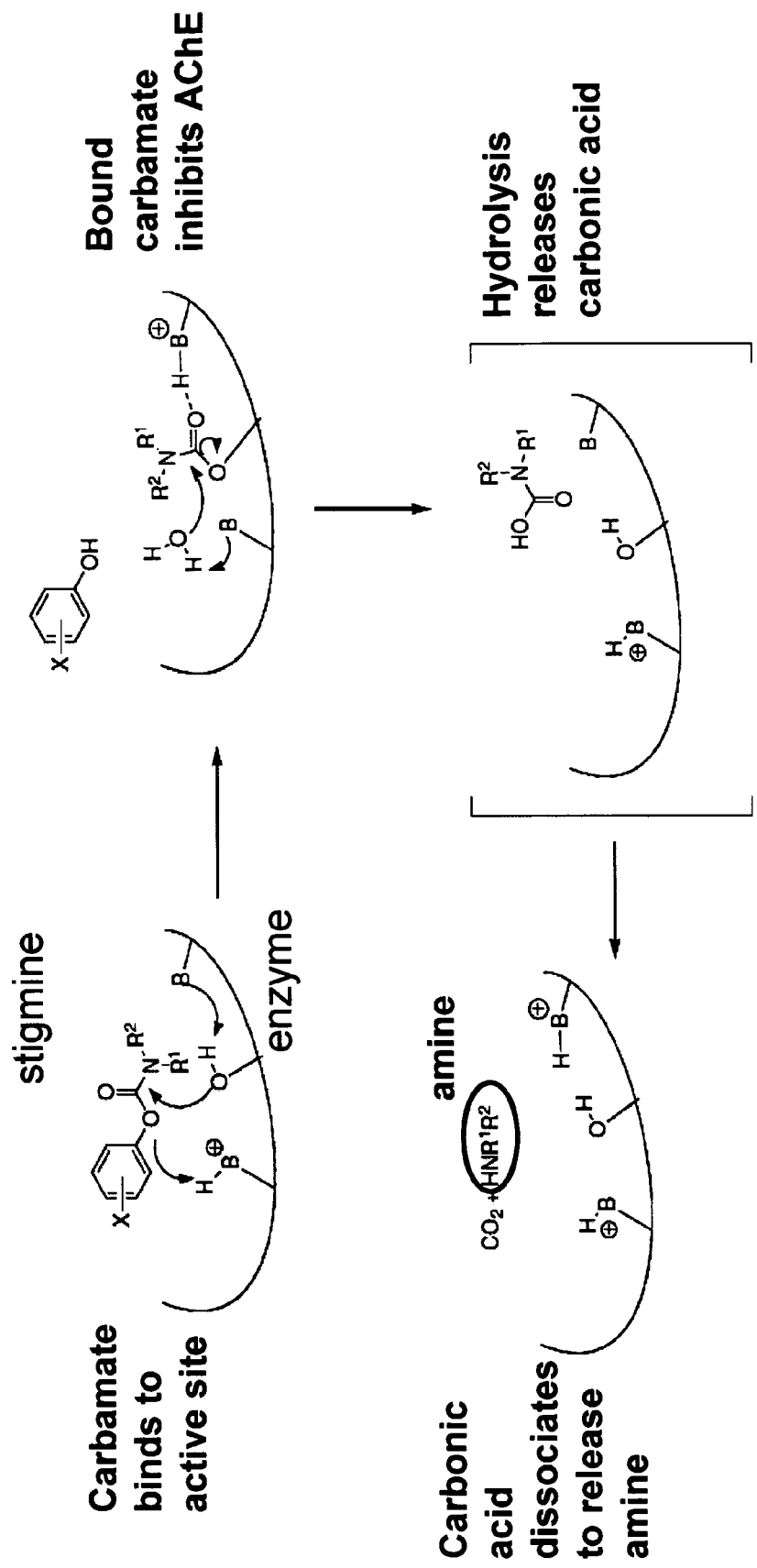

COMPOUNDS THAT INHIBIT CHOLINESTERASE

RELATED APPLICATIONS

This application claims the benefit of and priority to U.S. Patent Application Nos. 60/899,111, filed Feb. 2, 2007 and 60/959,901, filed Jul. 16, 2007, the disclosures of which are incorporated by reference herein.

BACKGROUND OF THE INVENTION

A number of conditions and diseases in humans are accompanied by, or are a consequence of disruptions in cell signal molecules. For example, there can be inadequate synthesis, release or re-uptake of the cell signal molecule(s), or disruptions in mediating cellular signaling of the molecule(s) by receptor or non-receptor mechanisms that result in a disease or other condition. In many instances, clinical management strategies and currently available drugs are frequently associated with adverse side effects and must be meticulously monitored in patients. Current strategies to develop drugs to treat conditions and diseases that are accompanied by or are a consequence of disruptions in cell signal molecules require significant structure-activity modification of a compound. In addition, currently available drugs generally do not target the drug to particular cells or tissues and fail to result in delivery of a drug with a long-lasting effect. In many instances, correction of disruptions in a single cell signal molecule does not effectively treat symptoms of the disease or condition. Thus, there is a need to develop new, improved and effective methods of treatment for diseases or conditions that are associated with or are accompanied by disruptions in cell signal molecules.

SUMMARY OF THE INVENTION

Stigmines are carbamate-based acetylcholinesterase inhibitors. Acetylcholinesterase inhibitors enhance cognitive function by enhancing cholinergic function in the brain and, for example, are approved for therapy of Alzheimer's disease. Alzheimer's patients often exhibit other symptoms including depression, anxiety and sleep disorders, all of which may benefit from treatment with acetylcholinesterase inhibitors, such as rivastigmine and physostigmine.

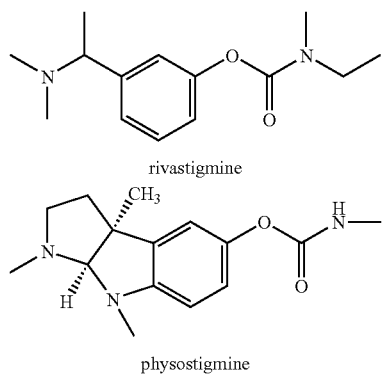

rivastigmine physostigmine

In animal models, acetylcholinesterase inhibitors also exhibit analgesic efficacy. Compounds which are hybrids of rivastigmine or physostigmine and the following classes of drugs may therefore provide additive or synergistic therapeutic benefit, for example, for patients with Alzheimer's disease, Parkinson's disease, glaucoma, oncologic condition(s), or delayed gastric emptying, or patients suffering from attention deficit hyperactivity disorder (ADHD), phobia, stroke, multiple sclerosis, sleep disorders, psychiatric disorders, pain, anticholinergic drug overdose, or tobacco dependence i.e., use of the compounds in patients attempting smoking cessation.

The present invention is directed to compounds that have cholinesterase inhibitory activity. The invention is also directed to methods of using the compounds and to pharmaceutical compositions of the compounds.

In one aspect, the invention includes a compound according to formula I or II:

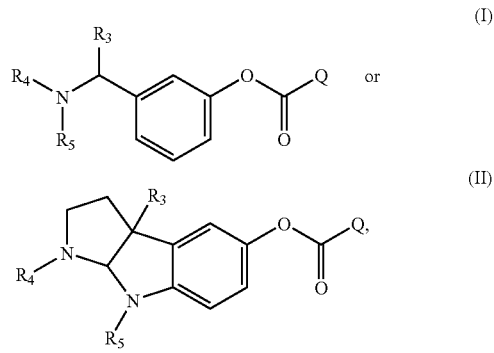

or pharmaceutically acceptable salt wherein Q is selected from a formula in Table 1; $R_1$ is selected from hydrogen, unsubstituted alkyl, substituted alkyl, unsubstituted aralkyl, substituted aralkyl, unsubstituted heteroalkyl, and substituted heteroalkyl or $R_1$ is absent; $R_3$, $R_4$ and $R_5$ are each, independently selected from unsubstituted alkyl and hydrogen.

In one embodiment, the invention is a compound according to formula I. In another embodiment, the invention is a compound according to formula II.

In one embodiment, the invention is a compound according to formula I or II, wherein at least one of $R_3$, $R_4$, and $R_5$ is unsubstituted alkyl. In another embodiment, the invention is a compound, wherein at least two of $R_3$, $R_4$, and $R_5$ is unsubstituted alkyl. In another embodiment, the invention is a compound, wherein $R_3$, $R_4$, and $R_5$ are unsubstituted alkyl. In one embodiment, the invention is a compound as described above, wherein unsubstituted alkyl is methyl.

In one embodiment, the invention is a compound, wherein $R_1$ is absent. In one embodiment, $R_1$ is selected from hydrogen, substituted and unsubstituted alkyl. In another embodiment, $R_1$ is selected from hydrogen and unsubstituted alkyl. In one embodiment, $R_1$ is selected from methyl, hydrogen, ethyl, butyl, isopropyl, propyl, and t-butyl. In another embodiment, $R_1$ is hydrogen. In another embodiment, $R_1$ is unsubstituted alkyl. In one embodiment, $R_1$ is branched alkyl. In one embodiment, $R_1$ is straight chain alkyl. In another embodiment, $R_1$ is selected from isopropyl and t-butyl. In one embodiment, $R_1$ is selected from methyl, ethyl, propyl, and butyl. In one embodiment, $R_1$ is methyl. In one embodiment, $R_1$ is hydrogen or methyl.

In one embodiment, the invention is a compound, wherein Q is selected from P, S, R, Z, Y, SS, JJJ, YY, EEE, UU, AA, FFF, CCC, U, T, X, V, Q', BB, CC, DD, SSS, TTT, MM, and XX. In another embodiment, Q is selected from X, V, P, Q', U, R, S, Y, T, Z, AA, BB, CC, DD, SSS, TTT, MM, UU, and XX. In one embodiment Q is not R, NNN, QQQ, 2L, 2M, and 2PP.

In another embodiment, Q is not EE. In another embodiment, Q is not an amphetamine compound.

In one embodiment, the invention is a compound selected from compounds 2, 3, 4, 5, 6, 7, 8, 9, 10, 11, 12, 13, 14, 15, 16, 17, 18, 19, 20, 21, 22, 23, 24, 25, 26, 27, 28, 29, 30, and 31. In another embodiment, the compound selected from compounds 2, 3, 4, 5, 6, 7, 8, 9, 10, 11, 12, 13, 14, 15, 16, 17, 18, 19, and 20.

In one embodiment, the invention is a pharmaceutical composition comprising a compound of the invention or a pharmaceutically acceptable salt thereof. In another embodiment, the invention is a pharmaceutical composition comprising a compound of the invention or a pharmaceutically acceptable salt thereof and an excipient.

In one embodiment, the invention includes a method of treating an individual having a condition associated with acetylcholinesterase activity, by administering to the individual a compound of the invention, wherein said compound inhibits acetylcholinesterase. The invention includes use of a compound of the invention in the manufacture of a medicament for treatment of a condition associated with acetylcholinesterase activity in an individual, wherein said compound inhibits acetylcholinesterase. In one embodiment, the invention includes a method of treating an individual having a condition associated with acetylcholinesterase activity, by administering to the individual a compound of the invention, wherein the condition is selected from a central nervous system condition, a peripheral nervous system condition and an autonomic nervous system condition. The invention includes use of a compound of the invention, in the manufacture of a medicament for treatment of a condition associated with acetylcholinesterase activity, in an individual selected from a central nervous system condition, a peripheral nervous system condition and an autonomic nervous system condition. In one embodiment, the central nervous system condition is selected from the group consisting of Parkinson's disease, a memory impairment and a cognitive impairment. In another embodiment, the memory impairment is in a human associated with a condition selected from Alzheimer's disease, age-associated memory loss, an impairment in memory consolidation, an impairment in short term memory, mild cognitive impairment and multiple sclerosis.

In one embodiment, the invention includes a method of increasing acetylcholine in an individual by administering to the individual a compound of the invention, wherein the compound inhibits a cholinesterase, thereby increasing acetylcholine. The invention includes the manufacture of a medicament for increasing acetylcholine in an individual, wherein the compound inhibits a cholinesterase, thereby increasing acetylcholine.

In one embodiment, the invention includes a method of treating a cholinergic deficiency in an individual by administering to the individual a compound of the invention, wherein the compound inhibits a cholinesterase thereby treating the cholinergic deficiency in the individual. The invention includes use of a compound of the invention in the manufacture of a medicament for treating a cholinergic deficiency in an individual, wherein the compound inhibits a cholinesterase thereby treating the cholinergic deficiency in the individual. In one embodiment, the cholinergic deficiency is Alzheimer's disease. In another embodiment, the cholinergic deficiency is Alzheimer's disease.

In one embodiment, the invention includes a method of treating an impairment in memory in an individual by administering to the individual a compound of the invention, wherein the compound inhibits a cholinesterase thereby treating the impairment in memory in the individual. The invention includes use of a compound of the invention in the manufacture of a medicament for treating an impairment in memory in an individual, wherein the compound inhibits a cholinesterase thereby treating the impairment in memory in the individual. In one embodiment, the invention includes the impairment in memory in the individual is selected from an impairment in memory consolidation, an impairment in long-term memory and an impairment in short-term memory. In another embodiment, the impairment in memory is associated with a condition selected from Alzheimer's disease, age-associated memory loss, mild cognitive impairment and multiple sclerosis.

In one embodiment, the invention includes a method of treating a condition associated with acetylcholinesterase activity, of an individual by administering a compound of the invention, wherein the condition is a nervous system condition selected from delayed gastric emptying, attention deficit hyperactivity disorder (ADHD), phobia, sleep disorder, stroke, psychiatric disorder, pain, anticholinergic drug overdose, tobacco dependence, Parkinson's disease, memory impairment, and cognitive impairment. The invention includes use of a compound of the invention in the manufacture of a medicament for treating a condition associated with acetylcholinesterase activity of an individual, wherein the condition is a nervous system condition selected from delayed gastric emptying, attention deficit hyperactivity disorder (ADHD), phobia, sleep disorder, stroke, psychiatric disorder, pain, anticholinergic drug overdose, tobacco dependence, Parkinson's disease, memory impairment, and cognitive impairment.

In one embodiment, the invention includes a method of treating a condition associated with acetylcholinesterase activity in an individual by administering a compound of the invention, wherein the condition is selected from glaucoma, oncologic condition, delayed gastric emptying, attention deficit hyperactivity disorder (ADHD), phobia, stroke, multiple sclerosis, sleep disorder, psychiatric disorder, pain, anticholinergic drug overdose, tobacco dependence, cardiovascular condition e.g., hypertension, bacterial infection, Meniere's disease, viral infection, allergies, and spasticity. The invention includes use of a compound of the invention in the manufacture of a medicament for treating a condition associated with acetylcholinesterase activity in an individual, wherein the condition is selected from glaucoma, oncologic condition, delayed gastric emptying, attention deficit hyperactivity disorder (ADHD), phobia, stroke, multiple sclerosis, sleep disorder, psychiatric disorder, pain, anticholinergic drug overdose, tobacco dependence, cardiovascular condition e.g., hypertension, bacterial infection, Meniere's disease, viral infection, allergies, and spasticity.

In one embodiment, the invention includes a method of treating a condition associated with acetylcholinesterase activity of an individual by administering a compound of the invention, wherein the condition is selected from delayed gastric emptying, attention deficit hyperactivity disorder (ADHD), phobia, sleep disorder, stroke, psychiatric disorder, pain, anticholinergic drug overdose, and tobacco dependence. The invention includes use of a compound of the invention in the manufacture of a medicament for treating a condition associated with acetylcholinesterase activity of an individual, wherein the condition is selected from delayed gastric emptying, attention deficit hyperactivity disorder (ADHD), phobia, sleep disorder, stroke, psychiatric disorder, pain, anticholinergic drug overdose, and tobacco dependence.

In one embodiment, the invention includes a method of treating a condition associated with acetylcholinesterase activity of an individual by administering a compound of the invention, wherein the condition is anticholinergic drug overdose. The invention includes use of a compound of the invention in the manufacture of a medicament for treating a condition associated with acetylcholinesterase activity of an individual, wherein the condition is anticholinergic drug overdose.

In one embodiment, the invention includes the methods discussed above, wherein the individual is a human.

The compounds of the invention inhibit cholinesterase activity and upon hydrolysis release a pharmacologically active agent or a component of a pharmacologically active agent. In one embodiment the pharmacologically active agent is Q-H. In another embodiment, the pharmacologically active agent is a salt of Q-H. In one embodiment, the pharmacologically active agent of the invention is a CNS active compound, for example an MAO-B inhibitor, such as compounds that are approved for Parkinson's disease, e.g. a norepinephrine reuptake inhibitor, such as those approved for attention deficit hyperactivity disorder (ADHD) or depression, e.g., atomoxetine, desipramine, nortriptyline, protriptyline, and amoxapine; a selective serotonin reuptake inhibitor (SSRI), such as compounds approved for depression, obsessive compulsive disorder, or anxiety disorders, e.g., fluvoxamine, and paroxetine; and a dual norepinephrine/serotonin reuptake inhibitor, such as those compounds approved for depression, stress urinary incontinence or chronic pain, e.g., duloxetine.

In an additional embodiment, the invention is a method of treating a condition in an individual by administering to the individual a compound of the invention. For example, the condition is a neurological condition.

For example, the condition is an impairment in memory in an individual, depression, Parkinson's disease, dementia, ADHD, OCD, an anxiety disorder, stress urinary incontinence, chronic pain, or narcolepsy.

Compounds which are hybrids of rivastigmine or physostigmine and particular classes of drugs may provide additive or synergistic therapeutic benefit for patients.

Without wishing to be bound by theory, the compounds of the invention are thought to inhibit the activity of a cholinesterase and therefore are useful to treat a variety of conditions, such as neurological conditions, e.g., by treating a cholinergic deficiency and increasing transmission between neurons, by increasing the amount of an amine in a synaptic cleft, by delivering amines into a synaptic cleft or by increasing delivery of pharmacologically active amines into the central nervous system. Other conditions which can be treated by the compounds of the invention include, but are not limited to, cardiovascular conditions or various bacterial infections. Advantages of the invention include, for example, delivering a pharmacologically active agent, such as a modulator of neurotransmission, without significant structural alteration to the pharmacologically active agent, to a synapse, which leads to neurotransmission that may be lacking or diminished, thereby, treating diseases or conditions associated with neurotransmitter imbalances. The methods of the invention can increase the amount of a pharmacologically active agent, such as a neurotransmitter, thereby compensating for a disease or condition associated with deficiency of a neurotransmitter.

Thus, the compounds of the invention can be employed in the treatment of diseases or other conditions associated with pharmacologically active agents and thereby halt, reverse or diminish the progression of the diseases or other conditions, or promote physiological processes that can be treated with pharmacologically active agents, such as pharmacologically active agents that treat conditions associated with synaptic transmission.

BRIEF DESCRIPTION OF THE DRAWINGS

FIG. 1 depicts the mechanism of acetylcholinesterase inhibition by compounds of the invention.

DETAILED DESCRIPTION OF THE INVENTION

The features and other details of the invention, either as steps of the invention or as combinations of parts of the invention, will now be more particularly described and pointed out in the claims. It will be understood that the particular embodiments of the invention are shown by way of illustration and not as limitations of the invention. The principle features of this invention can be employed in various embodiments without departing from the scope of the invention.

In one aspect, the invention includes a compound according to formula I or II:

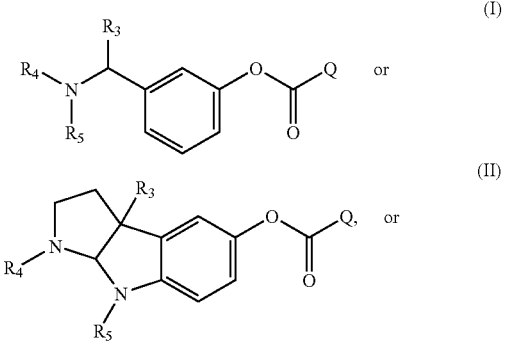

pharmaceutically acceptable salt wherein Q is selected from a formula in Table 1; $R_1$ is selected from hydrogen, unsubstituted alkyl, substituted alkyl, unsubstituted aralkyl, substituted aralkyl, unsubstituted heteroalkyl, and substituted heteroalkyl or $R_1$ is absent; $R_3$, $R_4$ and $R_5$ are each, independently selected from unsubstituted alkyl and hydrogen.

In one embodiment, the invention is a compound according to formula I. In another embodiment, the invention is a compound according to formula II.

In one embodiment, the invention is a compound according to formula I or II, wherein at least one of $R_3$, $R_4$, and $R_5$ is unsubstituted alkyl. In another embodiment, the invention is a compound, wherein at least two of $R_3$, $R_4$, and $R_5$ is unsubstituted alkyl. In another embodiment, the invention is a compound, wherein $R_3$, $R_4$, and $R_5$ are unsubstituted alkyl. In one embodiment, the invention is a compound as described above, wherein unsubstituted alkyl is methyl.

In one embodiment, the invention is a compound, wherein $R_1$ is absent. In one embodiment, $R_1$ is selected from hydrogen, substituted and unsubstituted alkyl. In another embodiment, $R_1$ is selected from hydrogen and unsubstituted alkyl. In one embodiment, $R_1$ is selected from methyl, hydrogen, ethyl, butyl, isopropyl, propyl, and t-butyl. In another embodiment, $R_1$ is hydrogen. In one embodiment, $R_1$ is unsubstituted alkyl. In one embodiment, $R_1$ is branched alkyl. In one embodiment, $R_1$ is straight chain alkyl. In another embodiment, $R_1$ is selected from isopropyl and t-butyl. In one embodiment, $R_1$ is selected from methyl, ethyl, propyl, and butyl. In one embodiment, $R_1$ is methyl. In one embodiment, $R_1$ is hydrogen or methyl.

In one embodiment, the invention is a compound, wherein Q is selected from P, S, R, Z, Y, SS, JJJ, YY, EEE, UU, AA, FFF, CCC, U, T, X, V, P, Q', U, BB, CC, DD, SSS, TTT, MM, UU, and XX. In another embodiment, Q is selected from X, V, P, Q', U, R, S, Y, T, Z, AA, BB, CC, DD, SSS, TTT, MM, UU, and XX.

In another embodiment, the invention is a compound, wherein Q is represented by formula V, Y, AA, DD, FF, HH, II, JJ, OO, PP, VV, WW, XX, ZZ, AAA, BBB, FFF, HHH, III, JJJ, KKK, LLL, MMM, AAAA, CCCC, EEEE, FFFF, HHHH, MMMM, QQQQ, UUUU, WWWW, XXXX, ZZZZ, AAAAA, CCCCC, DDDDD, MMMMM, PPPPP, QQQQQ, RRRRR, VVVVV, WWWWW, XXXXX, YYYYY, 2D, 2E, 2G, 2H, 2I, 2J, 2K, 2M, 2n, 2O, 2P, 2Q, 2R, 2T, 2V, 2W, 2X, 2Y, 2CC, 2DD, 2OO, 2PP, 2RR, 2TT, 2UU, 2VV, 2XX, 2YY, 2AAA, 2CCC, 2HHH, 2SSS, 2TTT, 2ZZZ, 2UUU, 2AAAA, 2GGGG, 2HHHH, 2IIII, 2MMMM, 2NNNN, 2OOOO, 2PPPP, 2QQQQ, 2RRRR, 2TTTT, 2UUUU, 2VVVV, 2AAAAA, 2BBBBB, 2DDDDD, 2EEEEE, 2FFFFF, 2GGGGG, 2HHHHH, 2IIIII, 2JJJJJ, 2NNNNN, 2OOOOO, 2QQQQQ, 2RRRRR, 2TTTTT, 2WWWWW, 2XXXXX, 2ZZZZZ, 3A, 3B, 3E, 3F, 3H, 3I, 3M, 3N, 3O, 3P, 3R, 3S, 3T, 3U, 3V, 3X, 3AA, 3BB, 3DD, 3EE, 3FF, 3GG, 3HH, 3II, 3JJ, 3LL, 3MM, 3OO, 3PP, 3SS, 3TT, 3UU, 3VV, 3WW, 3XX, 3YY, 3ZZ, 3AAA, and 3CCC.

In another embodiment, the invention is a compound, wherein Q is represented by formula S, X, AA, CC, EE, II, KK, LL, MM, NN, OO, PP, QQ, RR, SS, TT, UU, YY, CCC, DDD, EEE, GGG, SSS, TTT, UUU, VVV, WWW, XXX, YYY, ZZZ, BBBB, DDDD, GGGG, JJJJ, IIII, KKKK, LLLL, NNNN, OOOO, PPPP, RRRR, SSSS, TTTT, VVVV, YYYY, BBBBB, EEEEE, FFFFF, GGGGG, HHHHH, IIIII, JJJJJ, KKKKK, LLLLL, NNNNN, OOOOO, SSSSS, TTTTT, UUUUU, ZZZZZ, 2A, 2B, 2C, 2F, 2L, 2R, 2S, 2U, 2W, 2X, 2Z, 2AA, 2BB, 2CC, 2DD, 2EE, 2FF, 2GG, 2HH, 2II, 2JJ, 2KK, 2LL, 2MM, 2NN, 2QQ, 2SS, 2WW, 2YY, 2ZZ, 2AAA, 2BBB, 2DDD, 2EEE, 2FFF, 2GGG, 2HHH, 2III, 2JJJ, 2KKK, 2LLL, 2MMM, 2NNN, 2OOO, 2PPP, 2QQQ, 2RRR, 2VVV, 2WWW, 2XXX, 2YYY, 2AAAA, 2BBBB, 2CCCC, 2DDDD, 2EEEE, 2FFFF, 2IIII, 2JJJJ, 2KKKK, 2LLLL, 2NNNN, 2PPPP, 2SSSS, 2VVVV, 2WWWW, 2XXXX, 2YYYY, 2ZZZZ, 2AAAAA, 2CCCCC, 2KKKKK, 2LLLLL, 2MMMMM, 2PPPPP, 2UUUUU, 2VVVVV, 2YYYYY, 3A, 3C, 3D, 3G, 3J, 3K, 3L, 3M, 3Q, 3W, 3Y, 3Z, 3BB, 3CC, 3KK, 3NN, 3PP, 3QQ, 3RR, 3SS, 3YY, 3BBB, and 3XXX.

In another embodiment, the invention is a compound, wherein Q is represented by formula P, Q', R, T, Z, U, BB, and OOO.

In another embodiment, the invention is a compound, wherein Q is represented by formula GG.

In one embodiment, the invention is a compound selected from compounds 2, 3, 4, 5, 6, 7, 8, 9, 10, 11, 12, 13, 14, 15, 16, 17, 18, 19, 20, 21, 22, 23, 24, 25, 26, 27, 28, 29, 30, and 31. In another embodiment, the compound selected from compounds 2, 3, 4, 5, 6, 7, 8, 9, 10, 11, 12, 13, 14, 15, 16, 17, 18, 19, and 20.

In one embodiment, the invention is a pharmaceutical composition comprising a compound of the invention or a pharmaceutically acceptable salt thereof. In another embodiment, the invention is a pharmaceutical composition comprising a compound of the invention or a pharmaceutically acceptable salt thereof and an excipient. An excipient is an inactive substance used as a carrier for the active ingredient of a compound of the invention. In one embodiment, the compound of the invention may not be easily administered and absorbed by the human body and therefore, is administered in combination with an excipient.

The compounds of the invention inhibit cholinesterase activity and upon hydrolysis release a pharmacologically active agent or a component of a pharmacologically active agent. In one embodiment the pharmacologically active agent or a component of a pharmacologically active agent is Q-H. Formulae for Q are shown below in Table 1. In the formulae for Q in Table 1, the structure

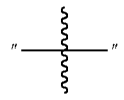

indicates the point of attachment of the structure Q to formula I and formula II. The structure

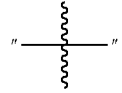

is replaced with H, where the pharmacologically active agent or component of the pharmacologically active agent is Q-H.

TABLE 1

Formula for Q

TABLE 1-continued
Formula for Q
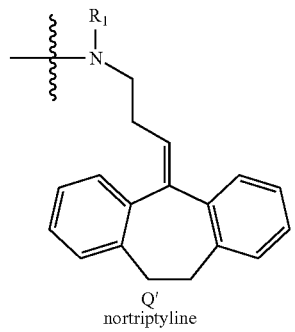
Q'
nortriptyline
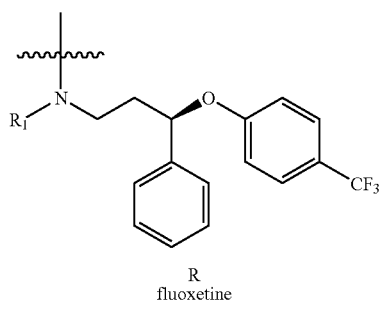
R
fluoxetine
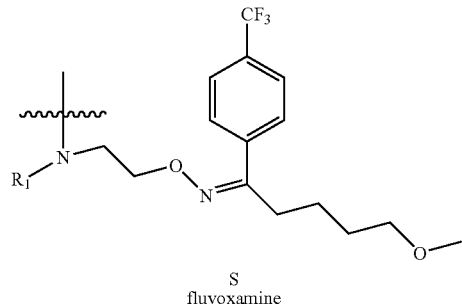
S
fluvoxamine
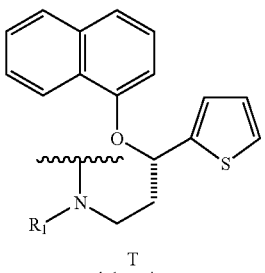
T
duloxetine
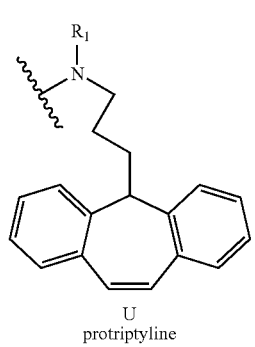
U
protriptyline TABLE 1-continued
Formula for Q
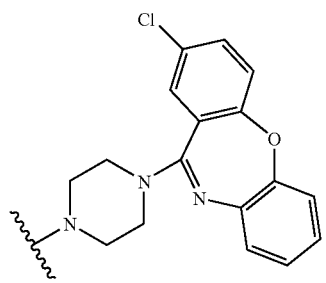
V
amoxapine
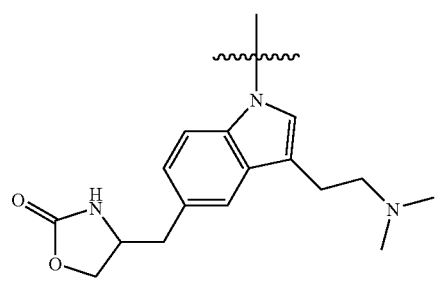
3CCC-2
zolmitriptan
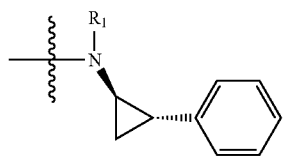
X
tranylcypromine
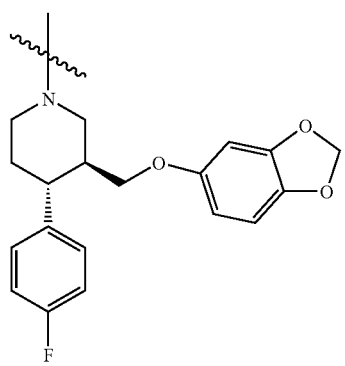
Y
paroxetine
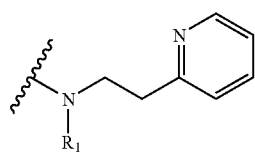
Z
betahistine TABLE 1-continued
Formula for Q
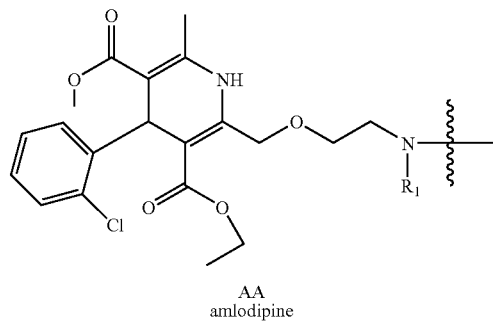
AA
amlodipine
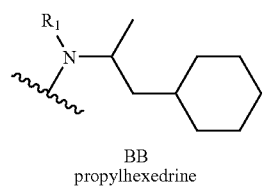
BB
propylhexedrine
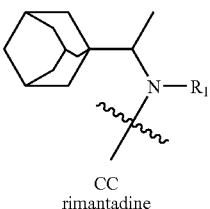
CC
rimantadine
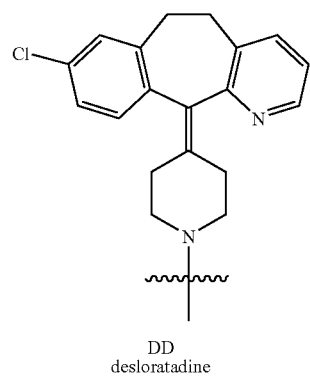
DD
desloratadine
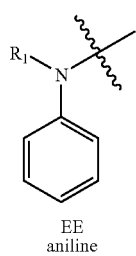
EE
aniline TABLE 1-continued
Formula for Q
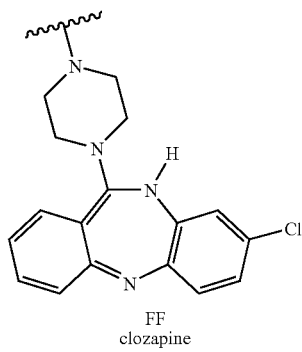
FF
clozapine
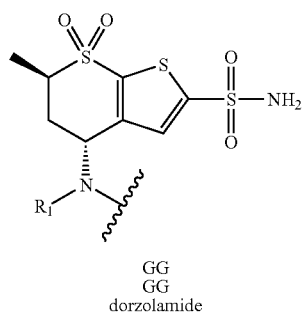
GG
GG
dorzolamide
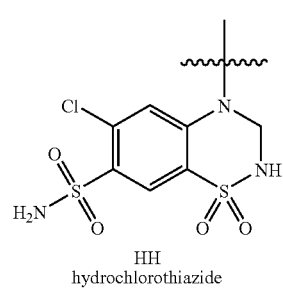
HH
hydrochlorothiazide
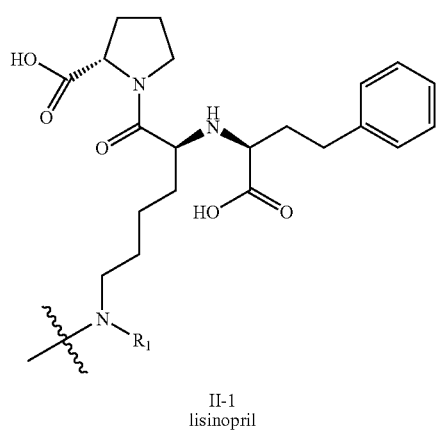
II-1
lisinopril TABLE 1-continued
Formula for Q
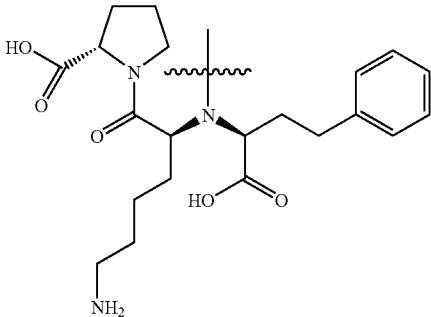
II-2
lisinopril
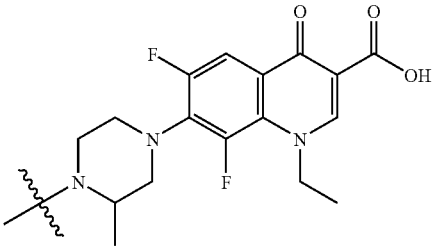
JJ
lomefloxacin
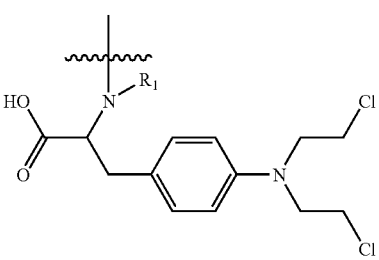
KK
melphalan
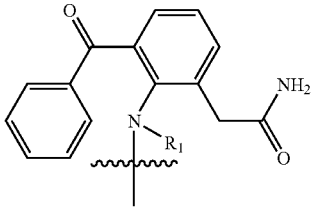
LL
nepafenac
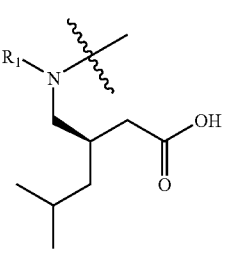
MM
pregabalin TABLE 1-continued
Formula for Q
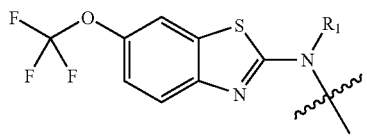
NN
riluzole
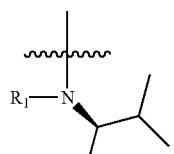
OO-1
valcyclovir
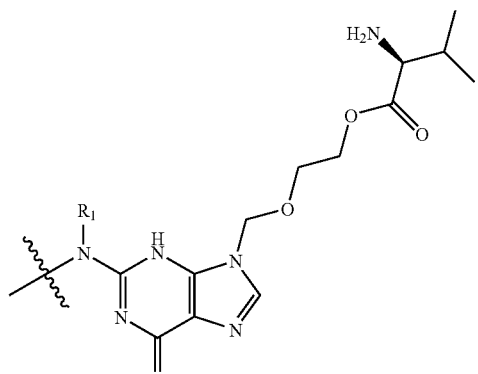
OO-2
valcyclovir
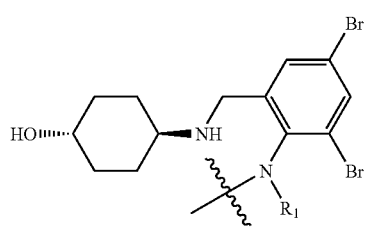
PP-1
ambroxol TABLE 1-continued
Formula for Q
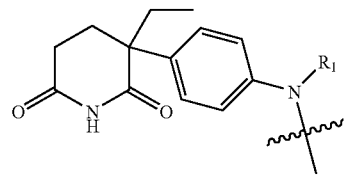
QQ
aminoglutethimide
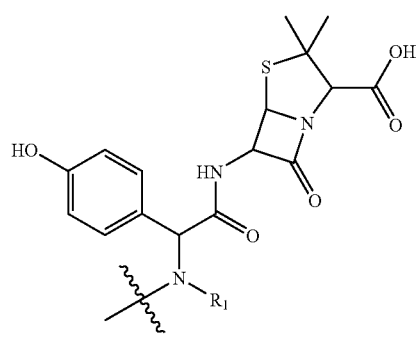
RR
amoxicillin
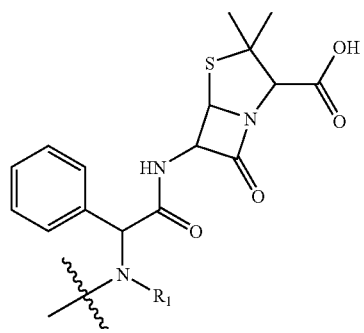
SS
ampicillin
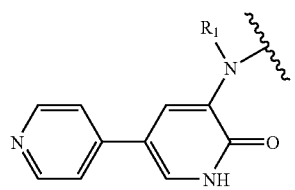
TT
amrinone
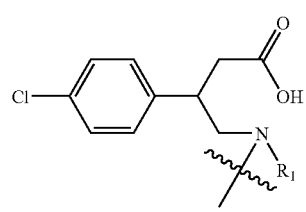
UU
baclofen TABLE 1-continued
Formula for Q
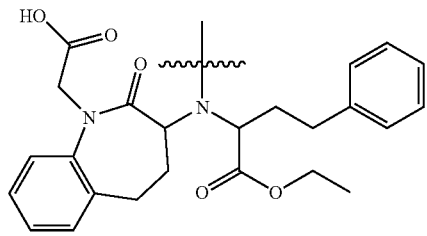
VV
benazepril
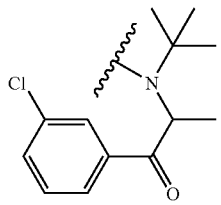
WW
bupropion
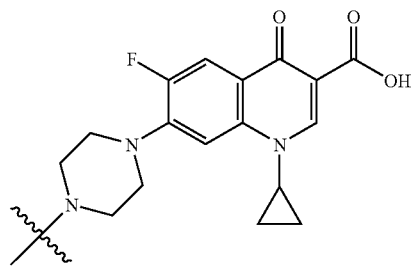
XX
ciprofloxacin
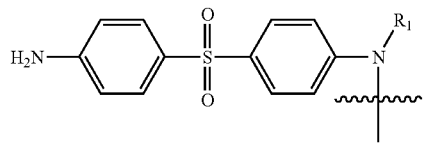
YY
dapsone
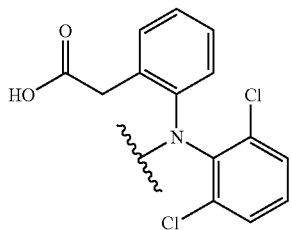
ZZ
diclofenac TABLE 1-continued
Formula for Q
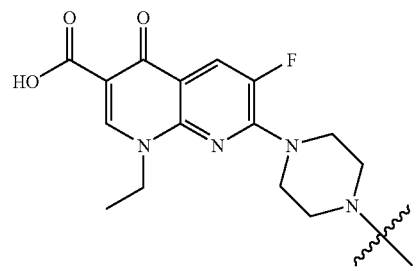
AAA
enoxacin
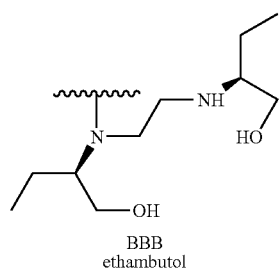
BBB
ethambutol
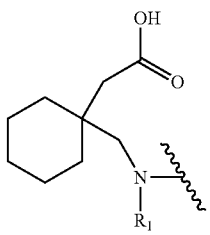
CCC
gabapentin
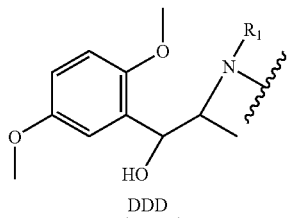
DDD
methoxamine
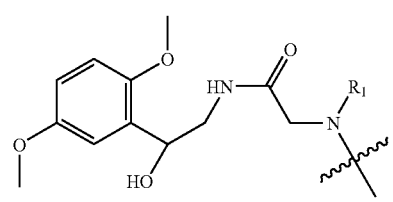
EEE
midodrine TABLE 1-continued
Formula for Q
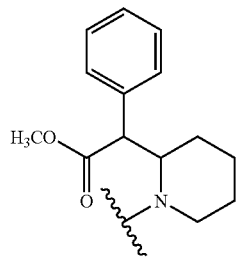
FFF
methylphenidate
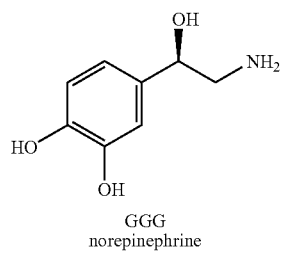
GGG
norepinephrine
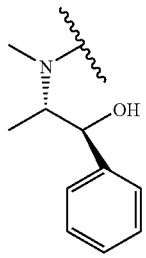
HHH
pseudoephedrine
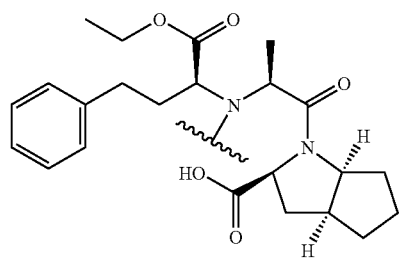
III
rapmipril
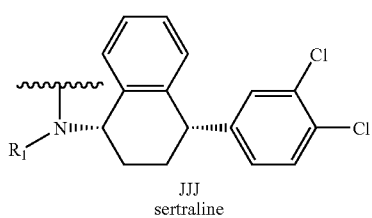
JJJ
sertraline TABLE 1-continued
Formula for Q
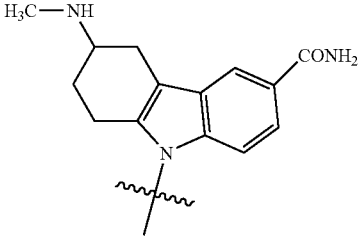
KKK-1
frovatriptan
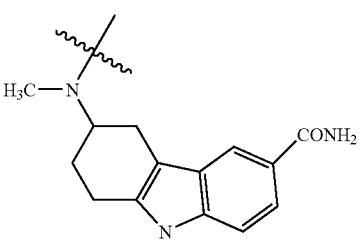
KKK-2
frovatriptan
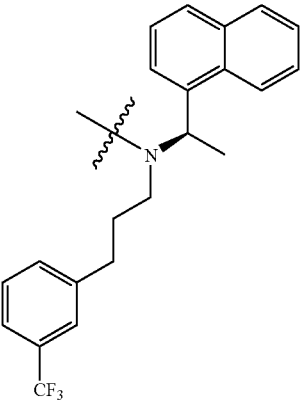
LLL
cinacalcet
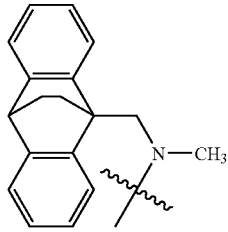
MMM
benzoctamine
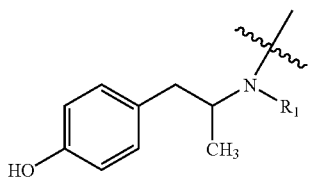
NNN
hydroxyamphetamide TABLE 1-continued
Formula for Q
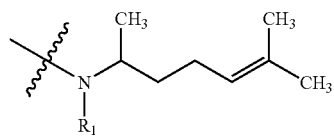
OOO
isometheptene
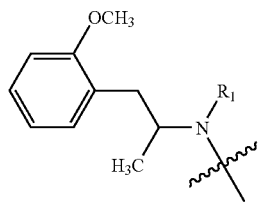
PPP
methoxyphenamine
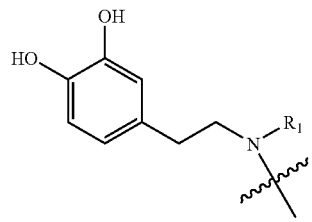
QQQ
dopamine
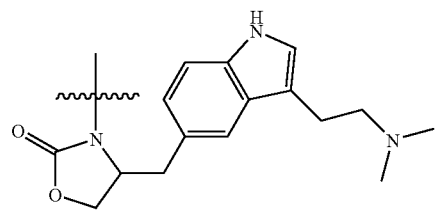
3CCC-1
zolmitriptan
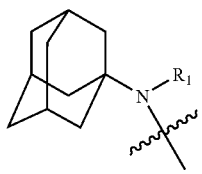
SSS
amantadine
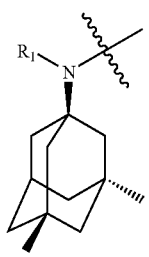
TTT
memantine TABLE 1-continued
Formula for Q
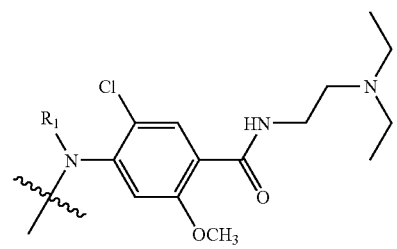
UUU
metoclopramide
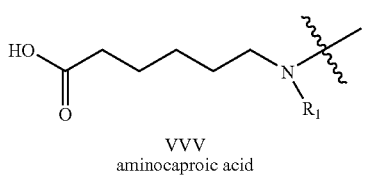
VVV
aminocaproic acid
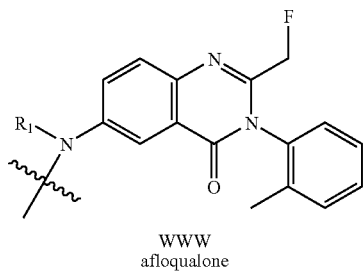
WWW
afloqualone
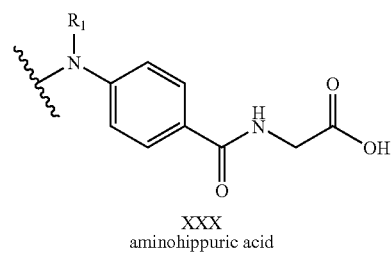
XXX
aminohippuric acid
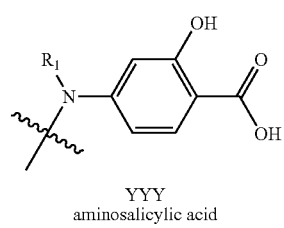
YYY
aminosalicylic acid
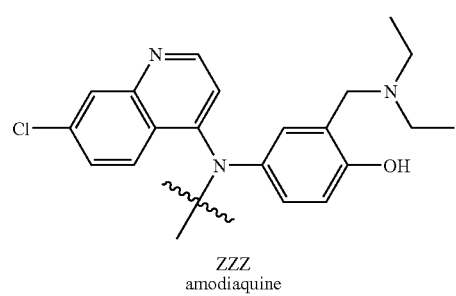
ZZZ
amodiaquine TABLE 1-continued
Formula for Q
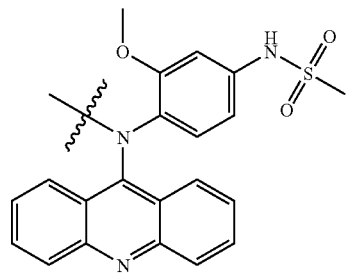
AAAA
amsacrine
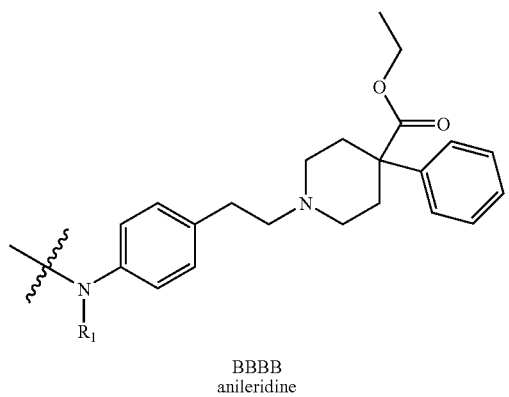
BBBB
anileridine
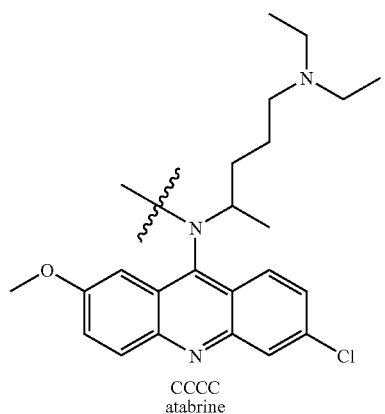
CCCC
atabrine
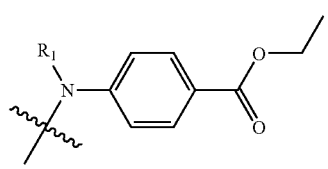
DDDD
benzocaine

TABLE 1-continued
Formula for Q
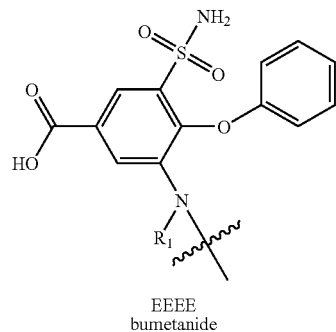
EEEE
bumetanide
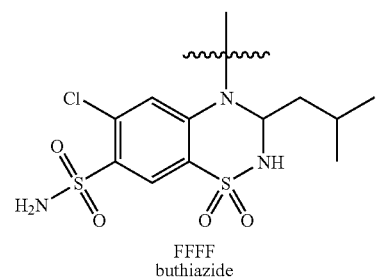
FFFF
buthiazide
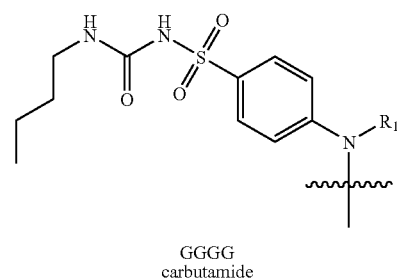
GGGG
carbutamide
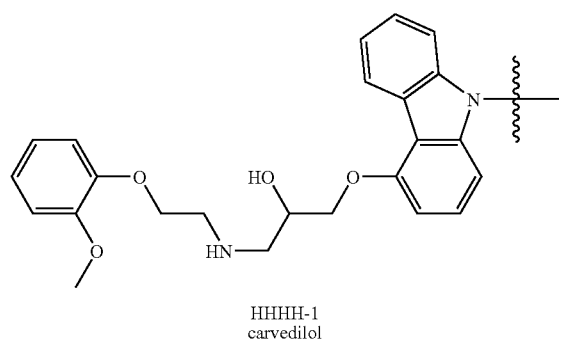
HHHH-1
carvedilol TABLE 1-continued
Formula for Q
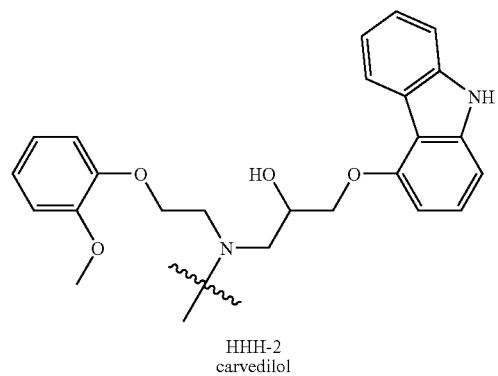
HHH-2
carvedilol
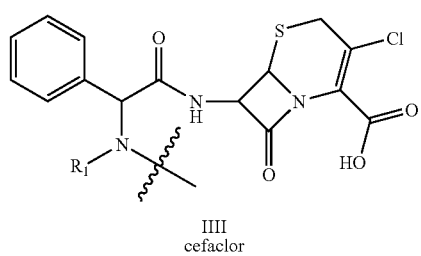
IIII
cefaclor
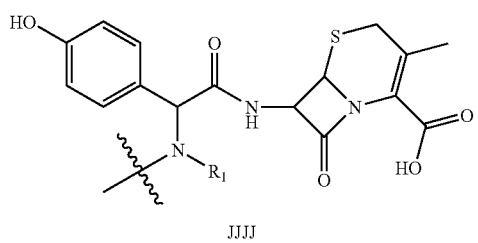
JJJJ
cefadroxil
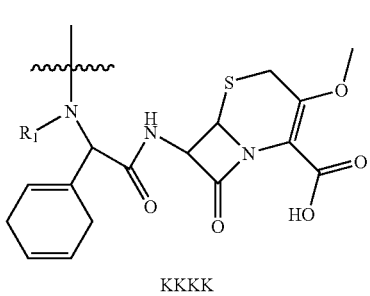
KKKK
cefroxadine
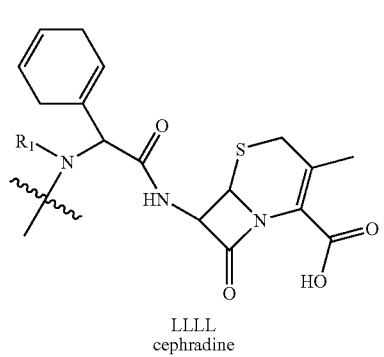
LLLL
cephradine TABLE 1-continued
Formula for Q
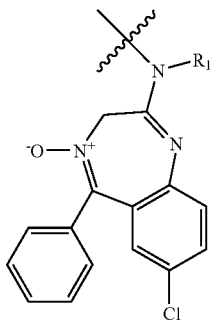
MMMM
chlordiazepoxide
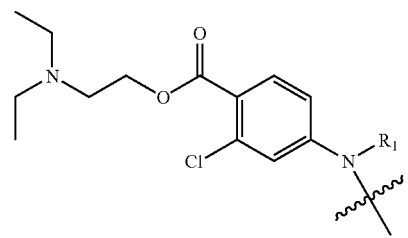
NNNN
chloroprocaine
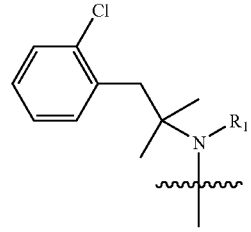
OOOO
clortermine
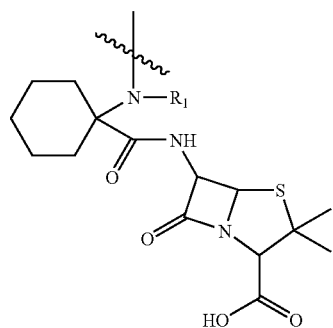
PPPP
cyclacillin TABLE 1-continued Formula for Q QQQQ
cyclopenthiazide RRRR
cycloserine SSSS
cysteamine TTTT
dezocine UUUU
dobutamine VVVV-1
eflornithine TABLE 1-continued
Formula for Q
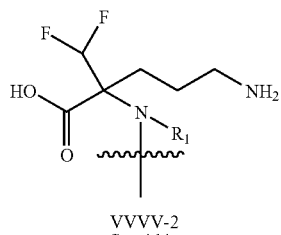
VVVV-2
eflornithine
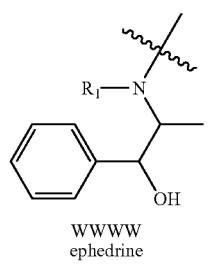
WWWW
ephedrine
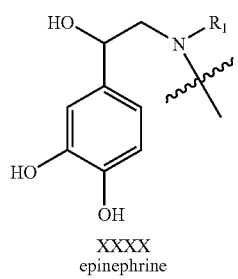
XXXX
epinephrine
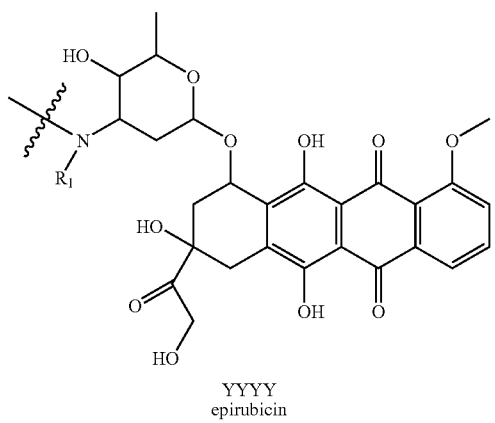
YYYY
epirubicin
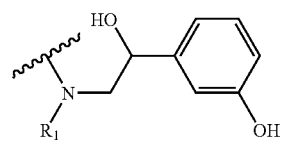
ZZZZ
etilefrine TABLE 1-continued
| Formula for Q |
|---|
| 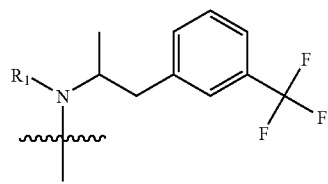<br>AAAAA<br>fenfluramine |
| 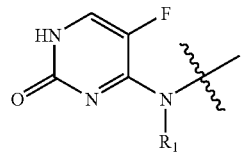<br>BBBBB<br>flucytosine |
| 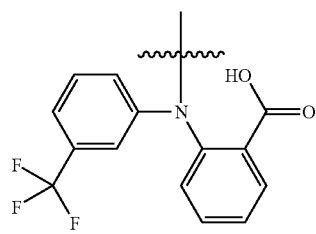<br>CCCCC<br>flufenamic acid |
| 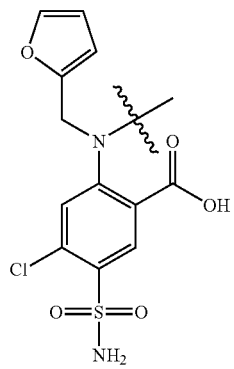<br>DDDDD<br>furosemide |
| 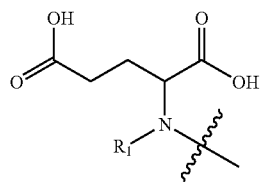<br>EEEEE<br>glutamic acid |

TABLE 1-continued

Formula for Q

FFFFF
glutamine

GGGGG
glutathione

HHHHH
glycine

IIIII
histamine

JJJJJ-1
hydralazine

JJJJJ-2
hydralazine

TABLE 1-continued
Formula for Q
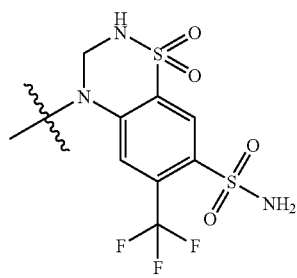
KKKKK
hydroflumethiazide
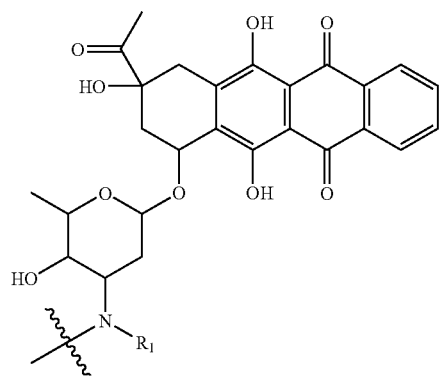
LLLLL
idarubicin
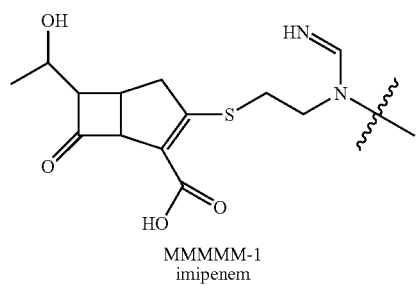
MMMMM-1
imipenem
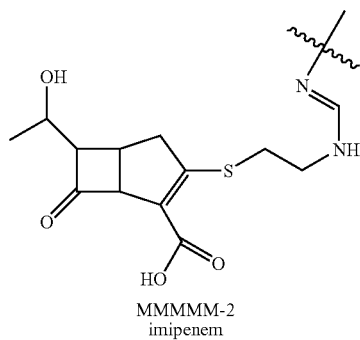
MMMMM-2
imipenem TABLE 1-continued
Formula for Q
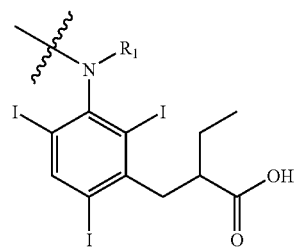
NNNNN
iopanoic acid
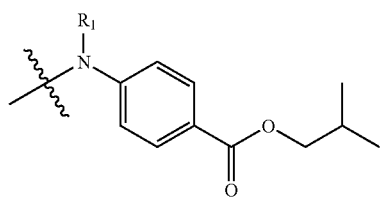
OOOOO
isocaine
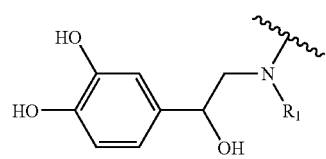
PPPPP
isoproterenol
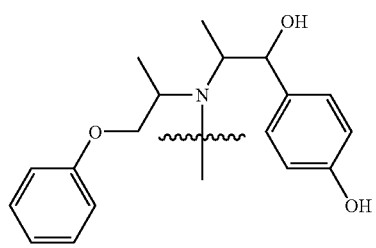
QQQQQ
isoxsuprine
RRRRR
ketamine TABLE 1-continued
Formula for Q
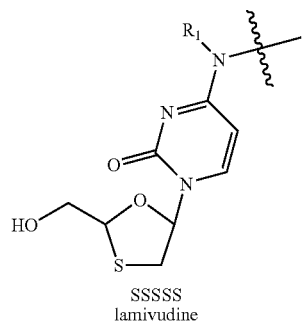
SSSSS
lamivudine
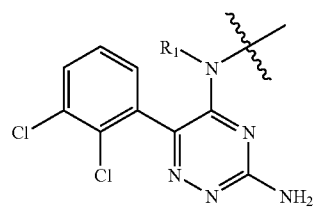
TTTTT-1
lamotrigine
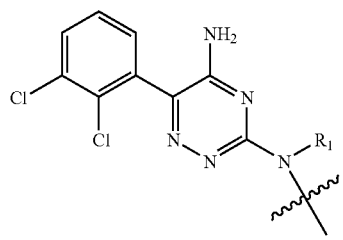
TTTTT-2
lamotrigine
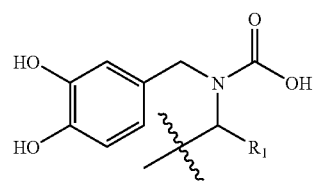
UUUUU
levodopa
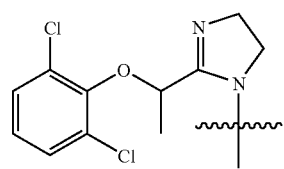
VVVVV
lofexidine TABLE 1-continued
Formula for Q
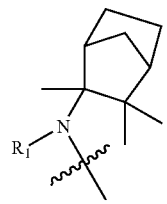
WWWWW
mecamylamine
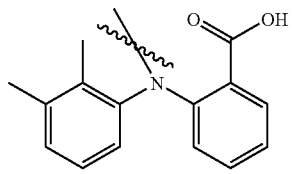
XXXXX
mefenamic acid
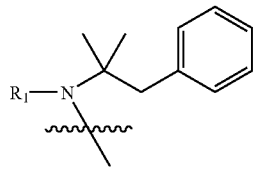
YYYYY
mephentermine
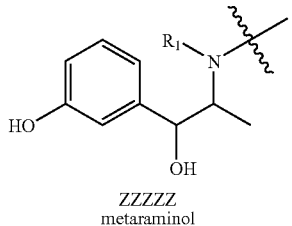
ZZZZZ
metaraminol
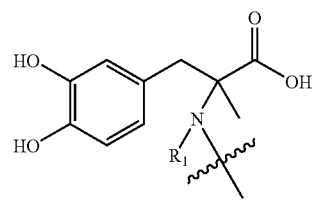
2A
methyldopa
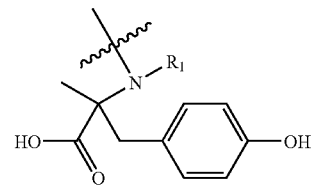
2B
metyronsine TABLE 1-continued
Formula for Q
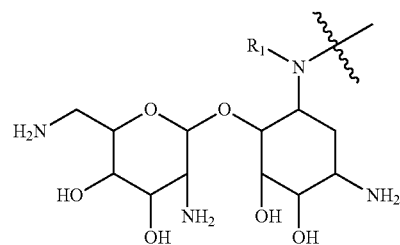
2C-1
neomycin A-1
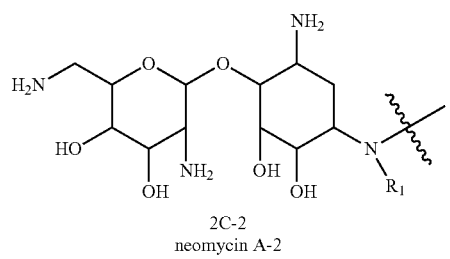
2C-2
neomycin A-2
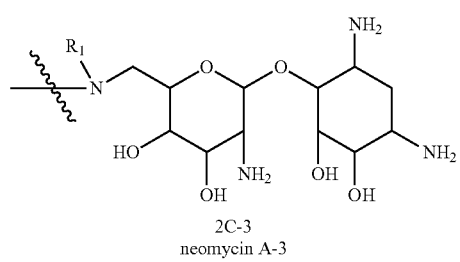
2C-3
neomycin A-3
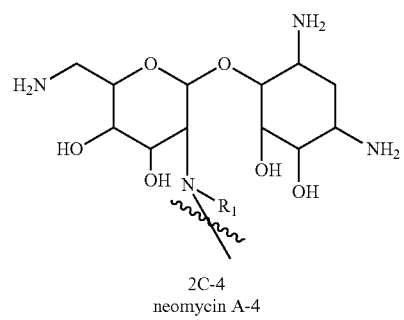
2C-4
neomycin A-4
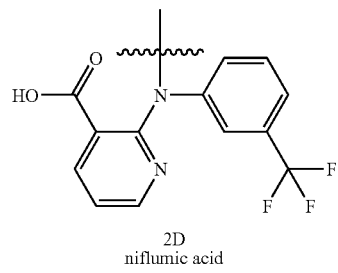
2D
niflumic acid TABLE 1-continued
Formula for Q
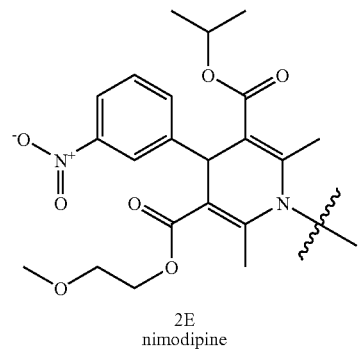
2E
nimodipine
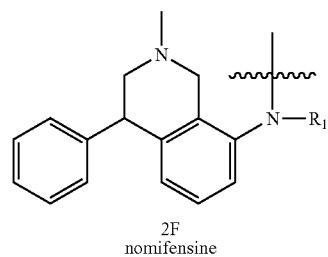
2F
nomifensine
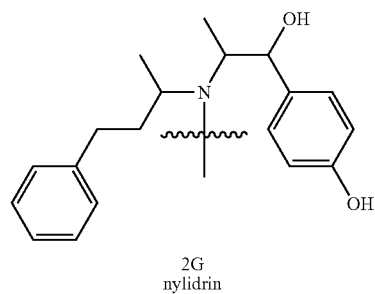
2G
nylidrin
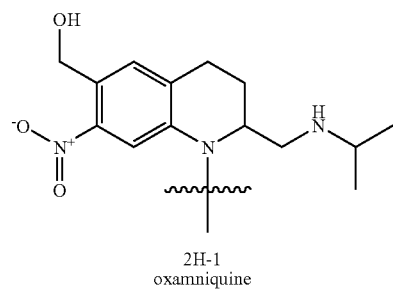
2H-1
oxamniquine
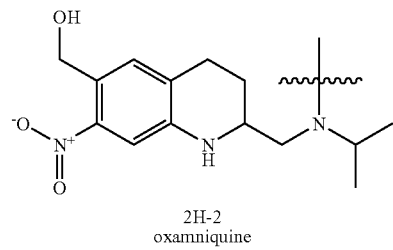
2H-2
oxamniquine TABLE 1-continued
Formula for Q
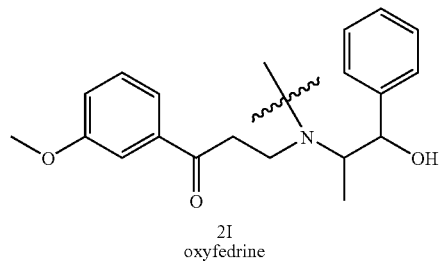
2I
oxyfedrine
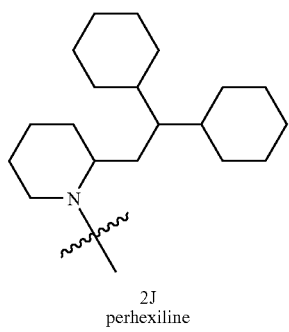
2J
perhexiline
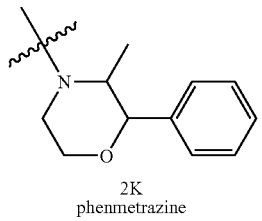
2K
phenmetrazine
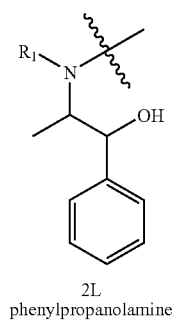
2L
phenylpropanolamine
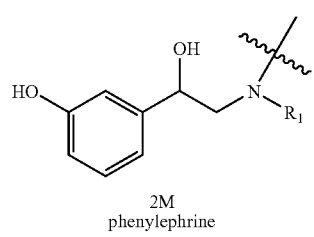
2M
phenylephrine TABLE 1-continued
Formula for Q
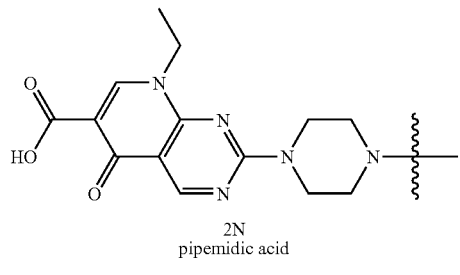
2N
pipemidic acid
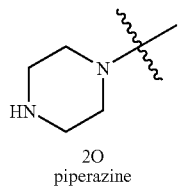
2O
piperazine
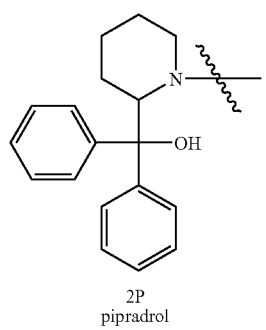
2P
pipradrol
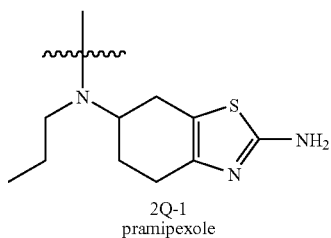
2Q-1
pramipexole
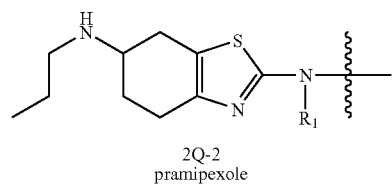
2Q-2
pramipexole TABLE 1-continued
Formula for Q
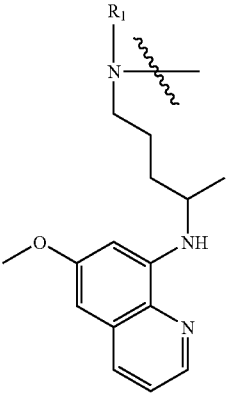
2R-1
primaquine
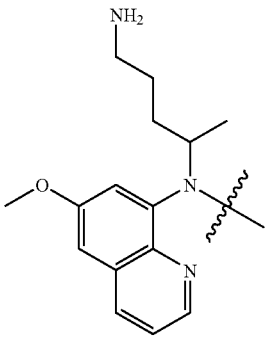
2R-2
primaquine
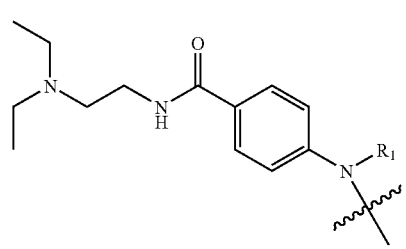
2S
procainamide
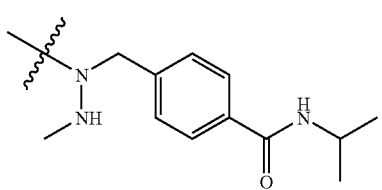
2T-1
procarbazine
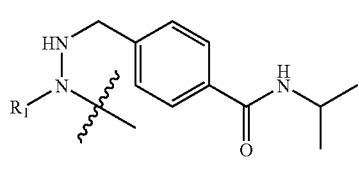
2T-2
procarbazine TABLE 1-continued
Formula for Q
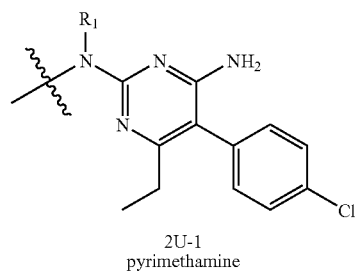
2U-1
pyrimethamine
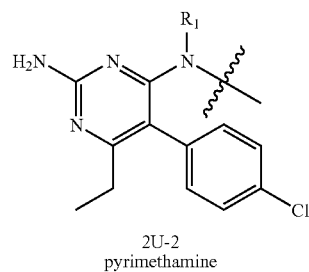
2U-2
pyrimethamine
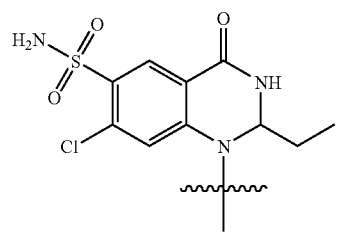
2V
quinethazone
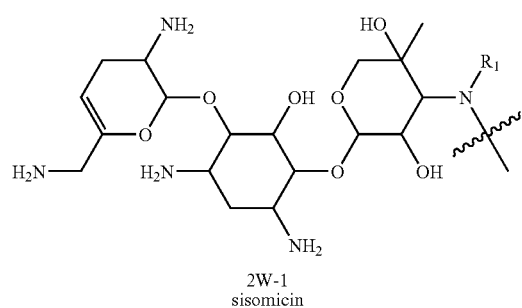
2W-1
sisomicin
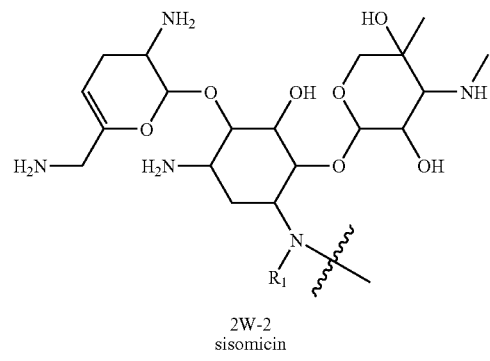
2W-2
sisomicin TABLE 1-continued
Formula for Q
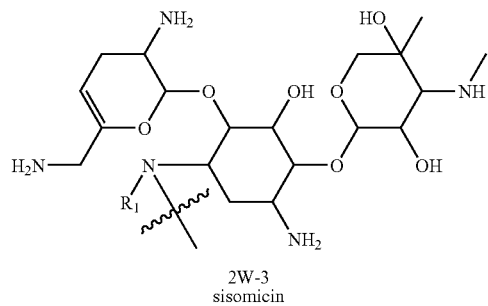
2W-3
sisomicin
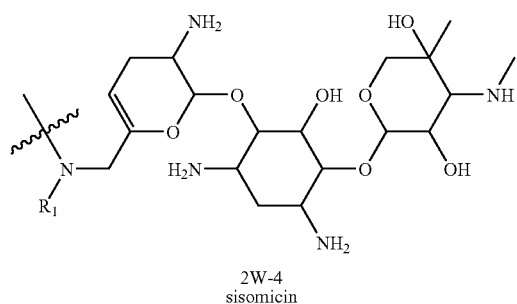
2W-4
sisomicin
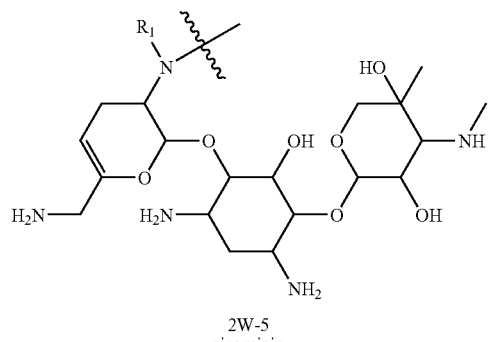
2W-5
sisomicin
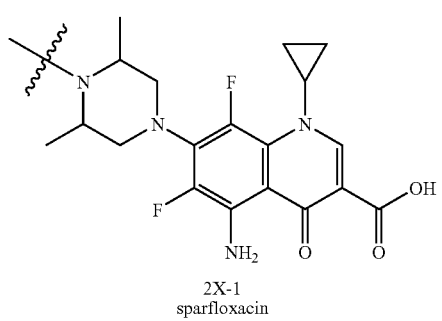
2X-1
sparfloxacin TABLE 1-continued
Formula for Q
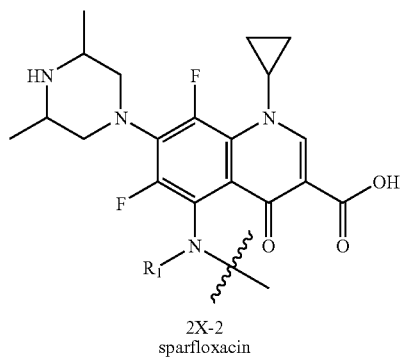
2X-2
sparfloxacin
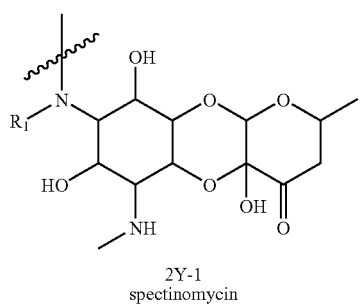
2Y-1
spectinomycin
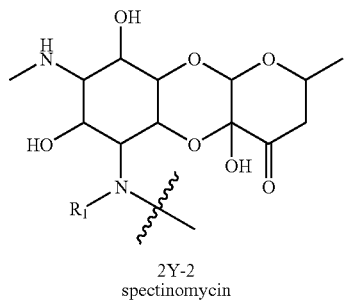
2Y-2
spectinomycin
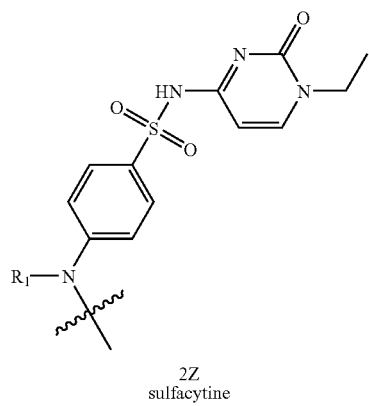
2Z
sulfacytine TABLE 1-continued
Formula for Q
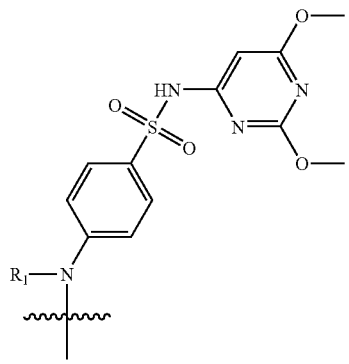
2AA
sulfadimethoxine
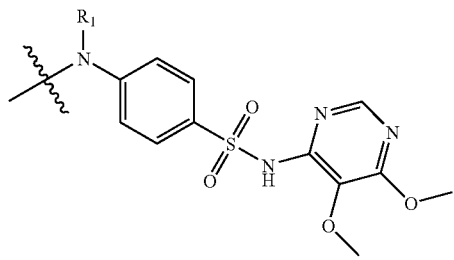
2BB
sulfadoxine
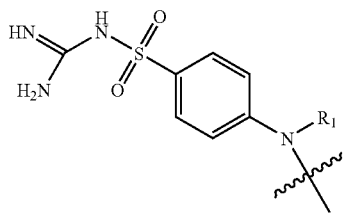
2CC-1
sulfaguanidine
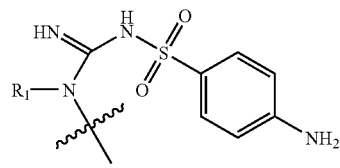
2CC-2
sulfaguanidine
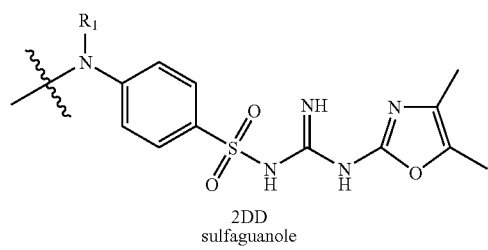
2DD
sulfaguanole TABLE 1-continued
Formula for Q
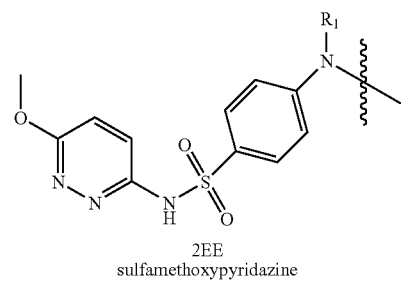
2EE
sulfamethoxypyridazine
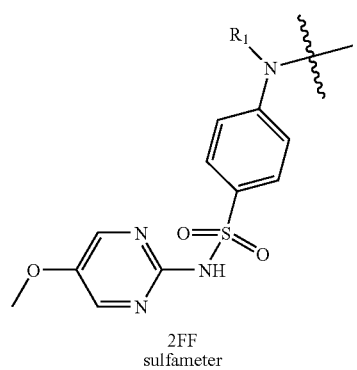
2FF
sulfameter
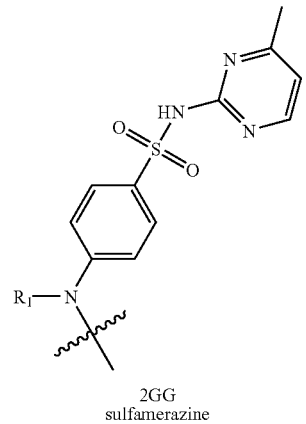
2GG
sulfamerazine
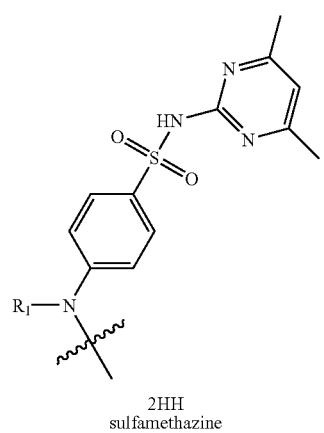
2HH
sulfamethazine TABLE 1-continued
| Formula for Q |
|---|
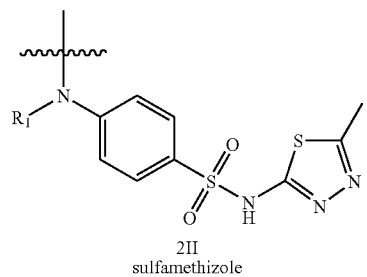
2II
sulfamethizole
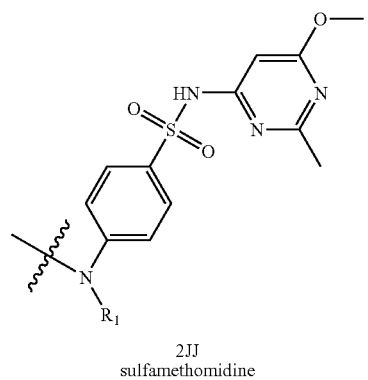
2JJ
sulfamethomidine
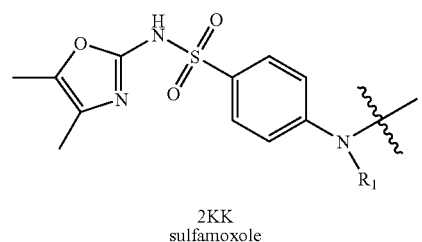
2KK
sulfamoxole
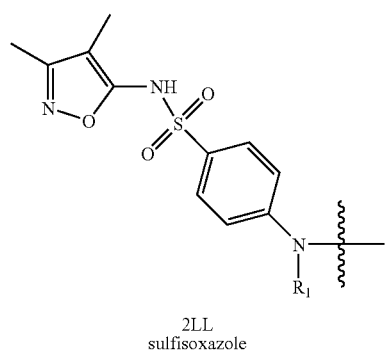
2LL
sulfisoxazole TABLE 1-continued
Formula for Q
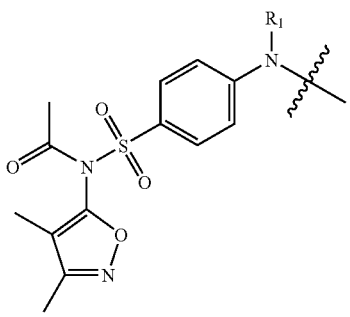
2MM
sulfisoxazole acetal
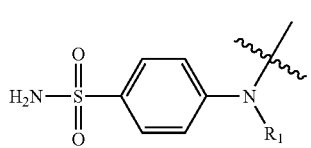
2NN
sulfonamide CS61
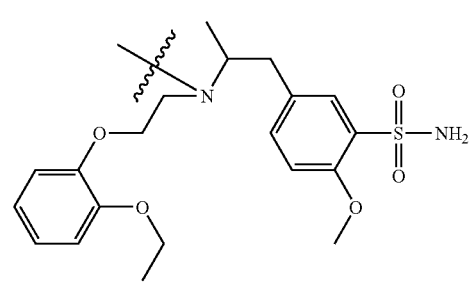
2OO
tamsulosin
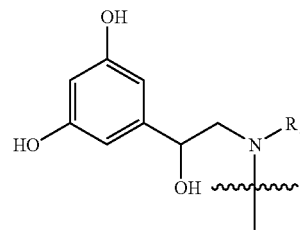
2PP
terbutaline
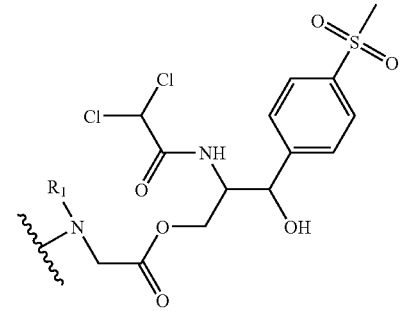
2QQ
thiamphenicol TABLE 1-continued
Formula for Q
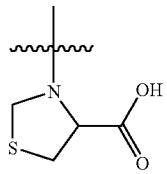
2RR
timonacic
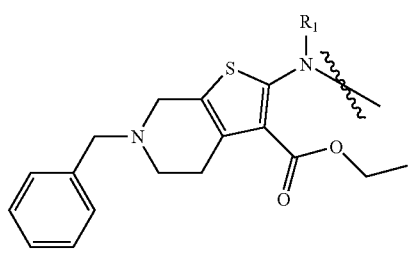
2SS
tinoridine
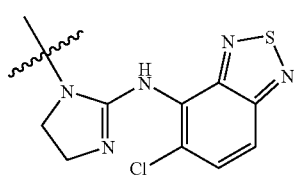
2TT-1
tizanidine
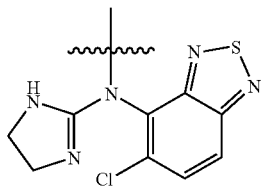
2TT-2
tizanidine
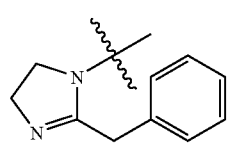
2UU
tolazoline
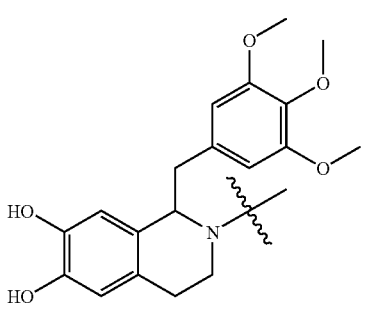
2VV
tretoquinol TABLE 1-continued
Formula for Q
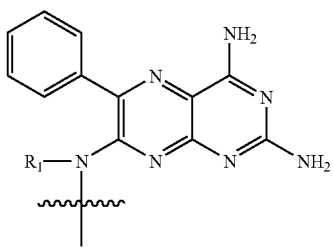
2WW-1
triamterene
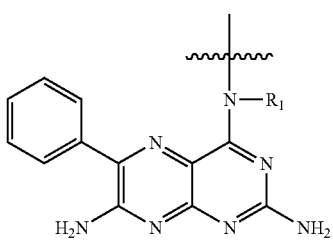
2WW-2
triamterene
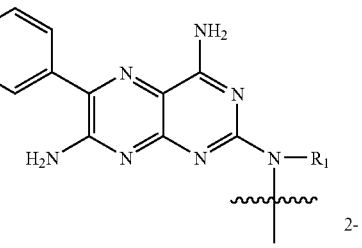
2-
WW-3
triamterene
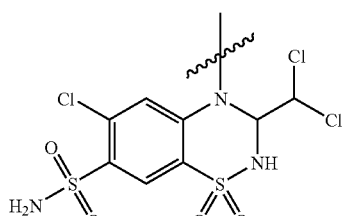
2XX
trichlormethiazide
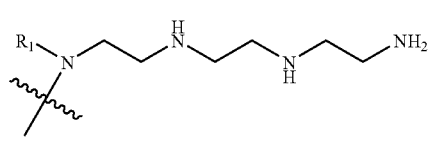
2YY-1
trientine
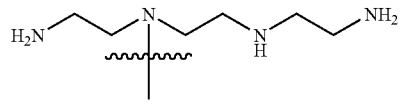
2YY-2
trientine TABLE 1-continued
Formula for Q
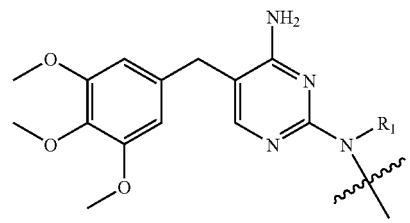
2ZZ-1
trimethoprim
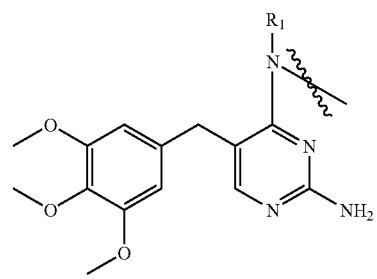
2ZZ-2
trimethoprim
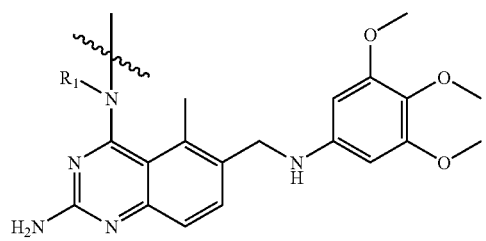
2AAA-1
trimetrexate
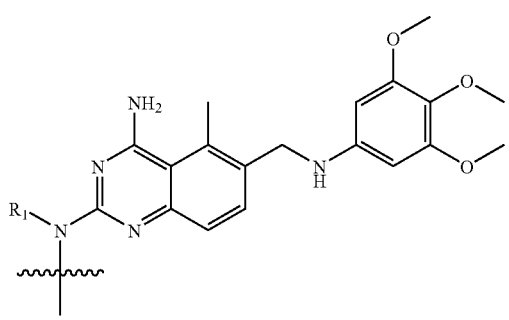
2AAA-2
trimetrexate
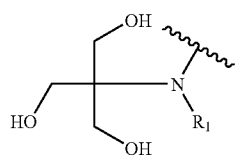
2BBB
tromethamine TABLE 1-continued
Formula for Q
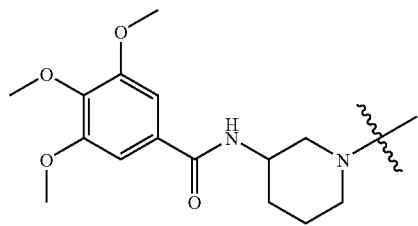
2CCC
troxipide
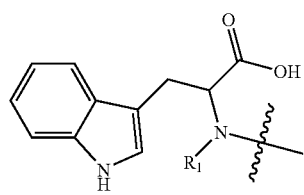
2DDD
tryptophan
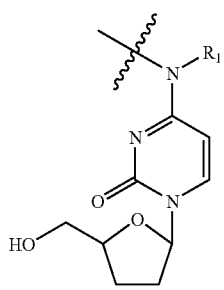
2EEE
zalcitibine
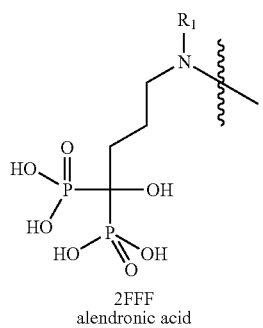
2FFF
alendronic acid
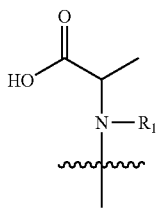
2GGG
alanine TABLE 1-continued
Formula for Q
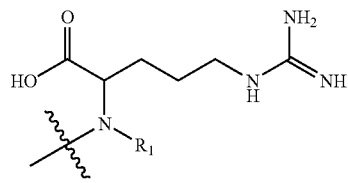
2HHH-1
arginine
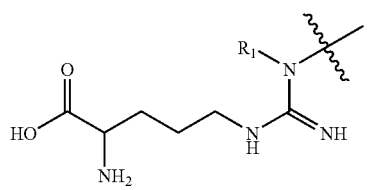
2HHH-2
arginine
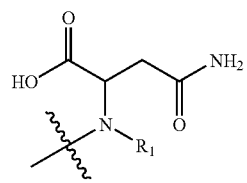
2III
asparagine
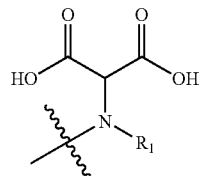
2JJJ
aspartic acid
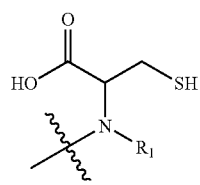
2KKK
cysteine
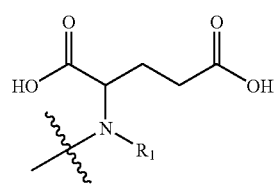
2LLL
glutamic acid TABLE 1-continued
Formula for Q
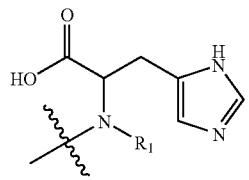
2MMM-1
histidine
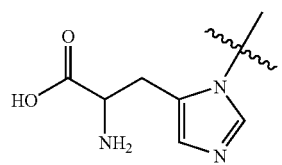
2MMM-2
histidine
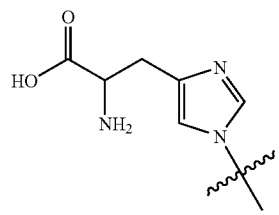
2MMM-3
histidine
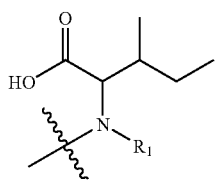
2NNN
isoleucine
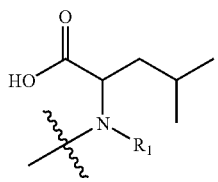
2OOO
leucine
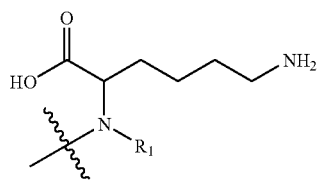
2PPP-1
lysine TABLE 1-continued
Formula for Q
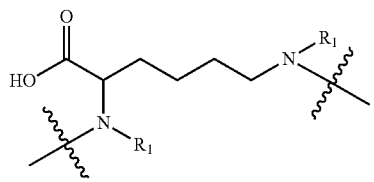
2PPP-2
lysine
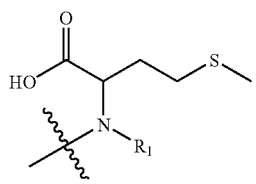
2QQQ
methionine
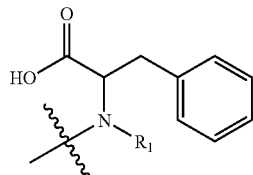
2RRR
phenylalanine
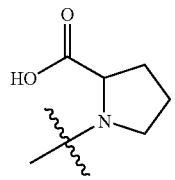
2SSS
proline
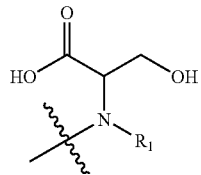
2TTT
serine
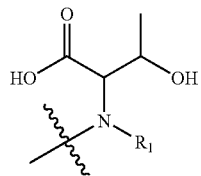
2UUU
threonine TABLE 1-continued Formula for Q 2VVV
tyrosine 2WWW
valine 2XXX
deferoxamine 2YYY
mesalamine 2ZZZ
phentolamine TABLE 1-continued
Formula for Q
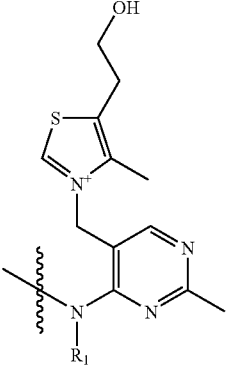
2AAAA
thiamine
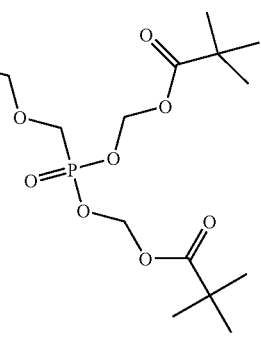
2BBBB
adefovir dipivoxil
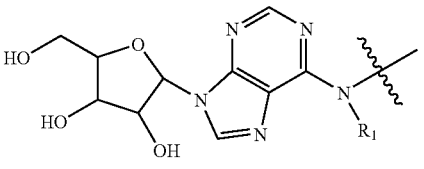
2CCCC
adenosine
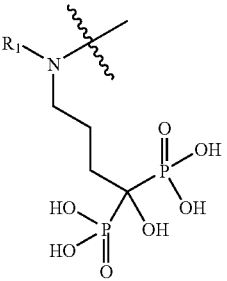
2EEEE
alendronate TABLE 1-continued
Formula for Q
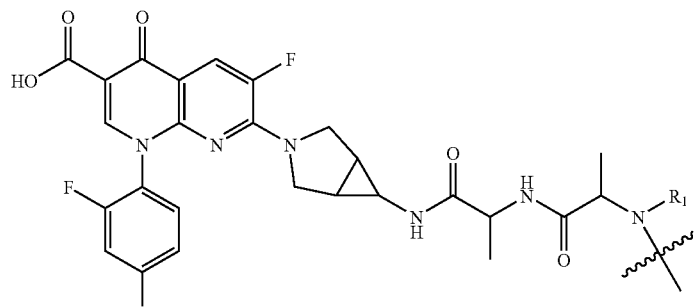
2DDDD
Alatrofloxacin
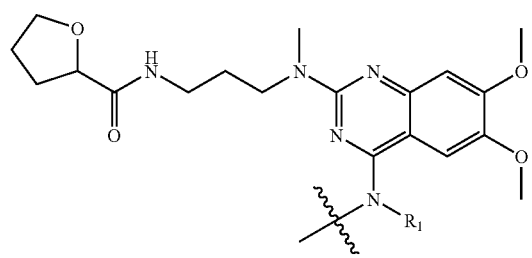
2FFFF
alfuzosin
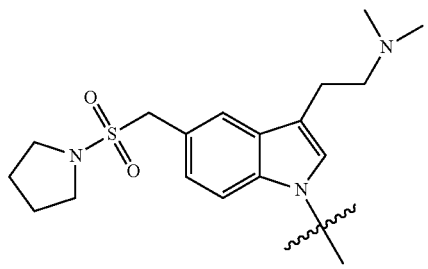
2GGGG
almotriptan
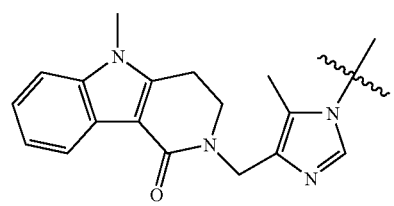
2HHHH
alosetron
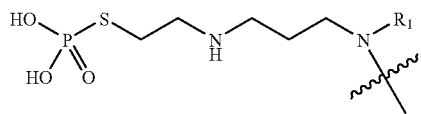
2IIII-1
amifostine
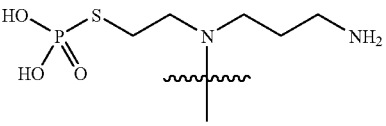
2IIII-2
amifostine TABLE 1-continued
Formula for Q
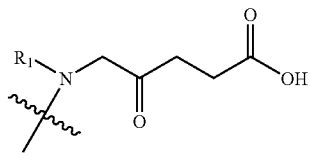
2JJJJ
levulan
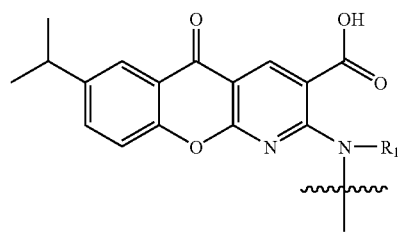
2KKKK
amlexanox
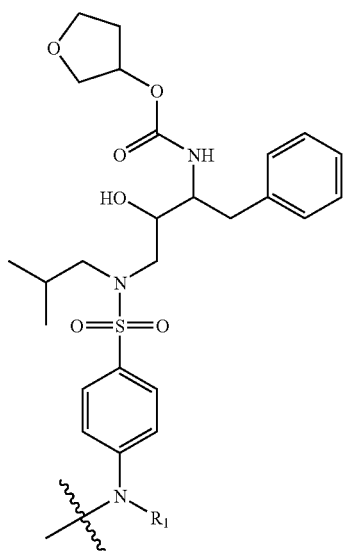
2LLLL
amprenavir
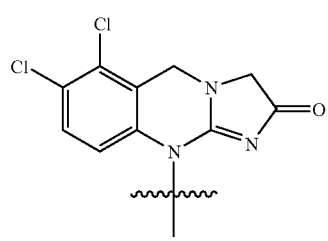
2MMMM
anagrelide TABLE 1-continued
Formula for Q
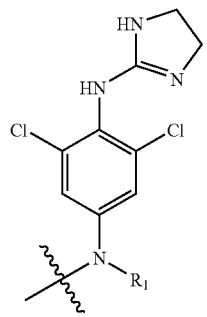
2NNNN-1
apraclonidine
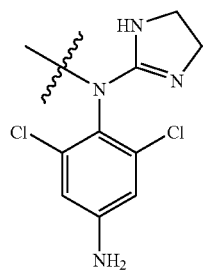
2NNNN-2
apraclonidine
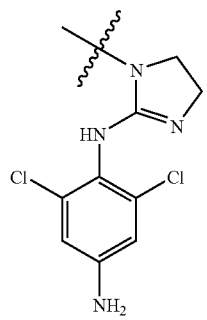
2NNNN-3
apraclonidine
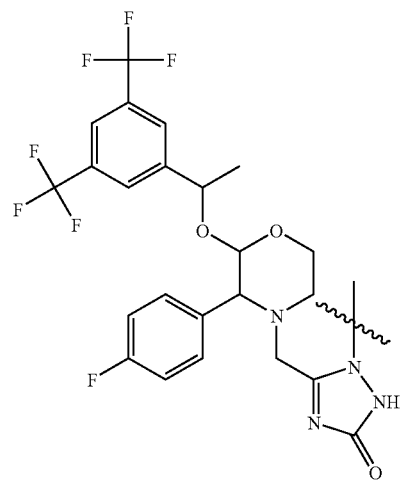
2OOOO-1
aprepitant TABLE 1-continued
Formula for Q
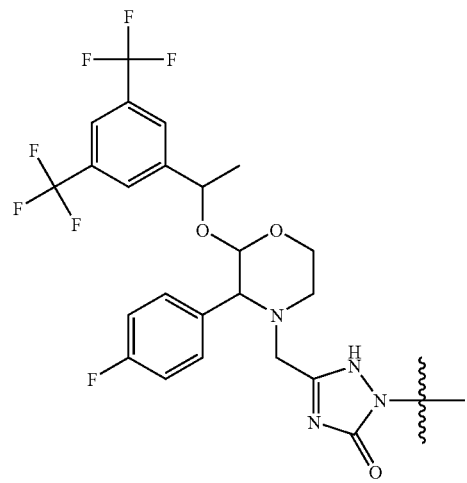
2OOOO-2
aprepitant
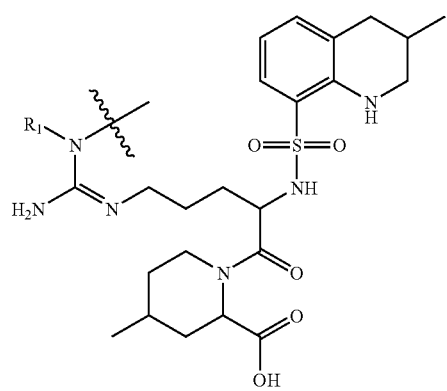
2PPPP-1
argatroban
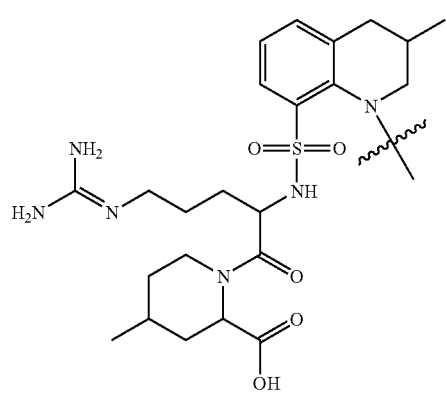
2PPPP-2
argatroban TABLE 1-continued
Formula for Q
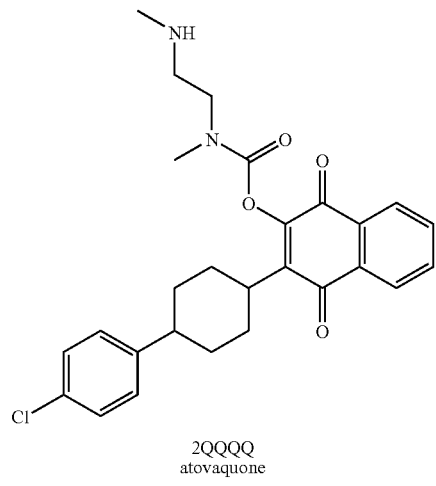
2QQQQ
atovaquone
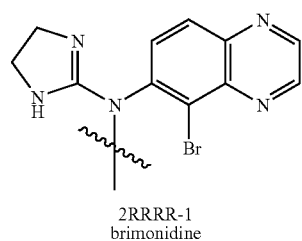
2RRRR-1
brimonidine
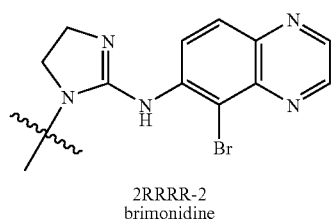
2RRRR-2
brimonidine
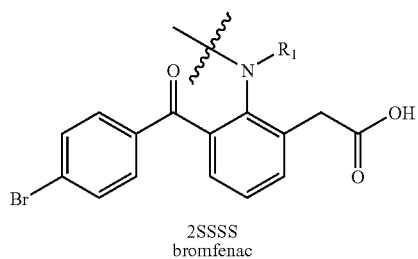
2SSSS
bromfenac TABLE 1-continued
Formula for Q
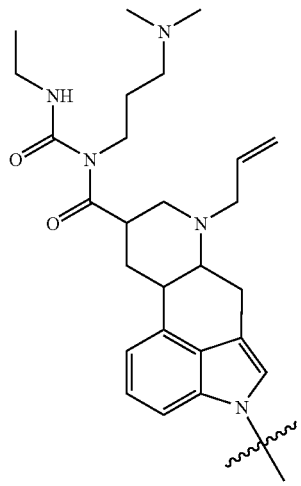
2TTTT
cabergoline
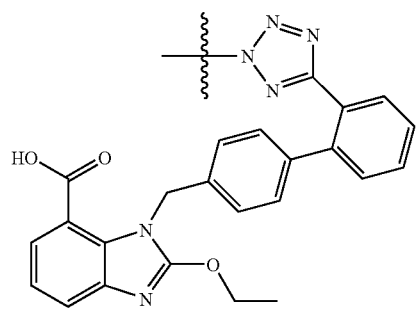
2UUUU-1
candesartan
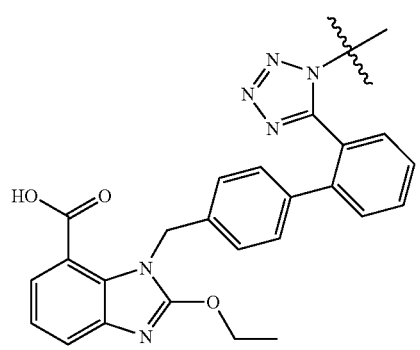
2UUUU-2
candesartan TABLE 1-continued
Formula for Q
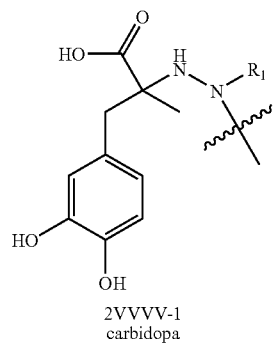
2VVVV-1
carbidopa
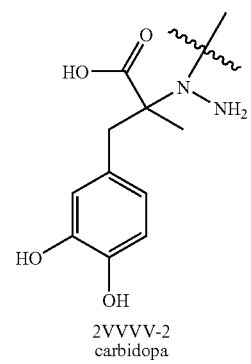
2VVVV-2
carbidopa
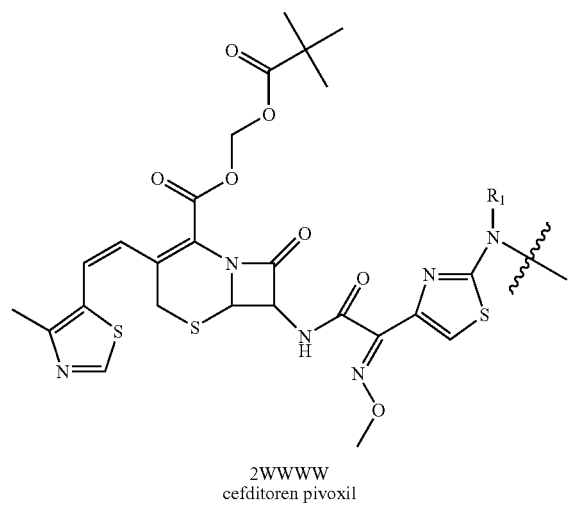
2WWWW
cefditoren pivoxil US 8,101,782 B2
115                                                                                                    116
TABLE 1-continued
Formula for Q
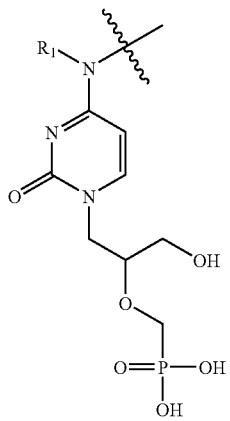
2XXXX
cidofovir
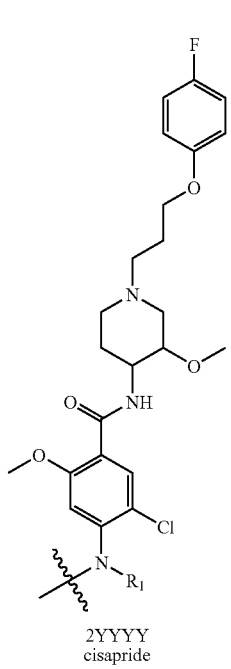
2YYYY
cisapride
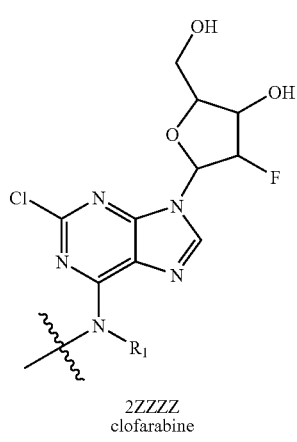
2ZZZZ
clofarabine TABLE 1-continued
| Formula for Q |
|---|
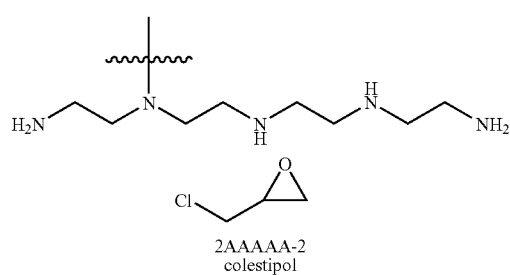
2AAAAA-1
colestipol
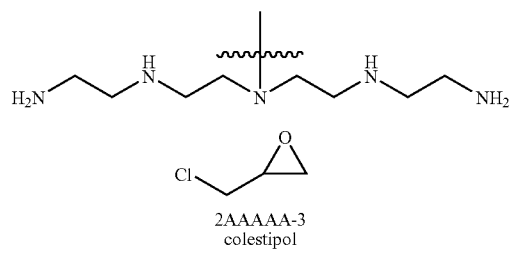
2AAAAA-2
colestipol
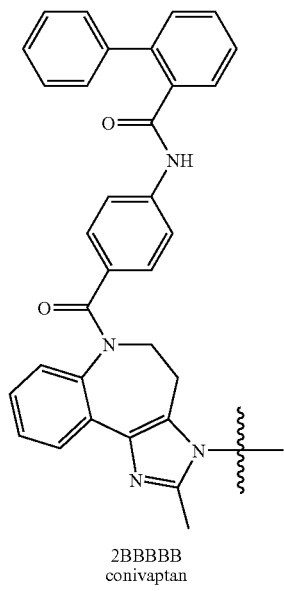
2AAAAA-3
colestipol
2BBBBB
conivaptan TABLE 1-continued
Formula for Q
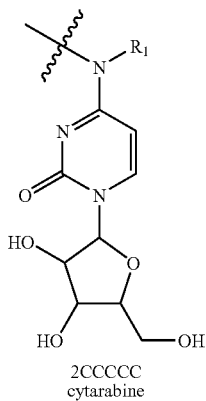
2CCCCC
cytarabine
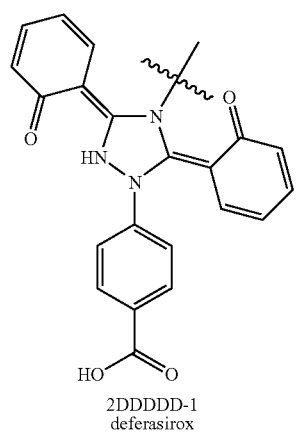
2DDDDD-1
deferasirox
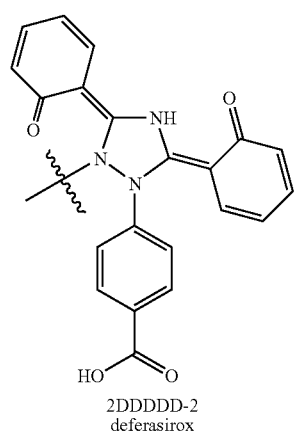
2DDDDD-2
deferasirox TABLE 1-continued
Formula for Q
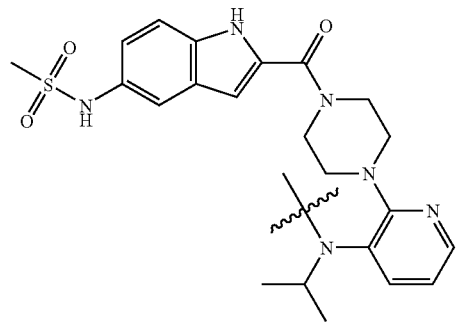
2EEEEE-1
delavirdine
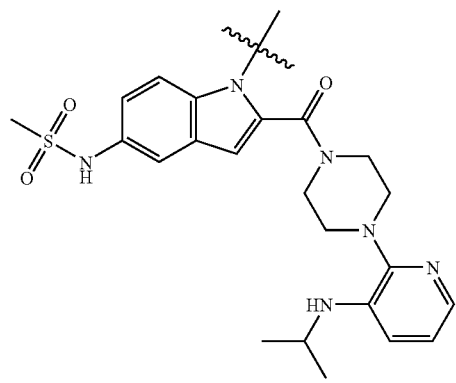
2EEEEE-2
delavirdine
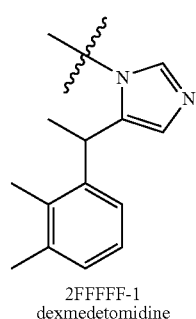
2FFFFF-1
dexmedetomidine
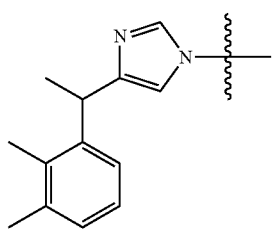
2FFFFF-2
dexmedetomidine TABLE 1-continued
Formula for Q
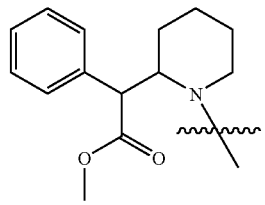
2GGGGG
dexmethylphenidate
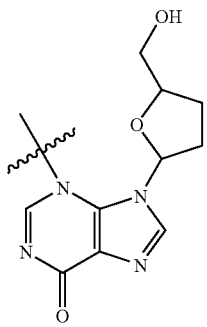
2HHHHH
didanosine
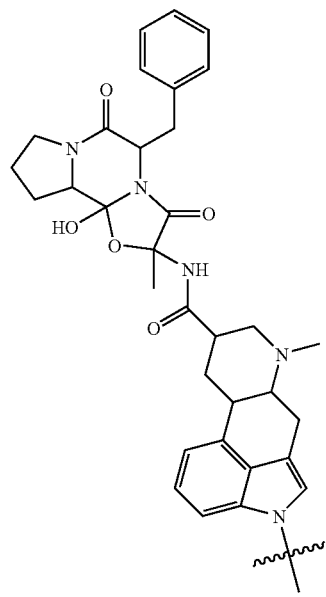
2IIIII
migranal
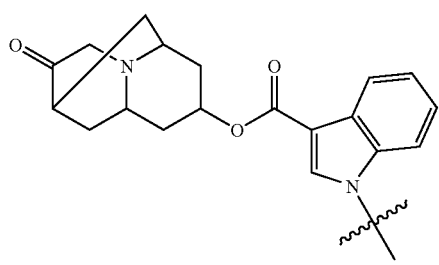
2JJJJJ
dolasetron TABLE 1-continued
Formula for Q
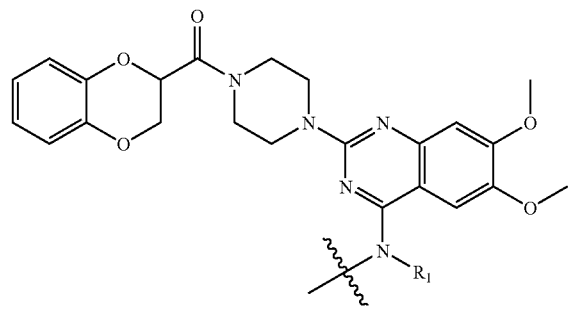
2KKKKK
doxazosin
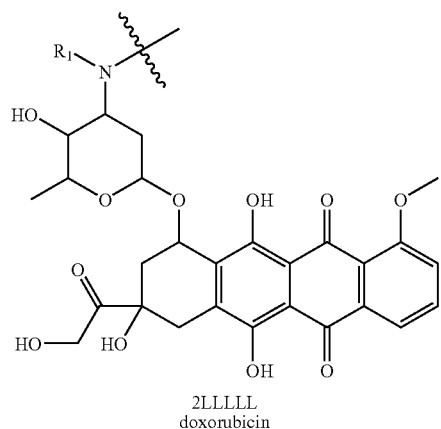
2LLLLL
doxorubicin
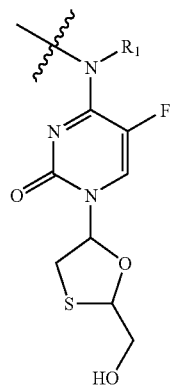
2MMMMM
emtricitabine TABLE 1-continued Formula for Q 2NNNNN
enalapril 2OOOOO
felodipine 2PPPPP
epinastine TABLE 1-continued
Formula for Q
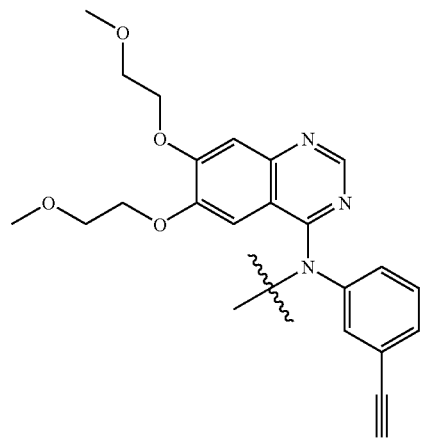
2QQQQQ
erlotinib
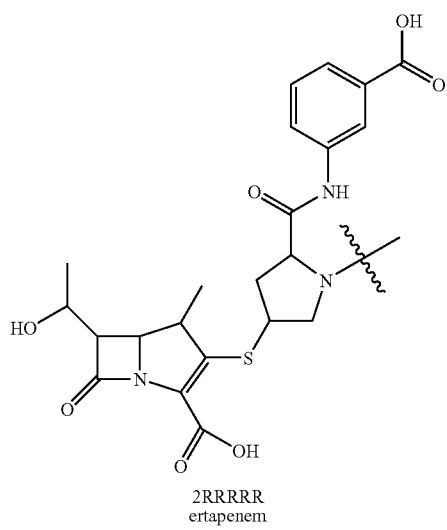
2RRRRR
ertapenem
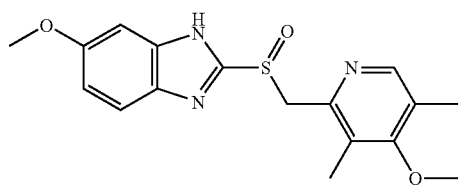
2SSSSS
omeprazole
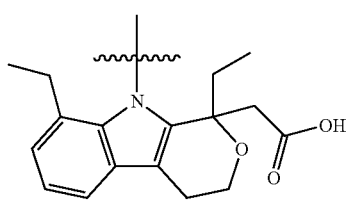
2TTTTT
etodolac TABLE 1-continued
Formula for Q
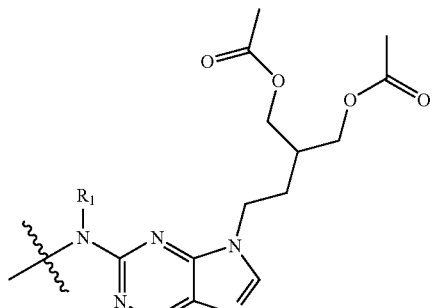
2UUUU
famciclovir
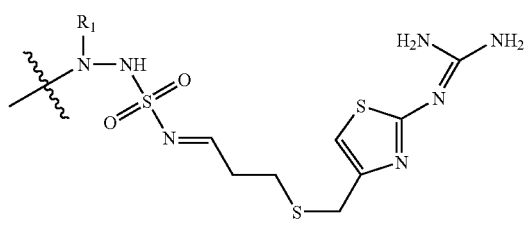
2VVVVV-1
famotidine
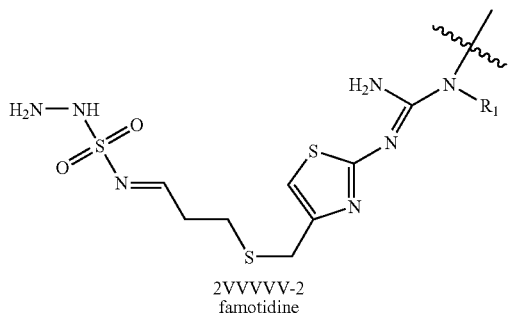
2VVVVV-2
famotidine
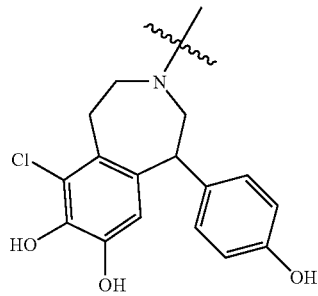
2WWWWW
fenoldopam
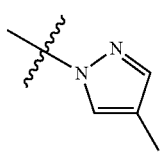
2XXXXX-1
fomepizole

TABLE 1-continued
Formula for Q
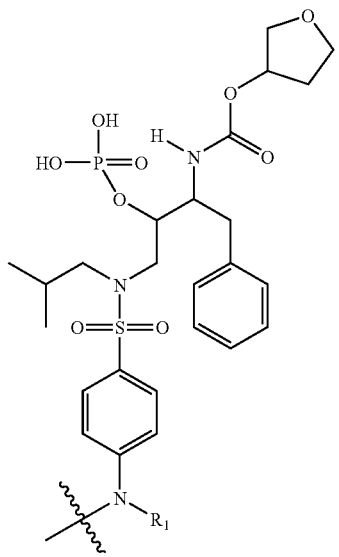
2YYYYY
fosamprenavir
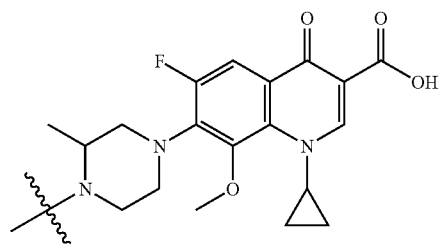
2ZZZZZ
gatifloxacin
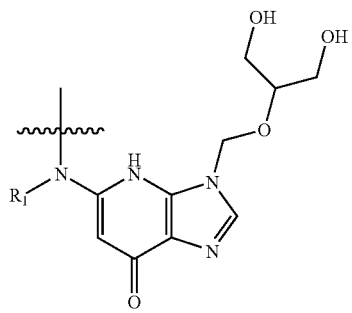
3A-1
ganciclovir TABLE 1-continued
Formula for Q
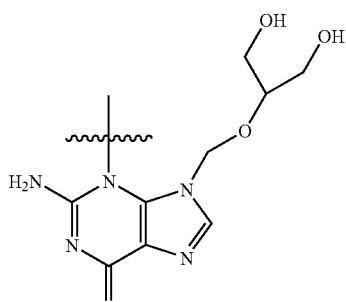
3A-2
ganciclovir
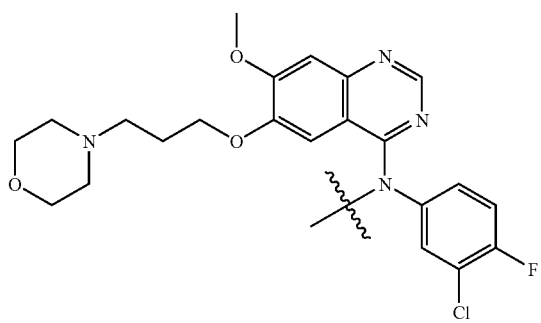
3B
gefitinib
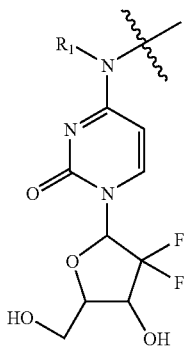
3C
gemcitabine
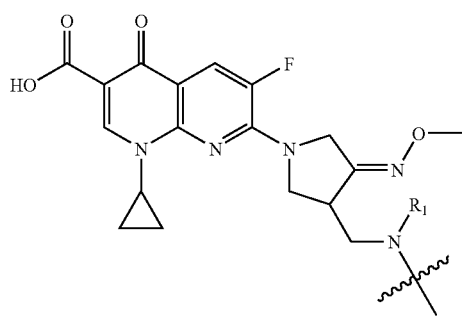
3D
gemofloxacin TABLE 1-continued
Formula for Q
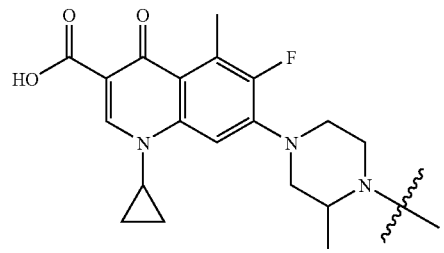
3F
grepafloxacin
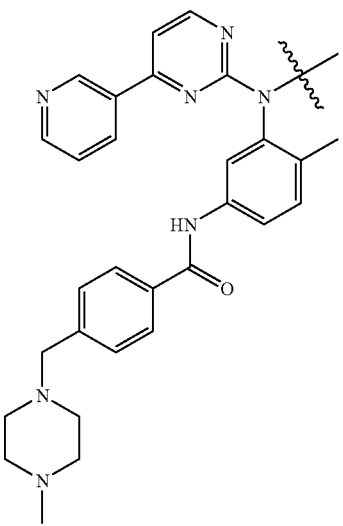
3F
imatinib
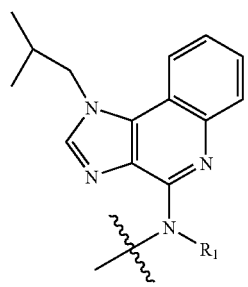
3G
imiquimod TABLE 1-continued
Formula for Q
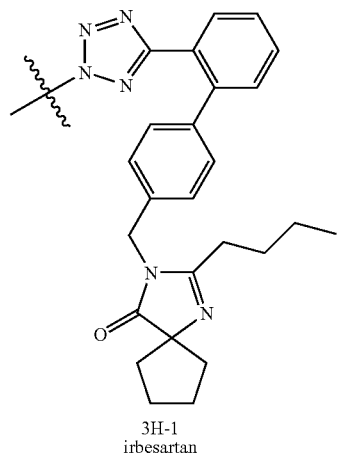
3H-1
irbesartan
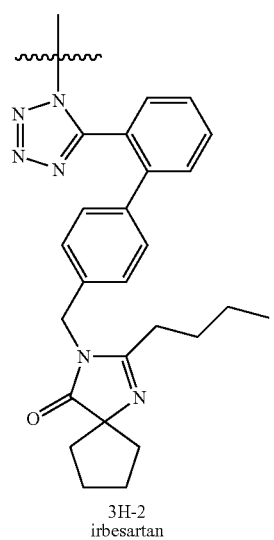
3H-2
irbesartan
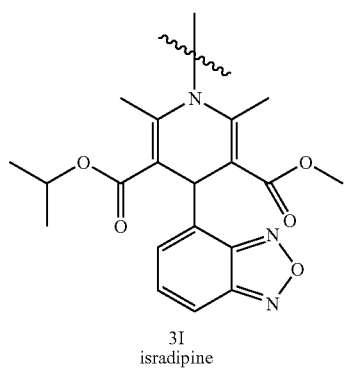
3I
isradipine TABLE 1-continued
| Formula for Q |
|---|
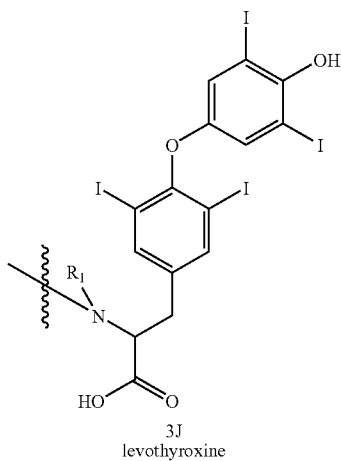
3J
levothyroxine
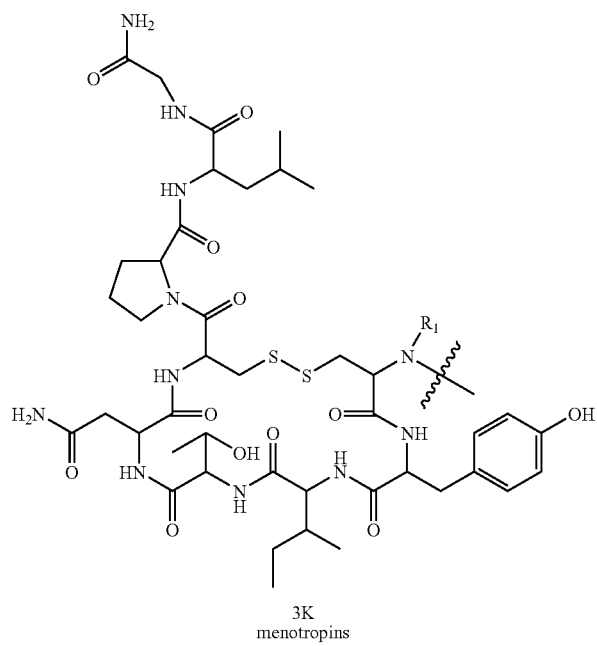
3K
menotropins
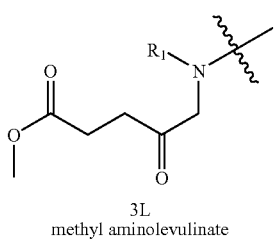
3L
methyl aminolevulinate
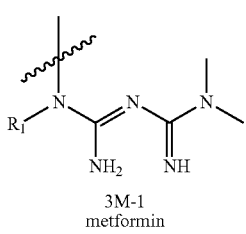
3M-1
metformin

TABLE 1-continued
Formula for Q
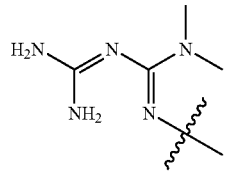
3M-2
metformin
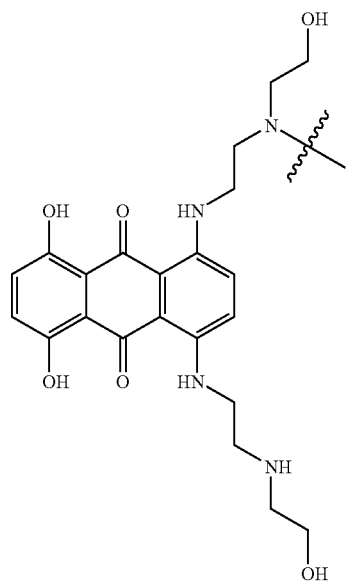
3N-1
mitoxantrone
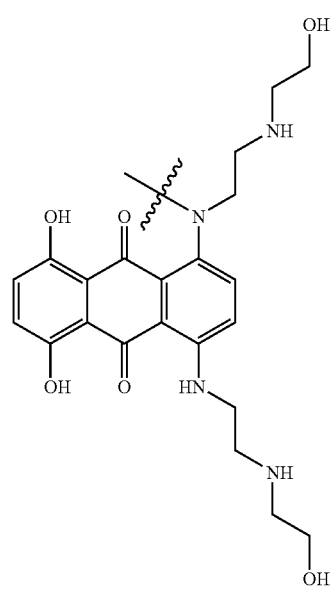
3N-2
mitoxantrone TABLE 1-continued
Formula for Q
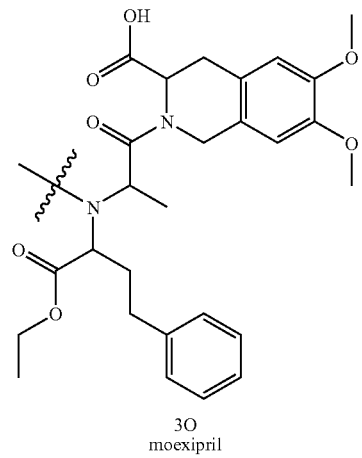
3O
moexipril
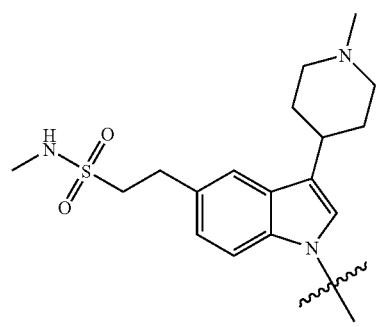
3P
naratriptan
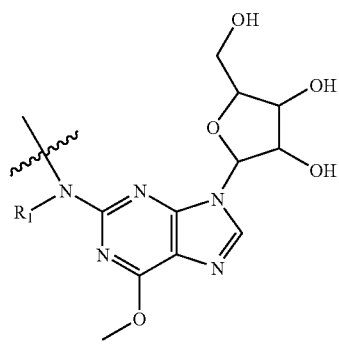
3Q
nelarabine
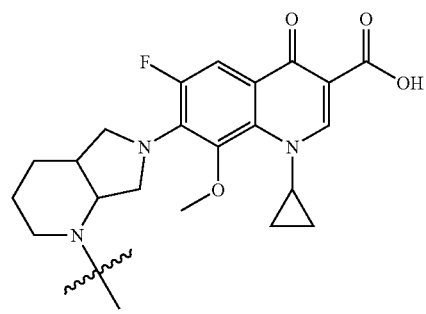
3R
moxifloxacin TABLE 1-continued Formula for Q 3S
nicardipine 3T
nisoldipine 3U-1
nizatidine 3U-2
nizatidine 3V
olanzapine TABLE 1-continued
Formula for Q
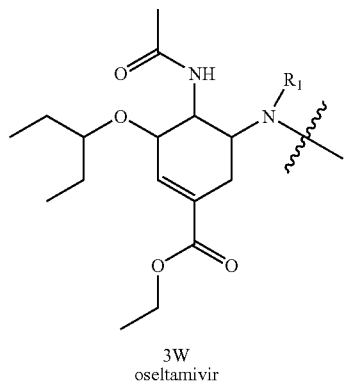
3W
oseltamivir
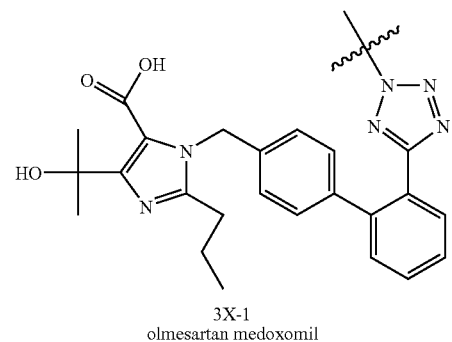
3X-1
olmesartan medoxomil
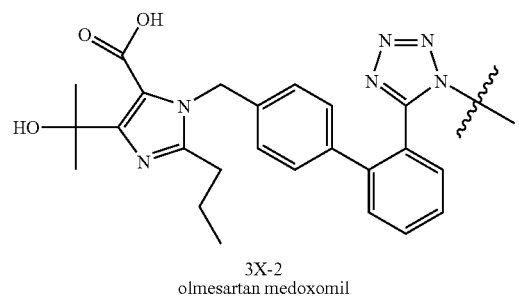
3X-2
olmesartan medoxomil
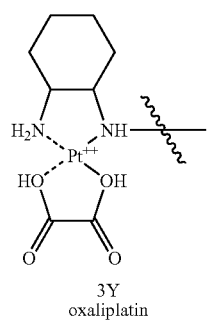
3Y
oxaliplatin

TABLE 1-continued
| Formula for Q |
|---|
| 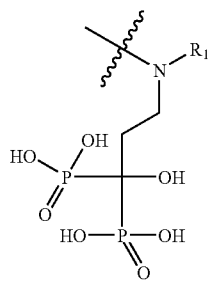<br>3Z<br>pamidronic acid |
| 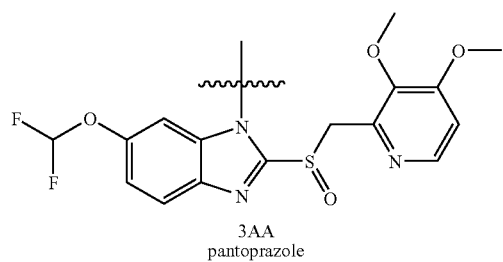<br>3AA<br>pantoprazole |
| 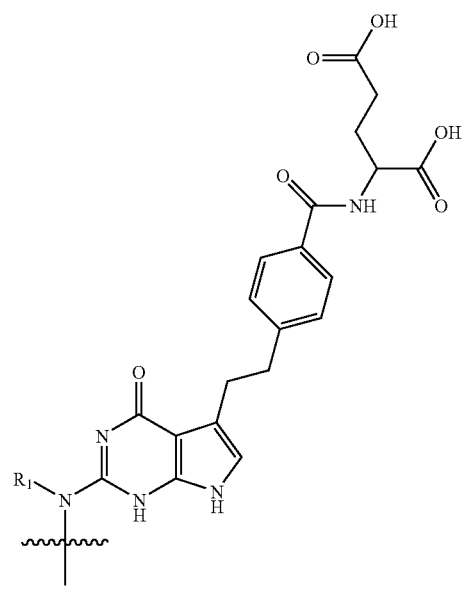<br>3BB-1<br>pemetrexed |

TABLE 1-continued
Formula for Q
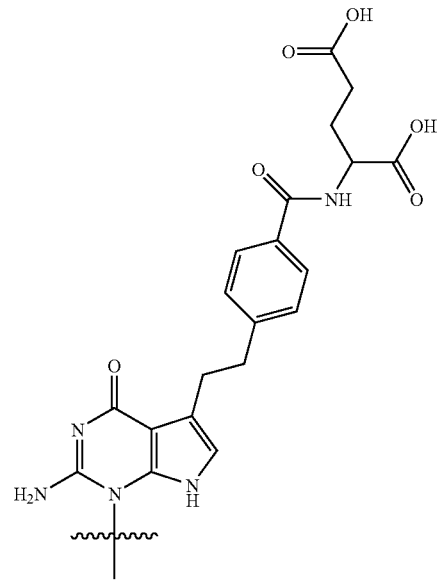
3BB-2
pemetrexed
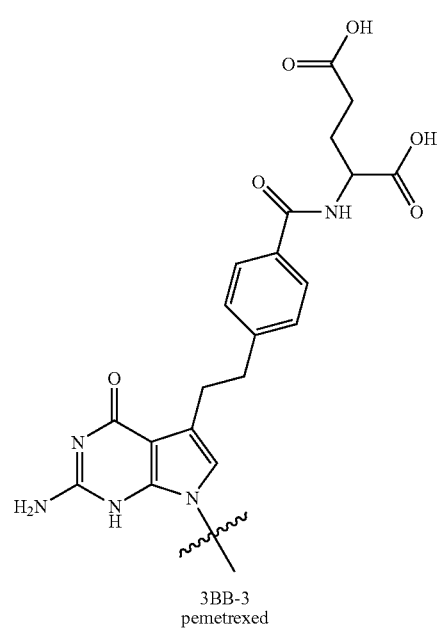
3BB-3
pemetrexed
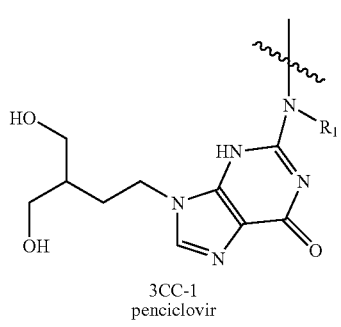
3CC-1
penciclovir TABLE 1-continued Formula for Q 3CC-2
penciclovir 3DD
pergolide 3EE
perindopril 3FF
propafenone TABLE 1-continued
Formula for Q
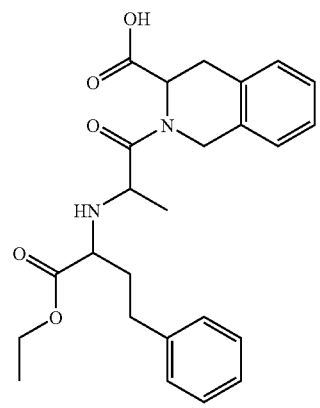
3GG
quinapril
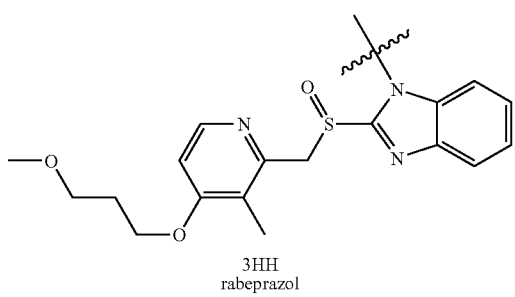
3HH
rabeprazol
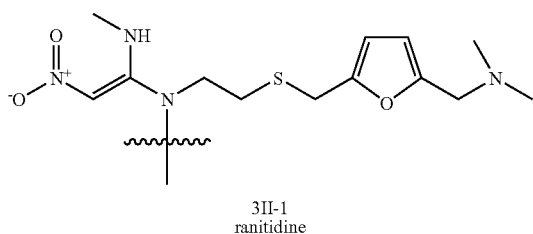
3II-1
ranitidine
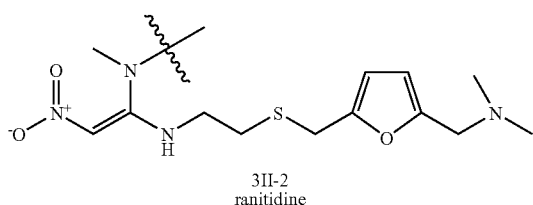
3II-2
ranitidine
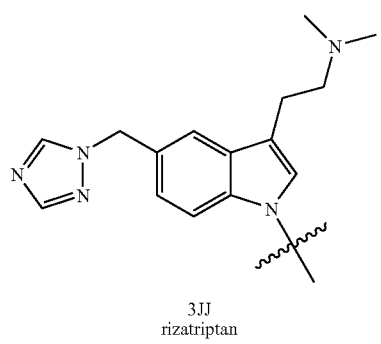
3JJ
rizatriptan

TABLE 1-continued
Formula for Q
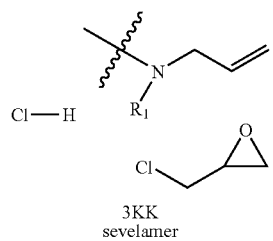
3KK
sevelamer
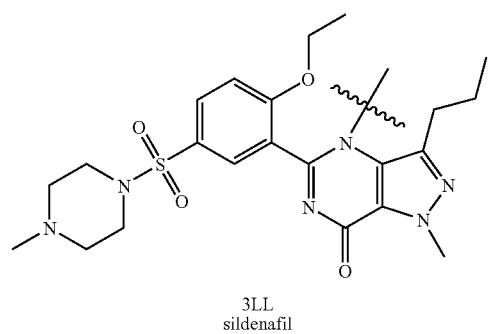
3LL
sildenafil
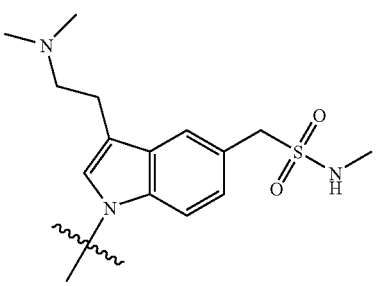
3MM
sumatriptan
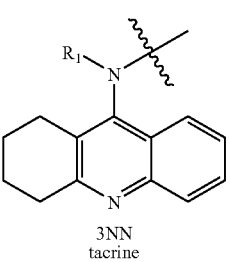
3NN
tacrine
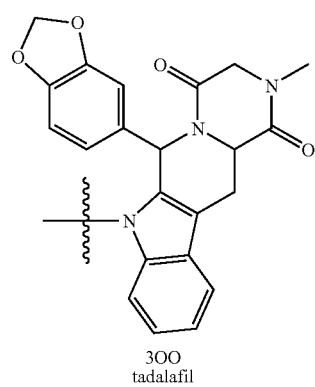
3OO
tadalafil

TABLE 1-continued
Formula for Q
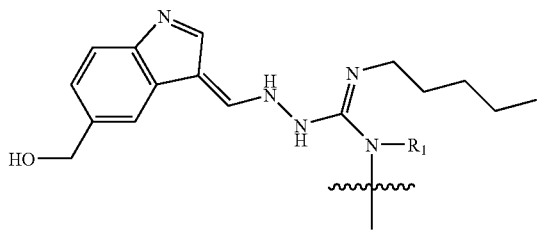
3PP-1
tegaserod
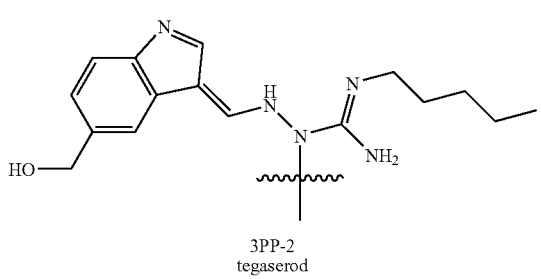
3PP-2
tegaserod
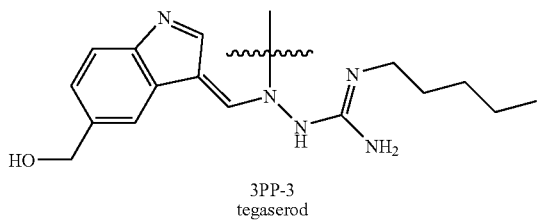
3PP-3
tegaserod
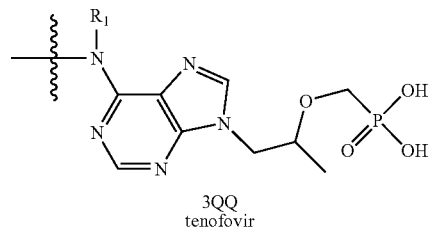
3QQ
tenofovir
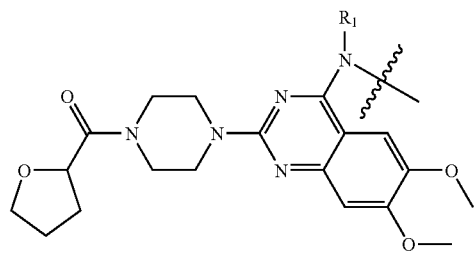
3RR
terazosin
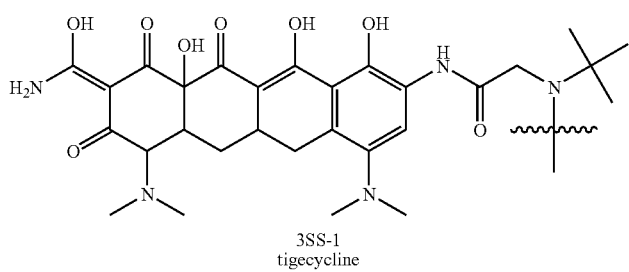
3SS-1
tigecycline TABLE 1-continued Formula for Q 3SS-2
tigecycline 3TT
tirofiban 3UU
torsemide 3VV
trandolapril TABLE 1-continued
Formula for Q
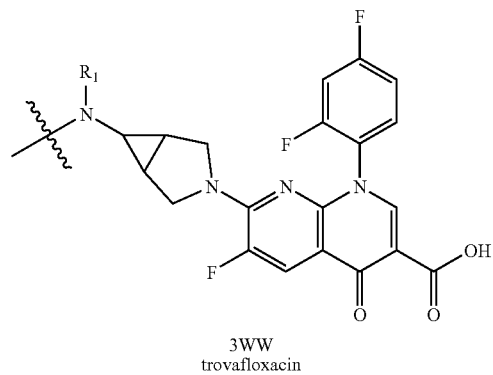
3WW
trovafloxacin
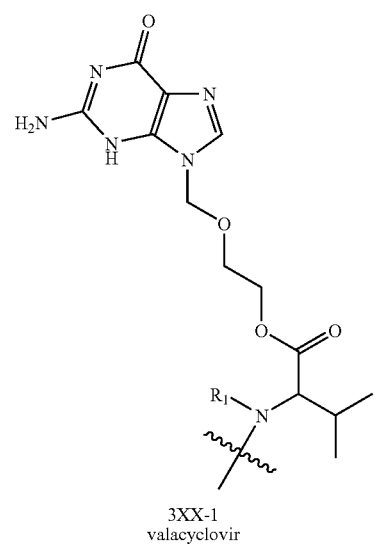
3XX-1
valacyclovir
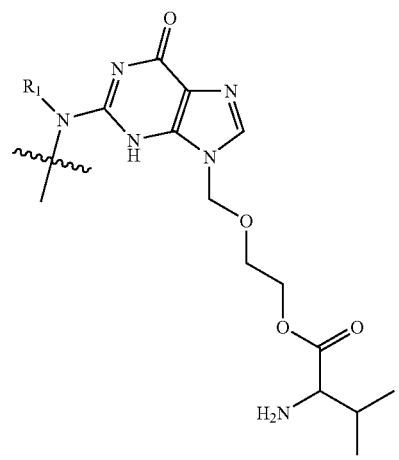
3XX-2
valacyclovir TABLE 1-continued
Formula for Q
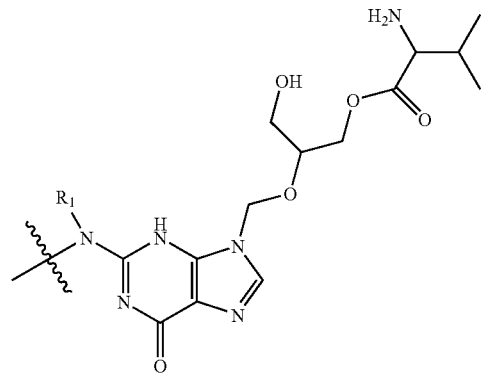
3YY-1
valganciclovir
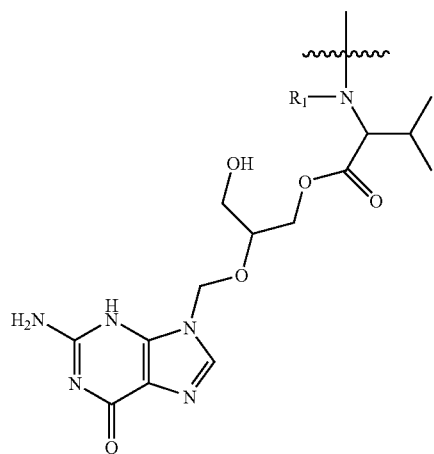
3YY-2
valganciclovir
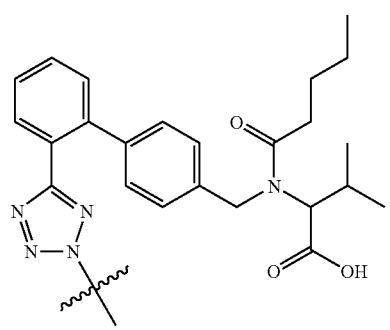
3ZZ-1
valsartan TABLE 1-continued Formula for Q

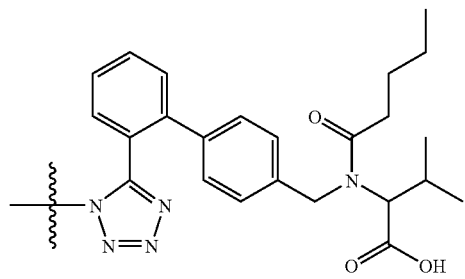

3ZZ-2
valsartan

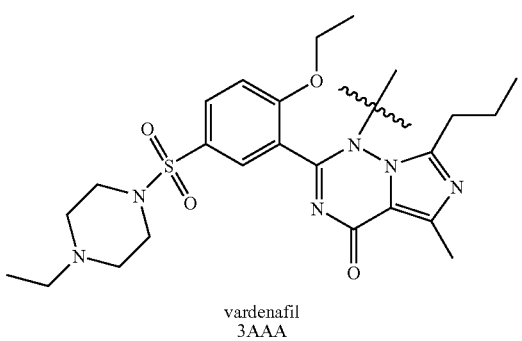

vardenafil
3AAA

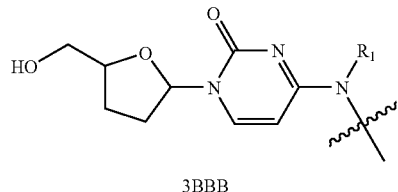

3BBB
zalcitabine

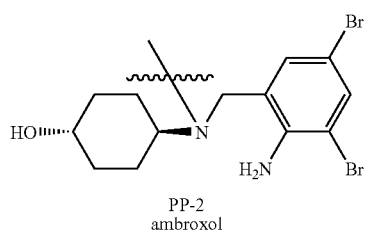

PP-2
ambroxol

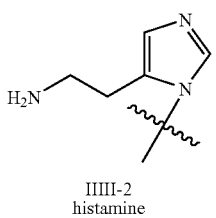

IIIII-2
histamine

In particular, a compound of the invention inhibits a cholinesterase by competing with a natural compound (e.g., acetylcholine (ACh) or butyrylcholine (BuCh)) that binds to the cholinesterase.

The cholinesterase enzyme is inhibited when it is prevented from inactivating a natural compound, such as the neurotransmitter ACh, to any degree that cholinesterase would act on the neurotransmitter in the absence of the compound. As shown in FIG. 1, the compound binds to the cholinesterase to form a carbamoylated enzyme. Hydrolysis of the carbamoylated enzyme is much slower than that of, for example, an acetylated enzyme, which is formed by hydrolysis of its endogenous substrate acetylcholine. Inhibition of the cholinesterase by a compound of the invention ceases when the carbamoylated enzyme is hydrolyzed. Upon hydrolysis of the carbamoylated enzyme, a released compound, such as an amine e.g., Q-H, becomes at least a component of a pharmacologically active agent. In one embodiment, Q-His a salt.

Hydrolysis of the compounds of the invention, which thereby releases at least a component of a pharmacologically active agent, can be hydrolysis by an enzyme (e.g., a cholinesterase) or hydrolysis by other than an enzyme, such as by an acid (e.g., gastric acid).

The phrase "upon hydrolysis by reaction with an enzyme," as used herein, refers to the two-step process of reaction of the compound of the invention with an enzyme to form a carbamoylated enzyme, and decomposition of the carbamoylated enzyme by reaction with $H_2O$.

Likewise, the phrase "upon hydrolysis by reaction with the cholinesterase," as used herein, refers to the two-step process of reaction of the compound of the invention with the enzyme cholinesterase, to form a carbamoylated enzyme, and decomposition of the carbamoylated enzyme by reaction with $H_2O$.

The cholinesterase inhibited by the compound of the invention can be, for example, at least one member selected from the group consisting of an acetylcholinesterase (AChE) or a butyrylcholinesterase (BuChE). The compound of the invention can inhibit AChE alone, BuChE alone, or can inhibit both AChE and BuChE to similar or different degrees.

AChE is located on excitable membranes and inactivates ACh. The excitable membrane can be a presynaptic neuron or a postsynaptic neuron. AChE is also referred to as specific cholinesterase. BuChE is located on excitable membranes and non-neuronal tissue such as blood cells. BuChE is also referred to as pseudocholinesterase or nonspecific cholinesterase. AChE and BuChE are regulators of cholinergic neurotransmission in the central nervous system (brain and spinal cord), peripheral nervous system and autonomic nervous system (parasympathetic nervous system and sympathetic nervous system).

Upon hydrolysis of the carbamate bond of the compound of the invention, a released compound, such as a compound that includes an amine Q-H, becomes at least a component of a pharmacologically active agent. The term "becomes at least a component of a pharmacologically active agent," as used herein, refers to the release of a compound, such as an amine-containing compound Q-H, as a consequence of hydrolysis of the carbamoylated enzyme. The compound Q-H released by hydrolysis of the carbamoylated enzyme is at least a portion of a pharmacologically active agent. In one embodiment, the compound released by the hydrolysis of the carbamoylated enzyme is a prodrug. The term "prodrug," as used herein, refers to a compound that is administered, but is not the actual drug desired in the treatment regimen and is transformed by metabolic processes to the actual drug desired in the treatment. The prodrug then can be modified to release a pharmacologically active agent. In another embodiment, the compound Q-H released by hydrolysis of the carbamoylated enzyme can, itself, be the pharmacologically active agent. Thus, a compound of the invention has a dual role as an inhibitor of a cholinesterase and as a delivery vehicle for a pharmacologically active agent Q-H.

Hydrolysis of the compound of the invention, resulting in the release of a pharmacologically active agent Q-H is shown by the schemes detailed below:

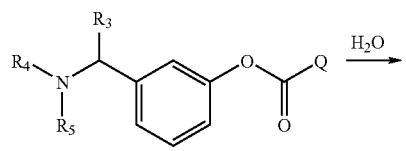

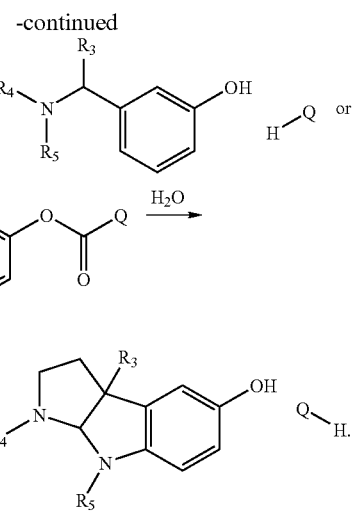

The term "pharmacologically active agent," as used herein, refers to a compound, QH, that influences biological processes by altering the activity, localization and/or expression of molecules (e.g., neurotransmitters, peptides, proteins) which are directly or indirectly involved in the biological processes. For example, the pharmacologically active agent, QH, is a CNS active compound, or a compound for cardiovascular therapy, or an antibacterial.

For example, the CNS active compound is a compound that is known or thought to be useful for treating Alzheimer's disease, Parkinson's disease, attention deficit hyperactivity disorder (ADHD), depression, obsessive compulsive disorders (OCD), anxiety disorders, stress urinary incontinence, chronic pain, or narcolepsy.

For example, the CNS active compound of the invention is an MAO-B inhibitor, e.g., tranylcypromine; a norepinephrine reuptake inhibitor, e.g., atomoxetine, desipramine, nortriptyline, protriptyline, and amoxapine; a selective serotonin reuptake inhibitor (SSRI), e.g., fluvoxamine, and paroxetine; and a dual norepinephrine/serotonin reuptake inhibitor, such as, e.g., duloxetine.

In addition, pharmacologically active agents such as, but not limited to, betahistine, amlodipine, rimantadine, desloratidine, memantine, pregabalin, baclofen, amantadine, or ciprofloxacin can be used according to the present invention. Such agents can be used to treat or prevent Meniere's disease, hypertension, viral infection, allergies, Alzheimer's disease, neuropathic pain, spasticity, Parkinson's disease, or bacterial infection.

The pharmacologically active agent, Q-H, can be a prodrug or precursor that metabolizes into a compound that contains a primary or secondary amine of a pharmacologically active agent.

The pharmacologically active agent preferably alters biological processes in a manner which results in a desirable effect, for example, to improve biological processes, alleviate impairments or disease symptoms, or to slow and/or reverse disease progression. For example, upon hydrolysis of the compound of the invention, the released amine can become at least a component of a pharmacologically active agent that increases the amount of a neurotransmitter in a synapse by diminishing or halting the breakdown of a neurotransmitter, by participating in cellular events that result in the release of additional neurotransmitters, by inhibiting the re-uptake of a neurotransmitter, and/or by increased synthesis of a neurotransmitter.

The pharmacologically active agent can, for example, result in an increase in ACh in the synapse of central nervous system neurons which can compensate for the cholinergic deficiency, for example, in Alzheimer's patients, thereby promoting neuronal transmission to ultimately alleviate or ameliorate the symptoms of Alzheimer's disease. Alzheimer's disease is accompanied by symptoms that include cognitive impairment, disoriented behavior, alter personality, difficulty speaking and comprehending and impaired gait and movement. It has been suggested that decreased cholinergic function is responsible for the symptoms of Alzheimer's disease (Benzi, G., et al., European J. Pharmacol. 346:1-13 (1998); Korczyn, A. D., Exp. Opin. Invest. Drugs 9:2259-2267 (2000)).

The decrease in cholinergic function can be a decrease in the amount of ACh synthesized or released, the inability of a neuron to respond to ACh or inactivation of AChE. In Alzheimer's disease, current treatments include the administration of compounds which increase cholinergic signaling (Jann, M. W., Pharmacotherapy 20:1-12 (2000); Bachurin, S. O., Med. Res. Rev. 23:48-88 (2003)). However, these compounds have modest efficacy, low response rate (typically about 30%-50%) and numerous side effects such as nausea, gastrointestinal problems and fatigue. In one embodiment, the compound of the invention inhibit AChE and, upon hydrolysis, become at least a component of a pharmacologically active agent that increases neurotransmitters, such as ACh, in the synapse of the central nervous system neurons. Thus, for example, the compounds of the invention inhibit AChE, which degrades ACh in the synapses of neurons in Alzheimer's patients, and release pharmacologically active agents, which, collectively or individually, increase neurotransmitters in the synapses.

Cholinergic deficiencies also characterize other disorders such as Parkinson's disease, progressive supranuclear palsy, vascular dementia and Down's syndrome (Korczyn, A. D., Exp. Opin. Invest. Drugs 9:2259-2267 (2000)). Thus, the compound of the invention can also be employed to increase the ACh in these disorders.

Likewise, the pharmacologically active agent can result in an increase in the neurotransmitter dopamine in the central nervous system of patients with Parkinson's disease, thereby promoting neuronal transmission to thereby diminish the symptoms of Parkinson's disease. The increase in dopamine can be an indirect result of hydrolysis of the carbamoylated enzyme to deliver a pharmacologically active agent which results in an increase in dopamine in synapses by, for example, inhibiting the re-uptake of dopamine, preventing the breakdown of dopamine, increasing the release of dopamine or being a precursor (e.g., L-DOPA) in the synthesis of dopamine.

Thus, the pharmacologically active agent can be a central nervous system-type (brain, spinal cord) pharmacologically active agent. The term "central nervous system-type," as used herein, refers to a pharmacologically active agent that has an effect in the central nervous system.

The pharmacologically active agent can also be a peripheral nervous system-type pharmacologically active agent or an autonomic nervous system-type (parasympathetic nervous system and sympathetic nervous system) pharmacologically active agent. The terms "peripheral nervous system-type" and "autonomic nervous system-type," as used herein, refers to a pharmacologically active agent, Q-H, that has an effect in the peripheral nervous system and the autonomic nervous system, respectively.

The pharmacologically active agent can include a prodrug and other structural (e.g., isomers or stereoisomers, such as d, l, dl, R, S, and RS stereoisomers) and functional derivatives thereof in which, preferably, a primary or secondary amine is available for substitution. More specifically, the pharmacologically active agent can also include, for example, salts, hydrates, solvates, zwitterions, and other forms thereof.

In one embodiment, the compound of the invention is

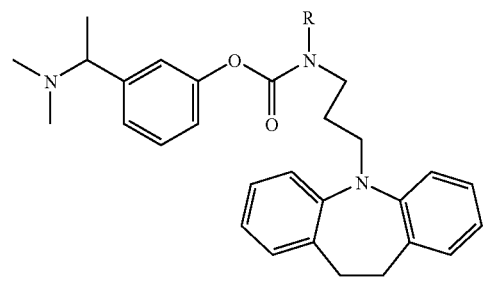

in which R is hydrogen, an unsubstituted alkyl, a substituted alkyl, an unsubstituted aralkyl, a substituted aralkyl, an unsubstituted heteroalkyl, or a substituted heteroalkyl. In one embodiment, R is hydrogen.

In another embodiment, the compound of the invention is

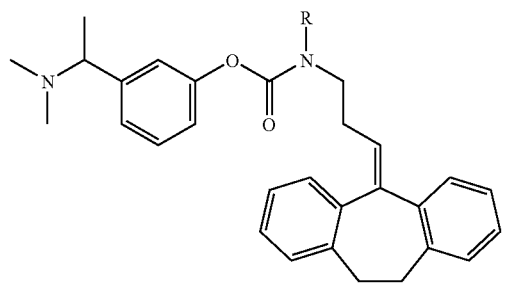

in which R is hydrogen, an unsubstituted alkyl, a substituted alkyl, an unsubstituted aralkyl, a substituted aralkyl, an unsubstituted heteroalkyl, or a substituted heteroalkyl. In one embodiment, R is hydrogen.

In another embodiment, the compound of the invention is

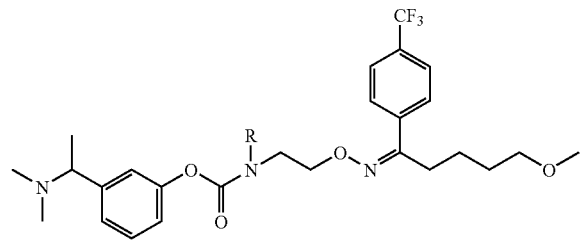

in which R is hydrogen, an unsubstituted alkyl, a substituted alkyl, an unsubstituted aralkyl, a substituted aralkyl, an unsubstituted heteroalkyl, or a substituted heteroalkyl. In one embodiment, R is hydrogen.

In another embodiment, the compound of the invention is

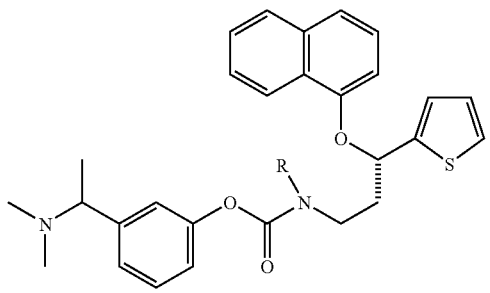

in which R is hydrogen, an unsubstituted alkyl, a substituted alkyl, an unsubstituted aralkyl, a substituted aralkyl, an unsubstituted heteroalkyl, or a substituted heteroalkyl. In one embodiment, R is alkyl.

In another embodiment, the compound of the invention is

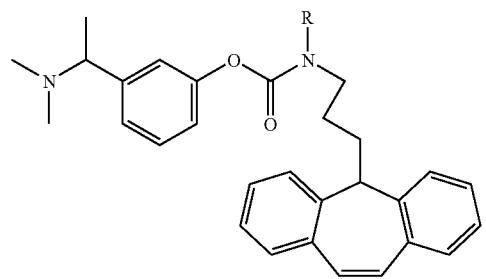

in which R is hydrogen, an unsubstituted alkyl, a substituted alkyl, an unsubstituted aralkyl, a substituted aralkyl, an unsubstituted heteroalkyl, or a substituted heteroalkyl. In another embodiment, R is methyl.

In another embodiment, the compound of the invention is

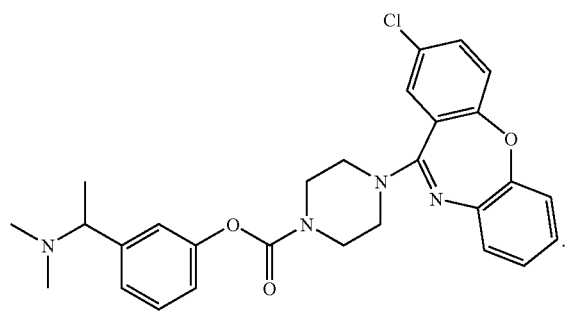

In another embodiment, the compound of the invention is a rivastigmine derivative.

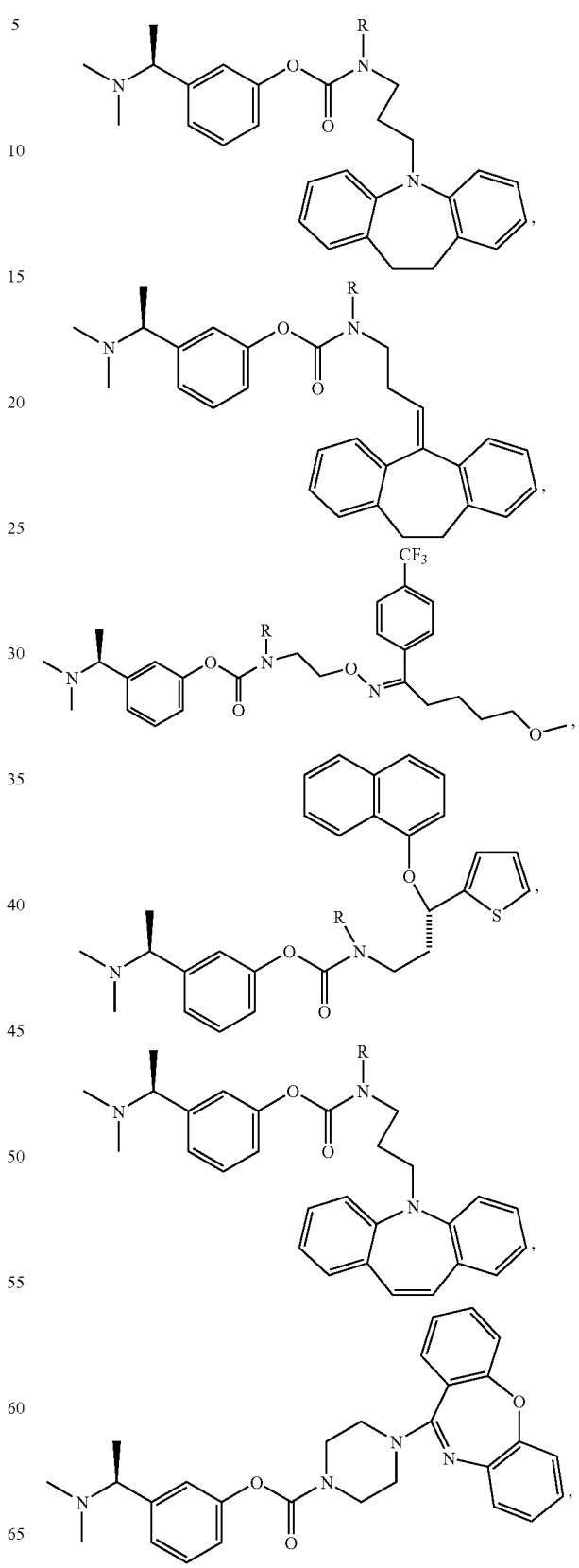

177
-continued
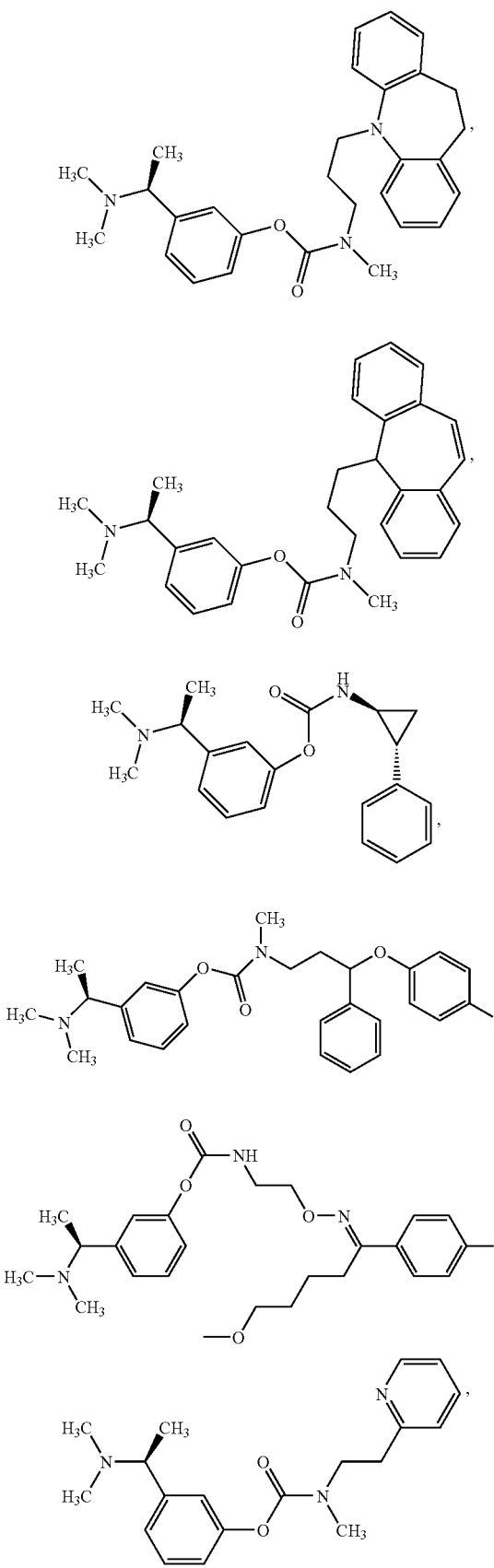
178
-continued
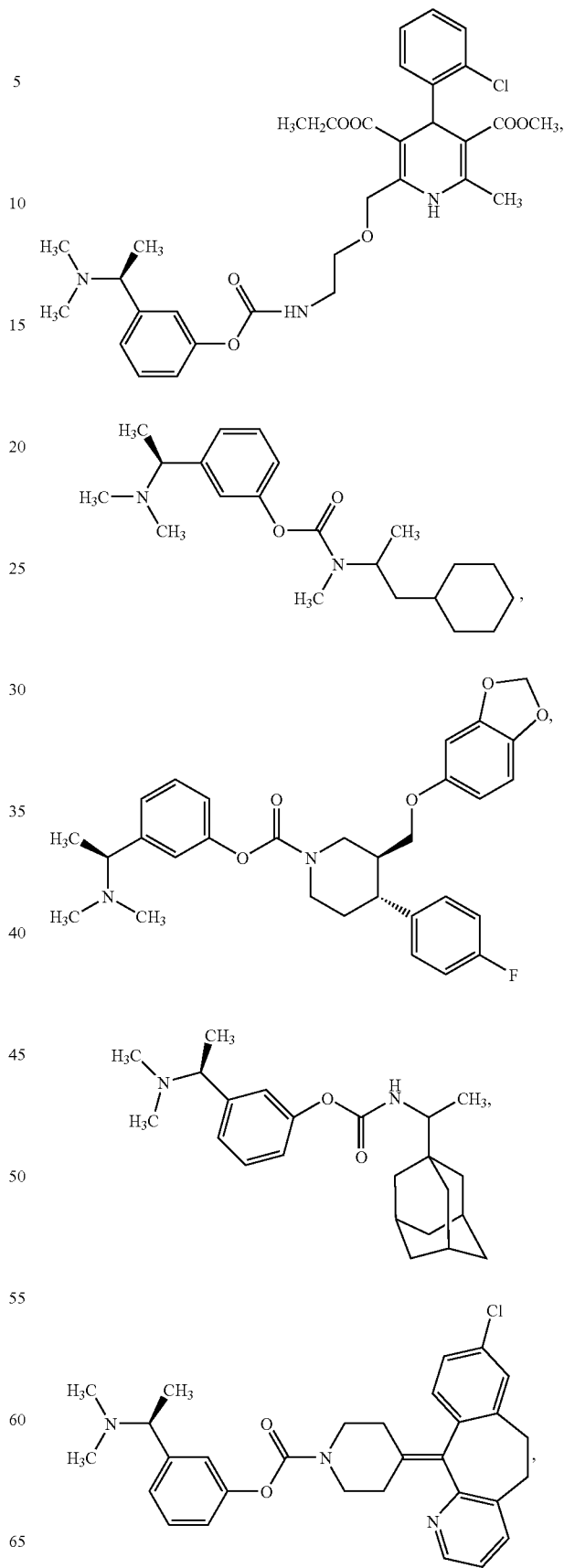

-continued

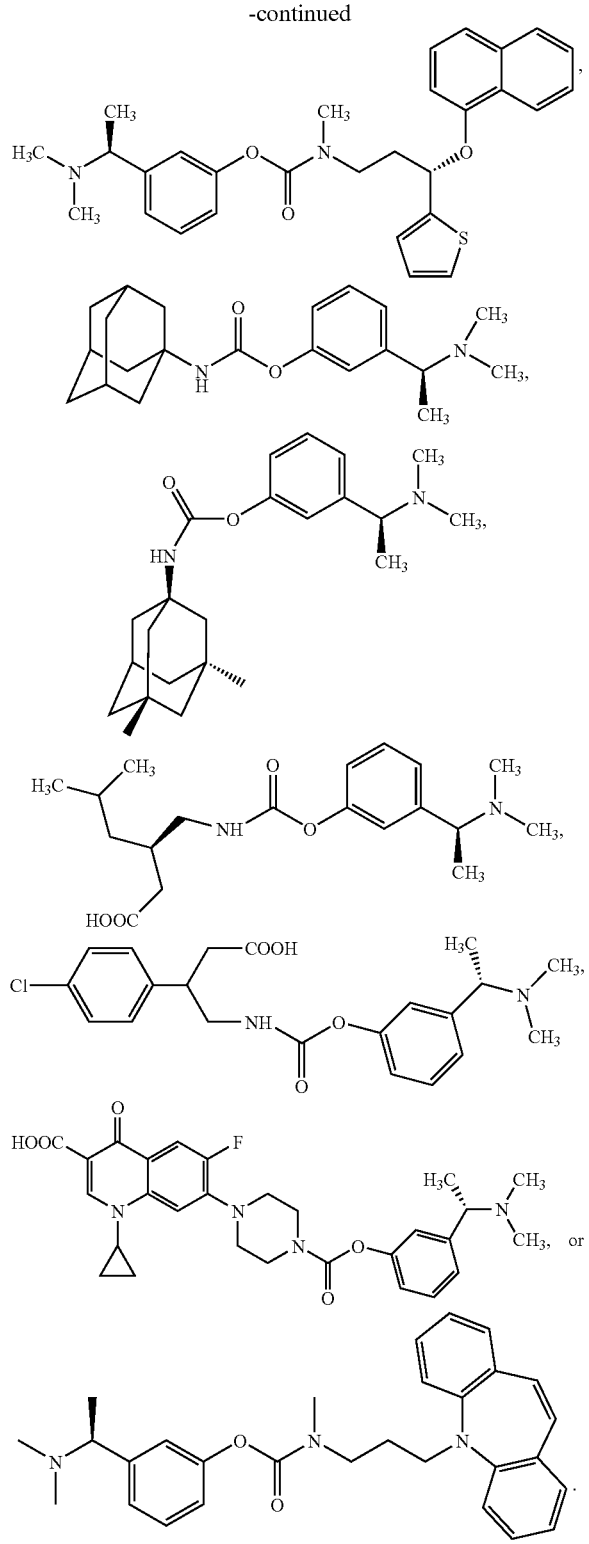

In another embodiment, the compound of the invention is a physostigmine derivative e.g., The term "alkyl," used alone or as part of a larger moiety, includes both straight, branched, or cyclic saturated hydrocarbon chains containing one to twelve carbon atoms.

The term "heteroalkyl," as used herein, is an alkyl group in which one or more carbon atoms is replaced by a heteroatom.

The term "aryl," used alone or as part of a larger moiety as in "aralkyl" or "aralkoxy," are carbocyclic aromatic ring systems (e.g. phenyl), fused polycyclic aromatic ring systems (e.g., naphthyl and anthracenyl) and aromatic ring systems fused to carbocyclic non-aromatic ring systems (e.g., 1,2,3,4-tetrahydronaphthyl and indanyl) having five to about fourteen carbon atoms.

The term "heteroaryl," used alone or as part of a larger moiety as in "heteroaralkyl" or "heteroarylalkoxy," refers to aromatic ring system having five to fourteen members and having at least one heteroatom. Preferably a heteroaryl has from one to about four heteroatoms. Preferred heteroalkyls are those wherein the heteroatom is selected from the groups consisting of oxygen, sulfur, nitrogen, and phosphorous. Examples of heteroaryl rings include pyrazolyl, furanyl, imidazolyl, isoxazolyl, oxadiazolyl, oxazolyl, pyrrolyl, pyridyl, pyrimidinyl, purinyl, pyridazinyl, pyrazinyl, thiazolyl, thiadiazolyl, isothiazolyl, triazolyl, thienyl, 4,6-dihydro-thieno[3,4-c]pyrazolyl, 5,5-dioxide-4,6-dihydrothieno[3,4-c]pyrazolyl, thianaphthenyl, 1,4,5,6,-tetrahydrocyclopentapyrazolyl, carbazolyl, benzimidazolyl, benzothienyl, benzofuranyl, indolyl, azaindolyl, indazolyl, quinolinyl, benzotriazolyl, benzothiazolyl, benzothiadiazolyl, benzooxazolyl, benzimidazolyl, isoquinolinyl, isoindolyl, acridinyl, and benzoisazolyl. Preferred heteroaryl groups are pyrazolyl, furanyl, pyridyl, quinolinyl, indolyl and imidazolyl.

An aralkyl group, as used herein, is an aryl substituent that is linked to a compound by a straight chain or branched alkyl group having from one to twelve carbon atoms.

An heterocycloalkyl group, as used herein, is a heterocycle substituent that is linked to a compound by a straight chain or branched alkyl group having from one to twelve carbon atoms.

An heteroaralkyl group, as used herein, is a heteroaryl substituent that is linked to a compound by a straight chain or branched alkyl group having from one to twelve carbon atoms.

An aryl (including aralkyl, aralkoxy and the like) or heteroaryl (including heteroaralkyl and heteroaralkoxy and the like) may contain one or more substituents. Examples of suitable substituents include aliphatic groups, aryl groups, haloalkoxy groups, heteroaryl groups, halo and hydroxy.

In one embodiment, the compound of the invention includes an isomer or stereoisomer (e.g., d, l, dl, R, S, or RS). In all structures shown herein, it is to be understood that, whether a compound is represented as (+, −), dl (DL) or (R)(S), the invention is intended to include racemic mixtures, or pure compositions of one form of the compound, e.g. "d" or "l," "R" or "S," unless otherwise specified.

Methods to prepare the compounds of the invention are within the knowledge of one skilled in the art (see, for example, U.S. Pat. Nos. 5,665,880; 5,677,457; and WO 97/14694, the teachings of which are hereby incorporated by reference in their entirety).

In one embodiment, synthesis of compounds of the invention can be accomplished by activation of an amine group of a compound to form an activated amine. The activated amine can be isolated and reacted with a phenol group of another compound to form the compound of the invention. For example, a primary amine can be converted into an isocyanate. Alternatively, amines can be converted into carbamoyl chlorides. Amines can also be activated and used in situ for the formation of the compound of the invention, such as by reacting an amine with activating agents that contain carbonyl chlorides (e.g. phosgene, triphosgene), by reacting the amine with activating agents that contain nitrophenyloxycarbonyl groups (e.g. bis-4-nitophenylcarbonate, 4-nitrophenylchloroformate), or by reacting the amine with carbonyldiimidazole. The individual steps of amine activation and formation of the compounds of the invention can be catalyzed by a variety of agents, such as acids, bases, and nucleophiles, separately or in combination.

In another embodiment, synthesis of the compounds of the invention can be accomplished by activation of a phenol group of a compound to form an activated phenol. The activated phenol is reacted with an amine group of another compound. Activation of the phenol can be performed in a variety of ways, such as by reacting the phenol with activating agents that contain carbonyl chlorides (e.g., phosgene, triphosgene), by reacting the phenol with activating agents that contain nitrophenyloxycarbonyl groups (e.g., bis-4-nitrophenylcarbonate, 4-nitrophenylchloroformate), or by reacting the phenol with carbonyldiimidazole. The individual steps of phenol activation and formation of the compound of the invention can be catalyzed by a variety of agents, such as acids, bases, and nucleophiles, separately or in combination.

The compounds of the invention can be analyzed by well-known analytical methods, including NMR.

The compounds of the invention can be synthesized by known methods, for example: compounds of the invention can be synthesized, for example, by reaction of a phenolic hydroxyl group with carbonyldiimidazole (CDI) in ethylacetate followed by addition of acetic acid and the amine to form of the aromatic carbamoyl ester (Gao et al., J. Heterocyclic Chem 37:331-333 (2000), the teachings of which are hereby incorporated by reference in their entirety).

Formation of aromatic carbomoyl esters from eseroline has been described using carbamoyl chlorides (Marta, et al., Bichimica et Biophysica Acta 1120:262-266 (1992); Marta, et al., Biomed Biochem Acta 47:285-288 (1998); Marta, et al., Life Sci. 43:1921-1928 (1988), the teachings of each are hereby incorporated by reference in their entireties).

Reaction of a phenolic hydroxyl group with carbamoyl chlorides has also been described for the synthesis of aromatic carbamoyl esters (Toda, et al., Bioorg Med Chem 11:1935-1955 (2003), Kogen, et al., Org Lett 4:3359-3362 (2002), Mustazza, et al., Eur J. Med Chem 37:91-109 (2002) and Sterling, et al., J Med Chem 45:5260-5279 (2002), the teachings of each are hereby incorporated by reference in their entireties).

Phenserine and its analogs have been prepared by reaction of eseroline with an isocyanate (U.S. Pat. No. 6,495,700, the teachings of which are hereby incorporated by reference in their entirety), by reaction in dimethoxyethane under an argon atmosphere in the presence of catalytic amounts of n-butyllithium in hexanes.

Isocyanates were also employed by Mustazza, et al., Eur J Med Chem 37:91-109 (2002) and Yuv et al., J Med Chem 44:4062-4071 (2001), the teachings of all of which are hereby incorporated by reference in their entireties.

In a further embodiment, the compound of the invention is a compound of formula III:

(III)

or a pharmaceutically acceptable salt thereof, wherein Q is as described in formula I.

In another embodiment, the compound of the invention is a compound of formula IV:

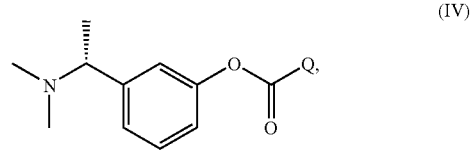

(IV)

or a pharmaceutically acceptable salt thereof, wherein Q is as described in formula I.

In another, the compound of the invention is a compound of formula (VI):

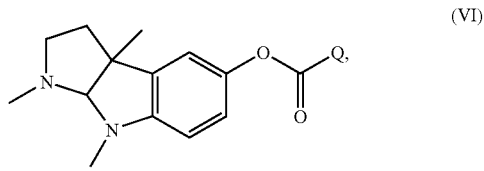

(VI)

or a pharmaceutically acceptable salt thereof, wherein Q is described in formula II.

In one embodiment, the pharmacologically active agent, QH, is a memory-facilitating agent. In another embodiment, the pharmacologically active agent, QH, is a cognition-facilitating agent.

The term "memory-facilitating agent," as used herein, refers to a compound that promotes memory in an individual, prevents or minimizes a decline in memory in an individual or participates in biological processes which are involved in memory function.

The memory processes which can be facilitated by the memory-facilitating agent can be memory consolidation, the process of storing new information in long term memory ("Neuroscience: Exploring The Brain," Bear, M. F. et al., Williams & Wilkins, Baltimore, Md., Ch. 19, pp. 517-545 (1996); McGaugh, J. L. Science 287: 248-251 (2000), the teachings of which are hereby incorporated by reference in their entirety); short-term memory (also referred to as "working memory"), the process whereby newly acquired information is maintained for short periods of time and the newly acquired information is made available for further information processing ("Neuroscience: Exploring The Brain," Bear, M. F. et al., Williams & Wilkins, Baltimore, Md., Ch. 19, pp. 517-545 (1996); McGaugh, J. L. Science 287: 248-251 (2000); Becker, J. T., et al., Brain and Cognition 41:1-8 (1999), the teachings of which are hereby incorporated by reference in their entirety); declarative memory, which is the memory of facts and events ("Neuroscience: Exploring The Brain," Bear, M. F. et al., Williams & Wilkins, Baltimore, Md., Ch. 19, pp. 517-545 (1996); McGaugh, J. L. Science 287: 248-251 (2000); Tulving, E., et al., Science 247: 301-306 (1990); Squire, L. R., et al., Proc. Natl. Acad. Sci. 93: 13515-13522 (1996), the teachings of which are hereby incorporated by reference in their entirety); procedural memory (also referred to as "tacit knowledge" or "implicit knowledge"), which is the memory for skills or behavior ("Neuroscience: Exploring The Brain," Bear, M. F. et al., Williams & Wilkins, Baltimore, Md., Ch. 19, pp. 517-545 (1996); McGaugh, J. L. Science 287: 248-251 (2000), the teachings of which are hereby incorporated by reference in their entirety); or attention, acquisition, retrieval or retention.

In another embodiment, the pharmacologically active agent, QH, is a cognition-facilitating agent. The term "cognition-facilitating agent," as used herein, refers to a compound that promotes activities associated with thinking, learning and acquiring knowledge in an individual, prevents or minimizes a decline in thinking, learning and acquiring knowledge in an individual or participates in biological processes which are involved in thinking, learning and acquiring knowledge. The decline in thinking, learning and acquired knowledge (a cognitive disorder) can be a consequence of or associated with another disease (e.g., Alzheimer's disease) or condition of the central, or peripheral or autonomic nervous system. The cognitive process that can be facilitated by the cognition-facilitating agent can be assessed by behavioral criteria and behavioral assays which, in turn, can further define where, in the learning, thinking, and acquiring knowledge process, the cognition-facilitating agents are acting. One of skill in the art would be capable of identifying and evaluating agents that would be suitable as cognition-facilitating agents.

In compounds of formula I, II, III, IV, V, and VI, the substructure Q can represent any amine-containing pharmacologically active agent, e.g., atomoxetine, desipramine, nortriptyline, fluvoxamine, duloxetine, protriptyline, amoxapine, tranylcypromine, paroxetine, betahistine, amlodipine, propylhexedrine, rimantadine, desloratadine, clozapine, dorzolamide, hydrochlorothiazide, lisinopril, lomefloxacin, melphalan, nepafenac, pregabalin, riluzole, valcyclovir, ambroxol, aminoglutethimide, amoxicillin, ampicillin, aminone, baclofen, benazepril, bupropion, ciprofloxacin, dapsone, diclofenac, enoxacin, ethambutol, gabapentin, methoxamine, midodrine, methylphenidate, norepinephrine, pseudoephedrine, ramipril, sertraline, frovatriptan, cinacalcet, benzoctamine, isometheptene, methoxyphenamine, amantadine, memantine, metoclopramide, aminocaproic acid, afloqualone, aminohippuric acid, aminosalicylic acid, amodiaquine, amsacrine, anileridine, atabrine, benzocaine, bumetanide, buthiazide, carbutamide, carvedilol, cefaclor, cefadroxil, cefroxadine, cephradine, chlordiazepoxide, chloroprocaine, clortermine, cyclacillin, cyclopenthiazide, cycloserine, cysteamine, dezocine, dobutamine, eflornithine, ephedrine, epinephrine, epirubicin, etilefrine, fenfluramine, flucytosine, flufenamic acid, furosemide, glutamic acid, glutamine, glutathione, glycine, histamine, hydralazine, hydroflumethiazide, idarubicin, imipenem, iopanoic acid, isocaine, isoproterenol, isoxsuprine, ketamine, lamivudine, lamotrigine, levodopa, lofexidine, mecamylamine, mefenamic acid, mephentermine, metaraminol, methyldopa, metyrosine, neomycin A, niflumic acid, nimodipine, nomifensine, nylidrin, oxamniquine, oxyfedrine, perhexyline, phenmetrazine, phenylpropanolamine, pipemidic acid, piperazine, pipradrol, pramipexole, primaquine, procainamide, procarbazine, pyrimethamine, quinethazone, sisomicin, sparfloxacin, spectinomycin, sulfacytine, sulfadimethoxine, sulfadoxine, sulfaguanidine, sulfaguanole, sulfamethoxypyridazine, sulfameter, sulfamerazine, sulfamethazine, sulfamethizole, sulfamethomidine, sulfamoxole, sulfisoxazole, sulfisoxazole acetal, sulfonamide CS61, tamsulosin, thiamphenicol glycinate, timonacic, tinoridine, tizanidine, tolazoline, tretoquinol, triamterene, trichlormethiazide, trientine, trimethoprim, trimetrexate, tromethamine, troxipide, tryptophan, zalcitibine, alendronic acid, alanine, arginine, asparagine, aspartic acid, cysteine, glutamic acid, histidine, isoleucine, leucine, lysine, methionine, phenylalanine, proline, serine, threonine, tyrosine, valine, deferoxamine, mesalamine, phentolamine, thiamine, adefovir dipivoxil, adenosine, alatrofloxacin, alendronate, alfuzosin, almotriptan, alosetron, amifostine, levulan, amlexanox, amprenavir, anagrelide, apraclonidine, aprepitant, argatroban, atovaquone, brimonidine, bromfenac, cabergoline, candesartan, carbidopa, cefditoren pivoxil, cidofovir, cisapride, clofarabine, colestipol, conivaptan, cytarabine, deferasirox, delavirdine, dexmedetomidine, dexmethylphenidate, didanosine, migranal, dolasetron, doxazosin, doxorubicin, emtricitabine, enalapril, felodipine, epinastine, erlotinib, ertapenem, omeprazole, etodolac, famciclovir, famotidine, fenoldopam, fomepizole, fosamprenavir, gatifloxacin, ganciclovir, gefitinib, gemcitabine, gemifloxacin, grepafloxacin, imatinib, imiquimod, irbesartan, isradipine, levothyroxine, menotropins, methyl aminolevulinate, metformin, mitoxantrone, moexipril, naratriptan, nelarabine, moxifloxacin, nicardipine, nisoldipine, nizatidine, olanzapine, oseltamivir, olmesartan medoxomil, oxaliplatin, pamidronic acid, pantoprazole, pemetrexed, penciclovir, pergolide, perindopril, propafenone, quinapril, rabeprazole, ranitidine, rizatriptan, sevelamer, sildenafil, sumatriptan, tacrine, tadalafil, tegaserod, tenofovir, terazosin, tigecycline, tirofiban, torsemide, trandolapril, trovafloxacin, valacyclovir, valganciclovir, valsartan, vardenafil, zalcitabine and zolmitriptan.

According to the present invention, a primary or a secondary amine can be covalently bound to a stigmine, such as rivastigmine or physostigmine.

The term "desipramine" means a pharmacologically active agent, wherein Q is represented by the formula P, $R_1$ is methyl, and the structure

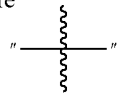

is replaced with H.

The term "nortriptyline" means a pharmacologically active agent, wherein Q is represented by the formula Q', $R_1$ is methyl, and the structure

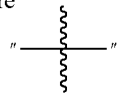

is replaced with H.

The term "fluoxetine" means a pharmacologically active agent, wherein Q is represented by the formula R, $R_1$ is methyl, and the structure

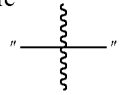

is replaced with H.

The term "fluvoxamine" means a pharmacologically active agent, wherein Q is represented by the formula S, $R_1$ is H, and the structure

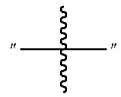

is replaced with H.

The term "duloxetine" means a pharmacologically active agent, wherein Q is represented by the formula T, $R_1$ is methyl, and the structure

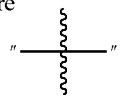

is replaced with H.

The term "protriptyline" means a pharmacologically active agent, wherein Q is represented by the formula U, $R_1$ is methyl, and the structure

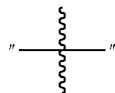

is replaced with H.

The term "amoxapine" means a pharmacologically active agent, wherein Q is represented by the formula V, $R_1$ is absent and the structure

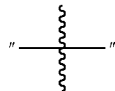

is replaced with H.

The term "tranylcypromine" means a pharmacologically active agent, wherein Q is represented by the formula X, $R_1$ is H, and the structure

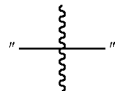

is replaced with H.

The term "paroxetine" means a pharmacologically active agent, wherein Q is represented by the formula Y, $R_1$ is absent, and the structure

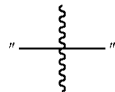

is replaced with H.

The term "betahistine" means a pharmacologically active agent, wherein Q is represented by the formula Z, $R_1$ is methyl and the structure

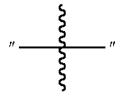

is replaced with H.

The term "amlodipine" means a pharmacologically active agent, wherein Q is represented by the formula AA, $R_1$ is H, and the structure

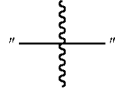

is replaced with H.

The term "propylhexedrine" means a pharmacologically active agent, wherein Q is represented by the formula BB, $R_1$ is methyl, and the structure

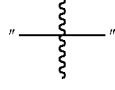

is replaced with H.

The term "rimantadine" means a pharmacologically active agent, wherein Q is represented by the formula CC, $R_1$ is H, and the structure

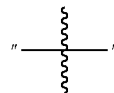

is replaced with H.

The term "desloratadine" means a pharmacologically active agent, wherein Q is represented by the formula DD, $R_1$ is absent, and the structure

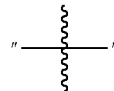

is replaced with H.

The term "aniline" means a pharmacologically active agent, wherein Q is represented by the formula EE, $R_1$ is H, and the structure

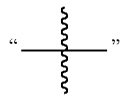

is replaced with H.

The term "clozapine" means a pharmacologically active agent, wherein Q is represented by the formula FF, $R_1$ is absent, and the structure

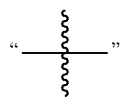

is replaced with H.

The term "dorzolamide" means a pharmacologically active agent, wherein Q is represented by the formula GG, $R_1$ is ethyl, and the structure

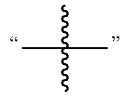

is replaced with H.

The term "hydrochlorothiazide" means a pharmacologically active agent, wherein Q is represented by the formula HH, $R_1$ is absent, and the structure

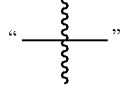

is replaced with H.

The term "lisinopril" means a pharmacologically active agent, wherein Q is represented by the formula II-1 ($R_1$ is H) or II-2 ($R_1$ is absent), and the structure

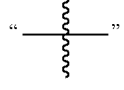

is replaced with H.

The term "lomefloxacin" means a pharmacologically active agent, wherein Q is represented by the formula JJ, $R_1$ is absent, and the structure

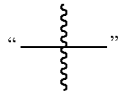

is replaced with H.

The term "melphalan" means a pharmacologically active agent, wherein Q is represented by the formula KK, $R_1$ is H, and the structure

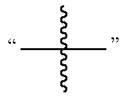

is replaced with H.

The term "nepafenac" means a pharmacologically active agent, wherein Q is represented by the formula LL, $R_1$ is H, and the structure

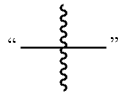

is replaced with H.

The term "pregabalin" means a pharmacologically active agent, wherein Q is represented by the formula MM, $R_1$ is H, and the structure

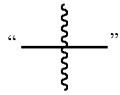

is replaced with H.

The term "riluzole" means a pharmacologically active agent, wherein Q is represented by the formula NN, $R_1$ is H, and the structure

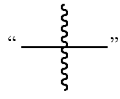

is replaced with H.

The term "valcyclovir" means a pharmacologically active agent, wherein Q is represented by the formula OO-1 and OO-2, $R_1$ is H, and the structure

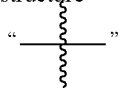

is replaced with H.

The term "ambroxol" means a pharmacologically active agent, wherein Q is represented by the formula PP-1 ($R_1$ is H) or PP-2 ($R_1$ is absent) and the structure

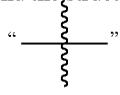

is replaced with H.

The term "aminoglutethimide" means a pharmacologically active agent, wherein Q is represented by the formula QQ, R1 is H, and the structure

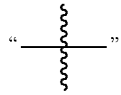

is replaced with H.

The term "amoxicillin" means a pharmacologically active agent, wherein Q is represented by the formula RR, R1 is H, and the structure

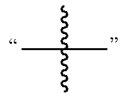

is replaced with H.

The term "ampicillin" means a pharmacologically active agent, wherein Q is represented by the formula SS, R1 is H, and the structure

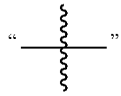

is replaced with H.

The term "aminone" means a pharmacologically active agent, wherein Q is represented by the formula TT, R1 is H, and the structure

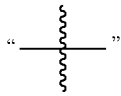

is replaced with H. The term "baclofen" means a pharmacologically active agent, wherein Q is represented by the formula UU, R1 is H, and the structure

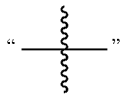

is replaced with H.

The term "benazepril" means a pharmacologically active agent, wherein Q is represented by the formula VV, R1 is absent, and the structure

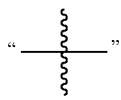

is replaced with H.

The term "bupropion" means a pharmacologically active agent, wherein Q is represented by the formula WW, R1 is absent, and the structure

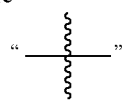

is replaced with H.

The term "ciprofloxacin" means a pharmacologically active agent, wherein Q is represented by the formula XX, $R_1$ is absent, and the structure

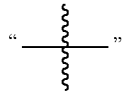

is replaced with H.

The term "dapsone" means a pharmacologically active agent, wherein Q is represented by the formula YY, R1 is H, and the structure

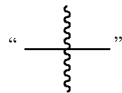

is replaced with H.

The term "diclofenac" means a pharmacologically active agent, wherein Q is represented by the formula ZZ, $R_1$ is absent, and the structure

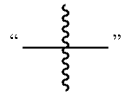

is replaced with H.

The term "enoxacin" means a pharmacologically active agent, wherein Q is represented by the formula AAA, $R_1$ is absent, and the structure

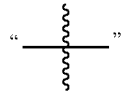

is replaced with H.

The term "ethambutol" means a pharmacologically active agent, wherein Q is represented by the formula BBB, R1 is absent, and the structure

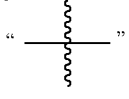

is replaced with H.

The term "gabapentin" means a pharmacologically active agent, wherein Q is represented by the formula CCC, $R_1$ is H, and the structure

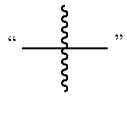

is replaced with H.

The term "methoxamine" means a pharmacologically active agent, wherein Q is represented by the formula DDD, $R_1$ is H, and the structure

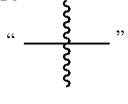

is replaced with H.

The term "midodrine" means a pharmacologically active agent, wherein Q is represented by the formula EEE, $R_1$ is H, and the structure

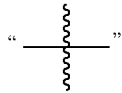

is replaced with H.

The term "methylphenidate" means a pharmacologically active agent, wherein Q is represented by the formula FFF, $R_1$ is absent, and the structure

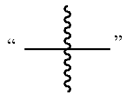

is replaced with H.

The term "norepinephrine" means a pharmacologically active agent, wherein Q is represented by the formula GGG, and the structure

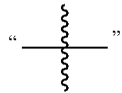

is replaced with H.

The term "pseudoephedrine" means a pharmacologically active agent, wherein Q is represented by the formula HHH, and the structure

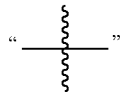

is replaced with H.

The term "ramipril" means a pharmacologically active agent, wherein Q is represented by the formula III, $R_1$ is absent, and the structure

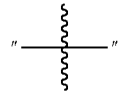

is replaced with H.

The term "sertraline" means a pharmacologically active agent, wherein Q is represented by the formula JJJ, $R_1$ is methyl, and the structure

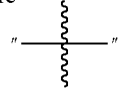

is replaced with H.

The term "frovatriptan" means a pharmacologically active agent, wherein Q is represented by the formula KKK-1 or KKK-2 and the structure

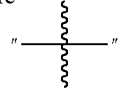

is replaced with H.

The term "cinacalcet" means a pharmacologically active agent, wherein Q is represented by the formula LLL, $R_1$ is absent, and the structure

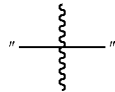

is replaced with H.

The term "benzoctamine" means a pharmacologically active agent, wherein Q is represented by the formula MMM and the structure

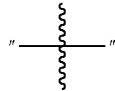

is replaced with H.

The term "hydroxyamphetamide" means a pharmacologically active agent, wherein Q is represented by the formula NNN, $R_1$ is H, and the structure

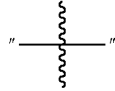

is replaced with H.

The term "isometheptene" means a pharmacologically active agent, wherein Q is represented by the formula OOO, $R_1$ is methyl, and the structure

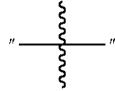

is replaced with H.

The term "methoxyphenamine" means a pharmacologically active agent, wherein Q is represented by the formula PPP, $R_1$ is methyl, and the structure

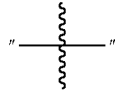

is replaced with H.

The term "dopamine" means a pharmacologically active agent, wherein Q is represented by the formula QQQ, $R_1$ is H, and the structure

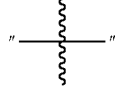

is replaced with H.

The term "amantadine" means a pharmacologically active agent, wherein Q is represented by the formula SSS, $R_1$ is H, and the structure

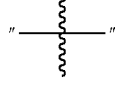

is replaced with H.

The term "memantine" means a pharmacologically active agent, wherein Q is represented by the formula TTT, $R_1$ is H, and the structure

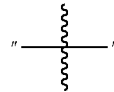

is replaced with H.

The term "metoclopramide" means a pharmacologically active agent, wherein Q is represented by the formula UUU, $R_1$ is H, and the structure

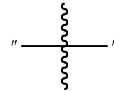

is replaced with H.

The term "aminocaproic acid" means a pharmacologically active agent, wherein Q is represented by the formula VVV, $R_1$ is H, and the structure

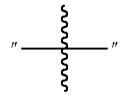

is replaced with H.

The term "afloqualone" means a pharmacologically active agent, wherein Q is represented by the formula WWW, $R_1$ is H, and the structure

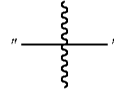

is replaced with H.

The term "aminohippuric acid" means a pharmacologically active agent, wherein Q is represented by the formula XXX, $R_1$ is H, and the structure

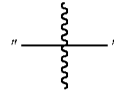

is replaced with H.

The term "aminosalicylic acid" means a pharmacologically active agent, wherein Q is represented by the formula YYY, $R_1$ is H, and the structure

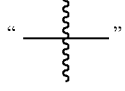

is replaced with H.

The term "amodiaquine" means a pharmacologically active agent, wherein Q is represented by the formula ZZZ, $R_1$ is absent, and the structure

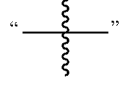

is replaced with H.

The term "amsacrine" means a pharmacologically active agent, wherein Q is represented by the formula AAAA, $R_1$ is absent, and the structure

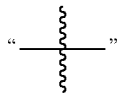

is replaced with H.

The term "anileridine" means a pharmacologically active agent, wherein Q is represented by the formula BBBB, $R_1$ is H, and the structure

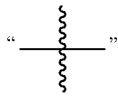

is replaced with H.

The term "atabrine" means a pharmacologically active agent, wherein Q is represented by the formula CCCC, $R_1$ is absent, and the structure

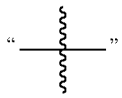

is replaced with H.

The term "benzocaine" means a pharmacologically active agent, wherein Q is represented by the formula DDDD, $R_1$ is H, and the structure

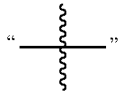

is replaced with H.

The term "bumetanide" means a pharmacologically active agent, wherein Q is represented by the formula EEEE, $R_1$ is butyl, and the structure

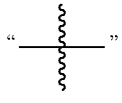

is replaced with H.

The term "buthiazide" means a pharmacologically active agent, wherein Q is represented by the formula FFFF, $R_1$ is absent, and the structure

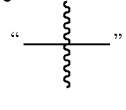

is replaced with H.

The term "carbutamide" means a pharmacologically active agent, wherein Q is represented by the formula GGGG, $R_1$ is H, and the structure

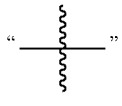

is replaced with H.

The term "carvedilol" means a pharmacologically active agent, wherein Q is represented by the formula HHHH-1 or HHHH-2, $R_1$ is absent, and the structure

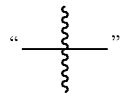

is replaced with H.

The term "cefaclor" means a pharmacologically active agent, wherein Q is represented by the formula $III_1$, $R_1$ is H, and the structure

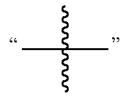

is replaced with H.

The term "cefadroxil" means a pharmacologically active agent, wherein Q is represented by the formula JJJJ, $R_1$ is H, and the structure

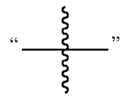

is replaced with H.

The term "cefroxadine" means a pharmacologically active agent, wherein Q is represented by the formula KKKK, $R_1$ is H, and the structure

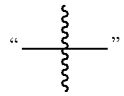

is replaced with H.

The term "cephradine" means a pharmacologically active agent, wherein Q is represented by the formula LLLL, $R_1$ is H, and the structure

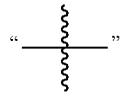

is replaced with H.

The term "chlordiazepoxide" means a pharmacologically active agent, wherein Q is represented by the formula MMMM, $R_1$ is methyl, and the structure

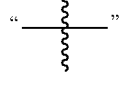

is replaced with H.

The term "chloroprocaine" means a pharmacologically active agent, wherein Q is represented by the formula NNNN, $R_1$ is H, and the structure

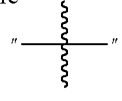

is replaced with H.

The term "clortermine" means a pharmacologically active agent, wherein Q is represented by the formula OOOO, $R_1$ is H, and the structure

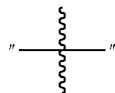

is replaced with H.

The term "cyclacillin" means a pharmacologically active agent, wherein Q is represented by the formula PPPP, $R_1$ is H, and the structure

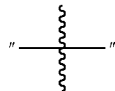

is replaced with H.

The term "cyclopenthiazide" means a pharmacologically active agent, wherein Q is represented by the formula QQQQ, R1 is absent, and the structure

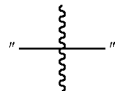

is replaced with H.

The term "cycloserine" means a pharmacologically active agent, wherein Q is represented by the formula RRRR, $R_1$ is H, and the structure

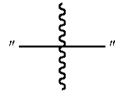

is replaced with H.

The term "cysteamine" means a pharmacologically active agent, wherein Q is represented by the formula SSSS, $R_1$ is H, and the structure

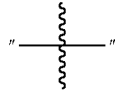

is replaced with H.

The term "dezocine" means a pharmacologically active agent, wherein Q is represented by the formula TTTT, $R_1$ is H, and the structure

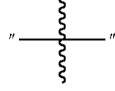

is replaced with H.

The term "dobutamine" means a pharmacologically active agent, wherein Q is represented by the formula UUUU, $R_1$ is absent, and the structure

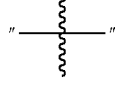

is replaced with H.

The term "eflornithine" means a pharmacologically active agent, wherein Q is represented by the formula VVVV-1 or VVVV-2, $R_1$ is H, and the structure

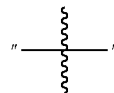

is replaced with H.

The term "ephedrine" means a pharmacologically active agent, wherein Q is represented by the formula WWWW, $R_1$ is methyl, and the structure

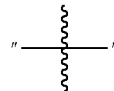

is replaced with H.

The term "epinephrine" means a pharmacologically active agent, wherein Q is represented by the formula XXXX, $R_1$ is methyl, and the structure

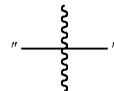

is replaced with H.

The term "epirubicin" means a pharmacologically active agent, wherein Q is represented by the formula YYYY, $R_1$ is H, and the structure

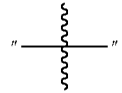

is replaced with H.

The term "etilefrine" means a pharmacologically active agent, wherein Q is represented by the formula ZZZZ, $R_1$ is ethyl, and the structure

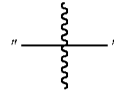

is replaced with H.

The term "fenfluramine" means a pharmacologically active agent, wherein Q is represented by the formula AAAAA, $R_1$ is ethyl, and the structure

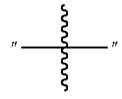

is replaced with H.

The term "flucytosine" means a pharmacologically active agent, wherein Q is represented by the formula BBBBB, $R_1$ is H, and the structure

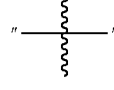

is replaced with H.

The term "flufenamic acid" means a pharmacologically active agent, wherein Q is represented by the formula CCCCC, $R_1$ is absent, and the structure

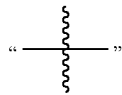

is replaced with H.

The term "furosemide" means a pharmacologically active agent, wherein Q is represented by the formula DDDDD, $R_1$ is absent, and the structure

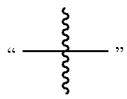

is replaced with H.

The term "glutamic acid" means a pharmacologically active agent, wherein Q is represented by the formula EEEEE, $R_1$ is H, and the structure

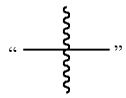

is replaced with H.

The term "glutamine" means a pharmacologically active agent, wherein Q is represented by the formula FFFFF, $R_1$ is H, and the structure

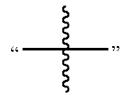

is replaced with H.

The term "glutathione" means a pharmacologically active agent, wherein Q is represented by the formula GGGGG, $R_1$ is H, and the structure

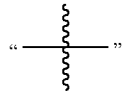

is replaced with H.

The term "glycine" means a pharmacologically active agent, wherein Q is represented by the formula HHHHH, $R_1$ is H, and the structure

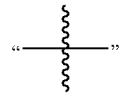

is replaced with H.

The term "histamine" means a pharmacologically active agent, wherein Q is represented by the formula IIIII-1 ($R_1$ is H) or IIIII-2 ($R_1$ is absent), and the structure

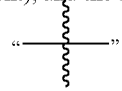

is replaced with H.

The term "hydralazine" means a pharmacologically active agent, wherein Q is represented by the formula JJJJJ-1 ($R_1$ is H) or JJJJJ-2 ($R_1$ is absent), and the structure

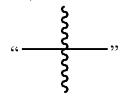

is replaced with H.

The term "hydroflumethiazide" means a pharmacologically active agent, wherein Q is represented by the formula KKKKK $R_1$ is absent, and the structure

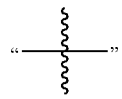

is replaced with H.

The term "idarubicin" means a pharmacologically active agent, wherein Q is represented by the formula LLLLL, $R_1$ is H, and the structure

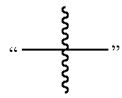

is replaced with H.

The term "imipenem" means a pharmacologically active agent, wherein Q is represented by the formula MMMMM-1 or MMMMM-2, $R_1$ is absent, and the structure

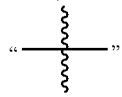

is replaced with H.

The term "iopanoic acid" means a pharmacologically active agent, wherein Q is represented by the formula NNNNN, $R_1$ is H, and the structure

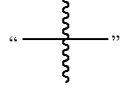

is replaced with H.

The term "isocaine" means a pharmacologically active agent, wherein Q is represented by the formula OOOOO, $R_1$ is H, and the structure

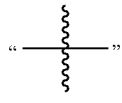

is replaced with H.

The term "isoproterenol" means a pharmacologically active agent, wherein Q is represented by the formula PPPPP, $R_1$ is isopropyl, and the structure

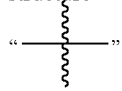

is replaced with H.

The term "isoxsuprine" means means a pharmacologically active agent, wherein Q is represented by the formula QQQQQ, $R_1$ is absent, and the structure $$"-\xi-"$$

is replaced with H.

The term "ketamine" means a pharmacologically active agent, wherein Q is represented by the formula RRRRR, $R_1$ is methyl, and the structure $$"-\xi-"$$

is replaced with H.

The term "lamivudine" means a pharmacologically active agent, wherein Q is represented by the formula SSSSS, $R_1$ is H, and the structure $$"-\xi-"$$

is replaced with H.

The term "lamotrigine" means a pharmacologically active agent, wherein Q is represented by the formula TTTTT-1 or TTTTT-2, $R_1$ is H, and the structure $$"-\xi-"$$

is replaced with H.

The term "levodopa" means a pharmacologically active agent, wherein Q is represented by the formula UUUUU, $R_1$ is H, and the structure $$"-\xi-"$$

is replaced with H.

The term "lofexidine" means a pharmacologically active agent, wherein Q is represented by the formula VVVVV, $R_1$ is absent, and the structure $$"-\xi-"$$

is replaced with H.

The term "mecamylamine" means a pharmacologically active agent, wherein Q is represented by the formula WWWWW, $R_1$ is methyl, and the structure $$"-\xi-"$$

is replaced with H.

The term "mefenamic acid" means a pharmacologically active agent, wherein Q is represented by the formula XXXXX, $R_1$ is absent, and the structure $$"-\xi-"$$

is replaced with H.

The term "mephentermine" means a pharmacologically active agent, wherein Q is represented by the formula YYYYY, $R_1$ is methyl, and the structure $$"-\xi-"$$

is replaced with H.

The term "metaraminol" means a pharmacologically active agent, wherein Q is represented by the formula ZZZZZ, $R_1$ is H, and the structure $$"-\xi-"$$

is replaced with H.

The term "methyldopa" means a pharmacologically active agent, wherein Q is represented by the formula 2A, $R_1$ is H, and the structure $$"-\xi-"$$

is replaced with H.

The term "metyrosine" means a pharmacologically active agent, wherein Q is represented by the formula 2B, $R_1$ is H, and the structure $$"-\xi-"$$

is replaced with H.

The term "neomycin A" means a pharmacologically active agent, wherein Q is represented by the formula 2C-1, 2C-2, 2C-3, or 2C-4, $R_1$ is H, and the structure $$"-\xi-"$$

is replaced with H.

The term "niflumic acid" means a pharmacologically active agent, wherein Q is represented by the formula 2D, $R_1$ is absent, and the structure $$"-\xi-"$$

is replaced with H.

The term "nimodipine" means a pharmacologically active agent, wherein Q is represented by the formula 2E, R$_1$ is absent, and the structure

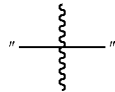

is replaced with H.

The term "nomifensine" means a pharmacologically active agent, wherein Q is represented by the formula 2F, R$_1$ is H, and the structure

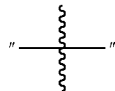

is replaced with H.

The term "nylidrin" means a pharmacologically active agent, wherein Q is represented by the formula 2G, R$_1$ is absent, and the structure

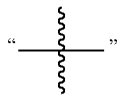

is replaced with H.

The term "oxamniquine" means a pharmacologically active agent, wherein Q is represented by the formula 2H-1 or 2H-2, R$_1$ is absent, and the structure

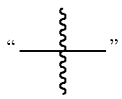

is replaced with H.

The term "oxyfedrine" means a pharmacologically active agent, wherein Q is represented by the formula 2I, R$_1$ is absent, and the structure

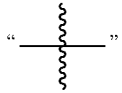

is replaced with H.

The term "perhexyline" means a pharmacologically active agent, wherein Q is represented by the formula 2J, R$_1$ is absent, and the structure

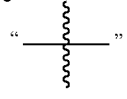

is replaced with H.

The term "phenmetrazine" means a pharmacologically active agent, wherein Q is represented by the formula 2K, R$_1$ is absent, and the structure

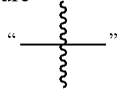

is replaced with H.

The term "phenylpropanolamine" means a pharmacologically active agent, wherein Q is represented by the formula 2L, R$_1$ is H, and the structure

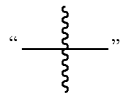

is replaced with H.

The term "phenylephrine" means a pharmacologically active agent, wherein Q is represented by the formula 2M, R$_1$ is methyl, and the structure

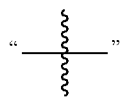

is replaced with H.

The term "pipemidic acid" means a pharmacologically active agent, wherein Q is represented by the formula 2N, R$_1$ is absent, and the structure

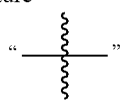

is replaced with H.

The term "piperazine" means a pharmacologically active agent, wherein Q is represented by the formula 2O, R$_1$ is absent, and the structure

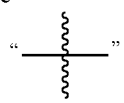

is replaced with H.

The term "pipradrol" means a pharmacologically active agent, wherein Q is represented by the formula 2P, R$_1$ is absent, and the structure

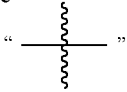

is replaced with H.

The term "pramipexole" means a pharmacologically active agent, wherein Q is represented by the formula 2Q-1 (R$_1$ is absent) or 2Q-2 (R$_1$ is H), and the structure

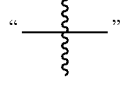

is replaced with H.

The term "primaquine" means a pharmacologically active agent, wherein Q is represented by the formula 2R-1 (R$_1$ is H) or 2R-2 (R$_1$ is absent), and the structure

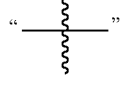

is replaced with H.

The term "procainamide" means a pharmacologically active agent, wherein Q is represented by the formula 2S, $R_1$ is H, and the structure

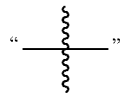

is replaced with H.

The term "procarbazine" means a pharmacologically active agent, wherein Q is represented by the formula 2T-1 ($R_1$ is absent) or 2T-2 ($R_1$ is methyl) and the structure

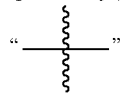

is replaced with H.

The term "pyrimethamine" means a pharmacologically active agent, wherein Q is represented by the formula 2U-1 or 2U-2, $R_1$ is H, and the structure

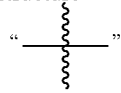

is replaced with H.

The term "quinethazone" means a pharmacologically active agent, wherein Q is represented by the formula 2V, $R_1$ is absent, and the structure

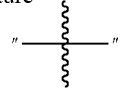

is replaced with H.

The term "sisomicin" means a pharmacologically active agent, wherein Q is represented by the formula 2W-1 ($R_1$ is methyl), 2W-2 ($R_1$ is H), 2W-3 ($R_1$ is H), 2W-4 ($R_1$ is H), and 2W-5 ($R_1$ is H), and the structure

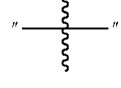

is replaced with H.

The term "sparfloxacin" means a pharmacologically active agent, wherein Q is represented by the formula 2X-1 ($R_1$ is absent) or 2X-2 ($R_1$ is H) and the structure

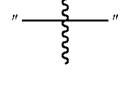

is replaced with H.

The term "spectinomycin" means a pharmacologically active agent, wherein Q is represented by the formula 2Y-1 or 2Y-2, $R_1$ is methyl and the structure

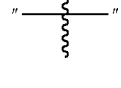

is replaced with H.

The term "sulfacytine" means a pharmacologically active agent, wherein Q is represented by the formula 2Z, $R_1$ is H, and the structure

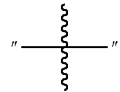

is replaced with H.

The term "sulfadimethoxine" means a pharmacologically active agent, wherein Q is represented by the formula 2AA, $R_1$ is H, and the structure

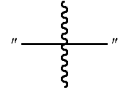

is replaced with H.

The term "sulfadoxine" means a pharmacologically active agent, wherein Q is represented by the formula 2BB, $R_1$ is H, and the structure

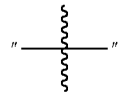

is replaced with H.

The term "sulfaguanidine" means a pharmacologically active agent, wherein Q is represented by the formula 2CC-1 or 2CC-2, $R_1$ is H, and the structure

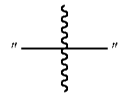

is replaced with H.

The term "sulfaguanole" means a pharmacologically active agent, wherein Q is represented by the formula 2DD, $R_1$ is H, and the structure

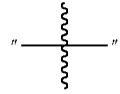

is replaced with H.

The term "sulfamethoxypyridazine" means a pharmacologically active agent, wherein Q is represented by the formula 2EE, $R_1$ is H, and the structure

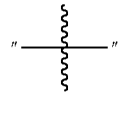

is replaced with H.

The term "sulfameter" means a pharmacologically active agent, wherein Q is represented by the formula 2FF, $R_1$ is H, and the structure

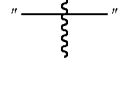

is replaced with H.

The term "sulfamerazine" means a pharmacologically active agent, wherein Q is represented by the formula 2GG, $R_1$ is H, and the structure

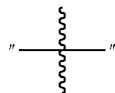

is replaced with H.

The term "sulfamethazine" means a pharmacologically active agent, wherein Q is represented by the formula 2HH, $R_1$ is H, and the structure

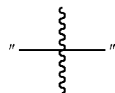

is replaced with H.

The term "sulfamethizole" means a pharmacologically active agent, wherein Q is represented by the formula 2II, $R_1$ is H, and the structure

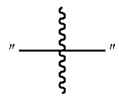

is replaced with H.

The term "sulfamethomidine" means a pharmacologically active agent, wherein Q is represented by the formula 2JJ, $R_1$ is H, and the structure

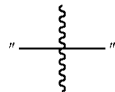

is replaced with H.

The term "sulfamoxole" means a pharmacologically active agent, wherein Q is represented by the formula 2KK, $R_1$ is H, and the structure

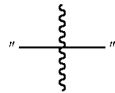

is replaced with H.

The term "sulfisoxazole" means a pharmacologically active agent, wherein Q is represented by the formula 2LL, $R_1$ is H, and the structure

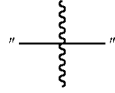

is replaced with H.

The term "sulfisoxazole acetal" means a pharmacologically active agent, wherein Q is represented by the formula 2MM, $R_1$ is H, and the structure

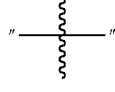

is replaced with H.

The term "sulfonamide CS61" means means a pharmacologically active agent, wherein Q is represented by the formula 2NN, $R_1$ is H, and the structure

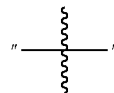

is replaced with H.

The term "tamsulosin" means a pharmacologically active agent, wherein Q is represented by the formula 2OO, $R_1$ is absent, and the structure

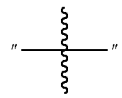

is replaced with H.

The term "terbutaline" means a pharmacologically active agent, wherein Q is represented by the formula 2PP, $R_1$ is tert-butyl, and the structure

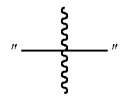

is replaced with H.

The term "thiamphenicol glycinate" means a pharmacologically active agent, wherein Q is represented by the formula 2QQ, $R_1$ is H, and the structure

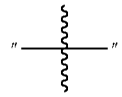

is replaced with H.

The term "timonacic" means a pharmacologically active agent, wherein Q is represented by the formula 2RR, $R_1$ is absent, and the structure

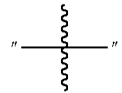

is replaced with H.

The term "tinoridine" means a pharmacologically active agent, wherein Q is represented by the formula 2SS, $R_1$ is H, and the structure

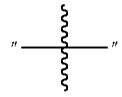

is replaced with H.

The term "tizanidine" means a pharmacologically active agent, wherein Q is represented by the formula 2TT-1 or 2TT-2, $R_1$ is absent, and the structure

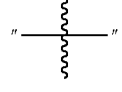

is replaced with H.

The term "tolazoline" means a pharmacologically active agent, wherein Q is represented by the formula 2UU, $R_1$ is absent, and the structure

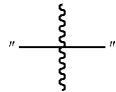

is replaced with H.

The term "tretoquinol" means a pharmacologically active agent, wherein Q is represented by the formula 2VV, $R_1$ is absent, and the structure

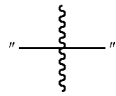

is replaced with H.

The term "triamterene" means a pharmacologically active agent, wherein Q is represented by the formula 2WW-1, 2WW-2 or 2WW-3, $R_1$ is H, and the structure

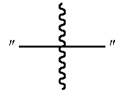

is replaced with H.

The term "trichlormethiazide" means a pharmacologically active agent, wherein Q is represented by the formula 2XX, $R_1$ is absent, and the structure

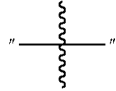

is replaced with H.

The term "trientine" means a pharmacologically active agent, wherein Q is represented by the formula 2YY-1 ($R_1$ is H) or 2YY-2 ($R_1$ is absent), and the structure

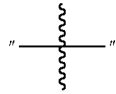

is replaced with H.

The term "trimethoprim" means a pharmacologically active agent, wherein Q is represented by the formula 2ZZ-1 or 2ZZ-2, $R_1$ is H, and the structure

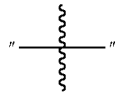

is replaced with H.

The term "trimetrexate" means a pharmacologically active agent, wherein Q is represented by the formula 2AAA-1 or 2AAA-2 ($R_1$ is H), and the structure

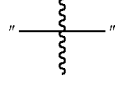

is replaced with H.

The term "tromethamine" means a pharmacologically active agent, wherein Q is represented by the formula 2BBB, $R_1$ is H, and the structure

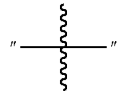

is replaced with H.

The term "troxipide" means a pharmacologically active agent, wherein Q is represented by the formula 2CCC, $R_1$ is absent, and the structure

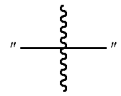

is replaced with H.

The term "tryptophan" means a pharmacologically active agent, wherein Q is represented by the formula 2DDD, $R_1$ is H, and the structure

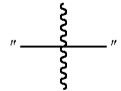

is replaced with H.

The term "zalcitibine" means a pharmacologically active agent, wherein Q is represented by the formula 2EEE, $R_1$ is H, and the structure

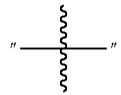

is replaced with H.

The term "alendronic acid" means a pharmacologically active agent, wherein Q is represented by the formula 2FFF, $R_1$ is H, and the structure

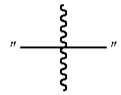

is replaced with H.

The term "alanine" means a pharmacologically active agent, wherein Q is represented by the formula 2GGG, $R_1$ is H, and the structure

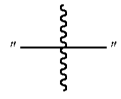

is replaced with H.

The term "arginine" means a pharmacologically active agent, wherein Q is represented by the formula 2HHH-1 or 2HHH-2, $R_1$ is H, and the structure

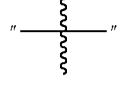

is replaced with H.

The term "asparagine" means a pharmacologically active agent, wherein Q is represented by the formula 2III, $R_1$ is H, and the structure

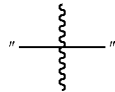

is replaced with H.

The term "aspartic acid" means a pharmacologically active agent, wherein Q is represented by the formula 2JJJ, $R_1$ is H, and the structure

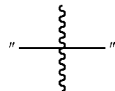

is replaced with H.

The term "cysteine" means a pharmacologically active agent, wherein Q is represented by the formula 2KKK, $R_1$ is H, and the structure

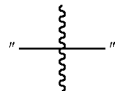

is replaced with H.

The term "glutamic acid" means a pharmacologically active agent, wherein Q is represented by the formula 2LLL, $R_1$ is H, and the structure

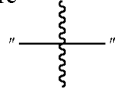

is replaced with H.

The term "histidine" means a pharmacologically active agent, wherein Q is represented by the formula 2MMM-1 ($R_1$ is H), 2MMM-2 ($R_1$ is absent), 2MMM-3 ($R_1$ is absent), and the structure

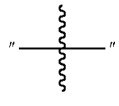

is replaced with H.

The term "isoleucine" means a pharmacologically active agent, wherein Q is represented by the formula 2NNN, $R_1$ is H, and the structure

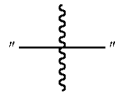

is replaced with H.

The term "leucine" means a pharmacologically active agent, wherein Q is represented by the formula 2OOO, $R_1$ is H, and the structure

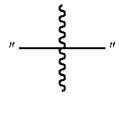

is replaced with H.

The term "lysine" means a pharmacologically active agent, wherein Q is represented by the formula 2PPP-1 or 2PPP-2, $R_1$ is H, and the structure

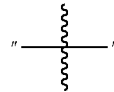

is replaced with H.

The term "methionine" means a pharmacologically active agent, wherein Q is represented by the formula 2QQQ, $R_1$ is H, and the structure

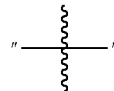

is replaced with H.

The term "phenylalanine" means a pharmacologically active agent, wherein Q is represented by the formula 2RRR, $R_1$ is H, and the structure

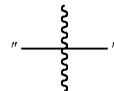

is replaced with H.

The term "proline" means a pharmacologically active agent, wherein Q is represented by the formula 2SSS, $R_1$ is absent, and the structure

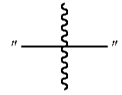

is replaced with H.

The term "serine" means a pharmacologically active agent, wherein Q is represented by the formula 2TTT, $R_1$ is H, and the structure

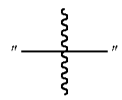

is replaced with H.

The term "threonine" means a pharmacologically active agent, wherein Q is represented by the formula 2UUU, $R_1$ is H, and the structure

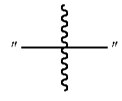

is replaced with H.

The term "tyrosine" means a pharmacologically active agent, wherein Q is represented by the formula 2VVV, $R_1$ is H, and the structure

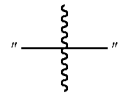

is replaced with H.

The term "valine" means a pharmacologically active agent, wherein Q is represented by the formula 2WWW, $R_1$ is H, and the structure

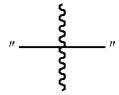

is replaced with H.

The term "deferoxamine" means a pharmacologically active agent, wherein Q is represented by the formula 2XXX, $R_1$ is H, and the structure

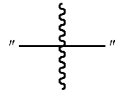

is replaced with H.

The term "mesalamine" means a pharmacologically active agent, wherein Q is represented by the formula 2YYY, $R_1$ is H, and the structure

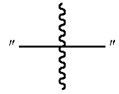

is replaced with H.

The term "phentolamine" means a pharmacologically active agent, wherein Q is represented by the formula 2ZZZ, $R_1$ is absent, and the structure

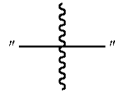

is replaced with H.

The term "thiamine" means a pharmacologically active agent, wherein Q is represented by the formula 2AAAA, $R_1$ is H, and the structure

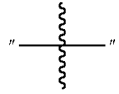

is replaced with H.

The term "adefovir dipivoxil" means a pharmacologically active agent, wherein Q is represented by the formula 2BBBB, $R_1$ is H, and the structure

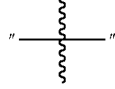

is replaced with H.

The term "adenosine" means a pharmacologically active agent, wherein Q is represented by the formula 2CCCC, $R_1$ is H, and the structure

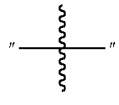

is replaced with H.

The term "alatrofloxacin" means a pharmacologically active agent, wherein Q is represented by the formula 2DDDD, $R_1$ is H, and the structure

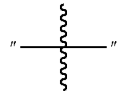

is replaced with H.

The term "alendronate" means a pharmacologically active agent, wherein Q is represented by the formula 2EEEE, $R_1$ is H, and the structure

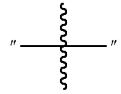

is replaced with H.

The term "alfuzosin" means a pharmacologically active agent, wherein Q is represented by the formula 2FFFF, $R_1$ is H, and the structure

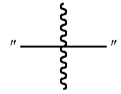

is replaced with H.

The term "almotriptan" means a pharmacologically active agent, wherein Q is represented by the formula 2GGGG, $R_1$ is absent, and the structure

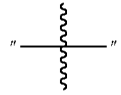

is replaced with H.

The term "alosetron" means a pharmacologically active agent, wherein Q is represented by the formula 2HHHH and the structure

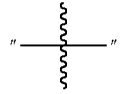

is replaced with H.

The term "amifostine" means a pharmacologically active agent, wherein Q is represented by the formula 2IIII-1 ($R_1$ is H) or 2IIII-2 ($R_1$ is absent), and the structure

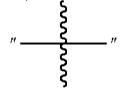

is replaced with H.

The term "levulan" means a pharmacologically active agent, wherein Q is represented by the formula 2JJJJ, $R_1$ is H, and the structure

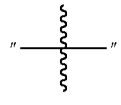

is replaced with H.

The term "amlexanox" means a pharmacologically active agent, wherein Q is represented by the formula 2KKKK, $R_1$ is H, and the structure

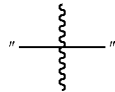

is replaced with H.

The term "amprenavir" means a pharmacologically active agent, wherein Q is represented by the formula 2LLLL, $R_1$ is H, and the structure

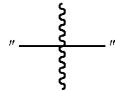

is replaced with H.

The term "anagrelide" means a pharmacologically active agent, wherein Q is represented by the formula 2MMMM, $R_1$ is absent, and the structure

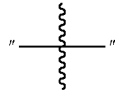

is replaced with H.

The term "apraclonidine" means a pharmacologically active agent, wherein Q is represented by the formula 2NNNN-1 ($R_1$ is H), 2NNNN-2 ($R_1$ is absent), or 2NNNN-3 ($R_1$ is absent), and the structure

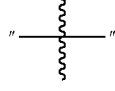

is replaced with H.

The term "aprepitant" means a pharmacologically active agent, wherein Q is represented by the formula 2OOOO-1 or 2OOOO-2, $R_1$ is absent, and the structure

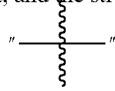

is replaced with H.

The term "argatroban" means a pharmacologically active agent, wherein Q is represented by the formula 2PPPP-1 ($R_1$ is H) or 2PPPP-2 ($R_1$ is absent), and the structure

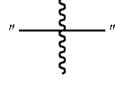

is replaced with H.

The term "atovaquone" means a pharmacologically active agent, wherein Q is represented by the formula 2QQQQ, $R_1$ is absent, and the structure

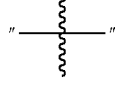

is replaced with H.

The term "brimonidine" means a pharmacologically active agent, wherein Q is represented by the formula 2RRRR-1 or 2RRRR-2, $R_1$ is absent, and the structure

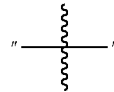

is replaced with H.

The term "bromfenac" means a pharmacologically active agent, wherein Q is represented by the formula 2SSSS, $R_1$ is H, and the structure

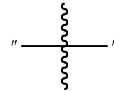

is replaced with H.

The term "cabergoline" means a pharmacologically active agent, wherein Q is represented by the formula 2TTTT, $R_1$ is absent, and the structure

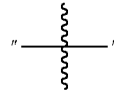

is replaced with H.

The term "candesartan" means a pharmacologically active agent, wherein Q is represented by the formula 2UUUU-1 or 2UUUU-2, $R_1$ is absent, and the structure

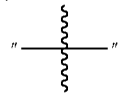

is replaced with H.

The term "carbidopa" means a pharmacologically active agent, wherein Q is represented by the formula 2VVVV-1 ($R_1$ is H) or 2VVVV-2 ($R_1$ is absent), and the structure

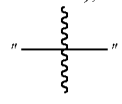

is replaced with H.

The term "cefditoren pivoxil" means a pharmacologically active agent, wherein Q is represented by the formula 2WWWW, $R_1$ is H, and the structure

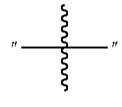

is replaced with H.

The term "cidofovir" means a pharmacologically active agent, wherein Q is represented by the formula 2XXXX, $R_1$ is H, and the structure

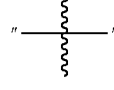

is replaced with H.

The term "cisapride" means a pharmacologically active agent, wherein Q is represented by the formula 2YYYY, R₁ is H, and the structure

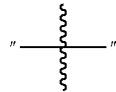

is replaced with H.

The term "clofarabine" means a pharmacologically active agent, wherein Q is represented by the formula 2ZZZZ, R₁ is H, and the structure

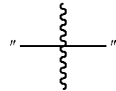

is replaced with H.

The term "colestipol" means a pharmacologically active agent, wherein Q is represented by the formula 2AAAAA-1 (R₁ is H) or 2AAAAA-2 (R₁ is absent), or 2AAAAA-3 (R₁ is absent), and the structure

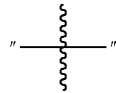

is replaced with H.

The term "conivaptan" means a pharmacologically active agent, wherein Q is represented by the formula 2BBBBB and the structure

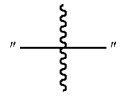

is replaced with H.

The term "cytarabine" means a pharmacologically active agent, wherein Q is represented by the formula 2CCCCC, R₁ is H, and the structure

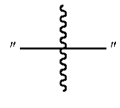

is replaced with H.

The term "deferasirox" means a pharmacologically active agent, wherein Q is represented by the formula 2DDDDD-1 or 2DDDDD-2, R₁ is absent, and the structure

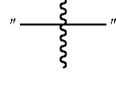

is replaced with H.

The term "delavirdine" means a pharmacologically active agent, wherein Q is represented by the formula 2EEEEE-1 or 2EEEEE-2, R₁ is absent, and the structure

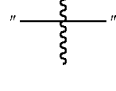

is replaced with H.

The term "dexmedetomidine" means a pharmacologically active agent, wherein Q is represented by the formula 2FFFFF-1 or 2FFFFF-2, R₁ is absent, and the structure

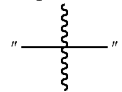

is replaced with H.

The term "dexmethylphenidate" means a pharmacologically active agent, wherein Q is represented by the formula 2GGGGG, R₁ is absent, and the structure

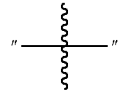

is replaced with H.

The term "didanosine" means a pharmacologically active agent, wherein Q is represented by the formula 2HHHHH, R₁ is absent, and the structure

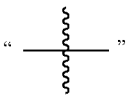

is replaced with H.

The term "migranal" means a pharmacologically active agent, wherein Q is represented by the formula 2IIIII, R₁ is absent, and the structure

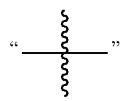

is replaced with H.

The term "dolasetron" means a pharmacologically active agent, wherein Q is represented by the formula 2JJJJJ, R₁ is absent, and the structure

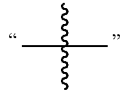

is replaced with H.

The term "doxazosin" means a pharmacologically active agent, wherein Q is represented by the formula 2KKKKK, R₁ is H, and the structure

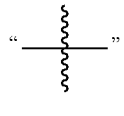

is replaced with H.

The term "doxorubicin" means a pharmacologically active agent, wherein Q is represented by the formula 2LLLLL, R₁ is H, and the structure

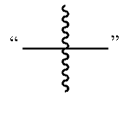

is replaced with H.

The term "emtricitabine" means a pharmacologically active agent, wherein Q is represented by the formula 2MMMMM, $R_1$ is H, and the structure

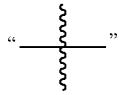

is replaced with H.

The term "enalapril" means a pharmacologically active agent, wherein Q is represented by the formula 2NNNNN, $R_1$ is absent, and the structure

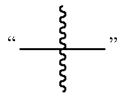

is replaced with H.

The term "felodipine" means a pharmacologically active agent, wherein Q is represented by the formula 2OOOOO, $R_1$ is absent, and the structure

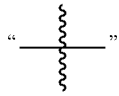

is replaced with H.

The term "epinastine" means a pharmacologically active agent, wherein Q is represented by the formula 2PPPPP, $R_1$ is H, and the structure

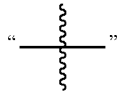

is replaced with H.

The term "erlotinib" means a pharmacologically active agent, wherein Q is represented by the formula 2QQQQQ, $R_1$ is absent, and the structure

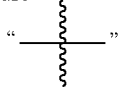

is replaced with H.

The term "ertapenem" means a pharmacologically active agent, wherein Q is represented by the formula 2RRRRR, $R_1$ is absent, and the structure

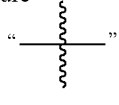

is replaced with H.

The term "omeprazole" means a pharmacologically active agent, wherein Q is represented by the formula 2SSSSS, $R_1$ is absent, and the structure

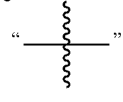

is replaced with H.

The term "etodolac" means a pharmacologically active agent, wherein Q is represented by the formula 2TTTTT, $R_1$ is absent, and the structure

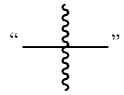

is replaced with H.

The term "famciclovir" means a pharmacologically active agent, wherein Q is represented by the formula 2UUUUU, $R_1$ is H, and the structure

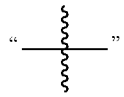

is replaced with H.

The term "famotidine" means a pharmacologically active agent, wherein Q is represented by the formula 2VVVVV-1 or 2VVVVV-2, $R_1$ is H, and the structure

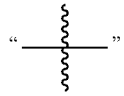

is replaced with H.

The term "fenoldopam" means a pharmacologically active agent, wherein Q is represented by the formula 2WWWWW, $R_1$ is absent, and the structure

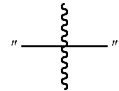

is replaced with H.

The term "fomepizole" means a pharmacologically active agent, wherein Q is represented by the formula 2XXXXX, $R_1$ is absent, and the structure

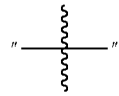

is replaced with H.

The term "fosamprenavir" means a pharmacologically active agent, wherein Q is represented by the formula 2YYYYY, $R_1$ is H, and the structure

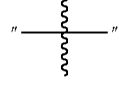

is replaced with H.

The term "gatifloxacin" means a pharmacologically active agent, wherein Q is represented by the formula 2ZZZZZ, $R_1$ is absent, and the structure

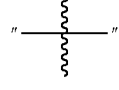

is replaced with H.

The term "ganciclovir" means a pharmacologically active agent, wherein Q is represented by the formula 3A-1 ($R_1$ is H) or 3A-2 ($R_1$ is absent) and the structure

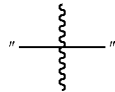

is replaced with H.

The term "gefitinib" means a pharmacologically active agent, wherein Q is represented by the formula 3B, $R_1$ is absent, and the structure

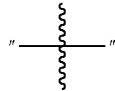

is replaced with H.

The term "gemcitabine" means a pharmacologically active agent, wherein Q is represented by the formula 3C, $R_1$ is H, and the structure

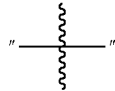

is replaced with H.

The term "gemifloxacin" means a pharmacologically active agent, wherein Q is represented by the formula 3D, $R_1$ is H, and the structure

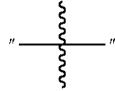

is replaced with H.

The term "grepafloxacin" means a pharmacologically active agent, wherein Q is represented by the formula 3E, $R_1$ is absent, and the structure

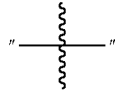

is replaced with H.

The term "imatinib" means a pharmacologically active agent, wherein Q is represented by the formula 3F, $R_1$ is absent, and the structure

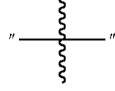

is replaced with H.

The term "imiquimod" means a pharmacologically active agent, wherein Q is represented by the formula 3G, $R_1$ is H, and the structure

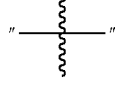

is replaced with H.

The term "irbesartan" means a pharmacologically active agent, wherein Q is represented by the formula 3H-1 or 3H-2, $R_1$ is absent, and the structure

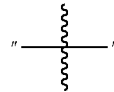

is replaced with H.

The term "isradipine" means a pharmacologically active agent, wherein Q is represented by the formula 3I, $R_1$ is absent, and the structure

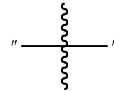

is replaced with H.

The term "levothyroxine" means a pharmacologically active agent, wherein Q is represented by the formula 3J, $R_1$ is H, and the structure

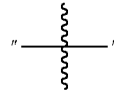

is replaced with H.

The term "menotropins" means a pharmacologically active agent, wherein Q is represented by the formula 3K, $R_1$ is H, and the structure

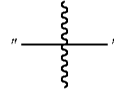

is replaced with H.

The term "methyl aminolevulinate" means a pharmacologically active agent, wherein Q is represented by the formula 3L, $R_1$ is H, and the structure

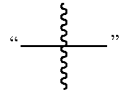

is replaced with H.

The term "metformin" means a pharmacologically active agent, wherein Q is represented by the formula 3M-1 ($R_1$ is H) or 3M-2 ($R_1$ is absent) and the structure

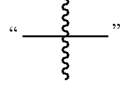

is replaced with H.

The term "mitoxantrone" means a pharmacologically active agent, wherein Q is represented by the formula 3N-1 or 3N-2, $R_1$ is absent, and the structure

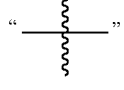

is replaced with H.

The term "moexipril" means a pharmacologically active agent, wherein Q is represented by the formula 3O and the structure

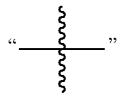

is replaced with H.

The term "naratriptan" means a pharmacologically active agent, wherein Q is represented by the formula 3P, $R_1$ is absent, and the structure

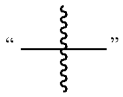

is replaced with H.

The term "nelarabine" means a pharmacologically active agent, wherein Q is represented by the formula 3Q, $R_1$ is H, and the structure

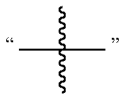

is replaced with H.

The term "moxifloxacin" means a pharmacologically active agent, wherein Q is represented by the formula 3R, $R_1$ is absent, and the structure

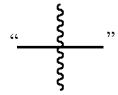

is replaced with H.

The term "nicardipine" means a pharmacologically active agent, wherein Q is represented by the formula 3S, $R_1$ is absent, and the structure

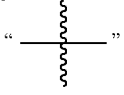

is replaced with H.

The term "nisoldipine" means a pharmacologically active agent, wherein Q is represented by the formula 3T, $R_1$ is absent, and the structure

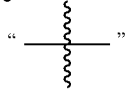

is replaced with H.

The term "nizatidine" means a pharmacologically active agent, wherein Q is represented by the formula 3U-1 or 3U-2, $R_1$ is absent, and the structure

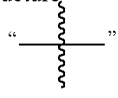

is replaced with H.

The term "olanzapine" means a pharmacologically active agent, wherein Q is represented by the formula 3V, $R_1$ is absent, and the structure

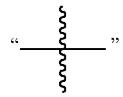

is replaced with H.

The term "oseltamivir" means a pharmacologically active agent, wherein Q is represented by the formula 3W, $R_1$ is H, and the structure

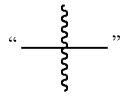

is replaced with H.

The term "olmesartan medoxomil" means a pharmacologically active agent, wherein Q is represented by the formula 3X-1 or 3X-2, $R_1$ is absent, and the structure

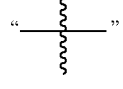

is replaced with H.

The term "oxaliplatin" means a pharmacologically active agent, wherein Q is represented by the formula 3Y, and the structure

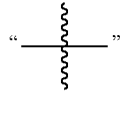

is replaced with H.

The term "pamidronic acid" means a pharmacologically active agent, wherein Q is represented by the formula 3Z, $R_1$ is H, and the structure

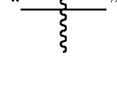

is replaced with H.

The term "pantoprazole" means a pharmacologically active agent, wherein Q is represented by the formula 3AA, $R_1$ is absent, and the structure

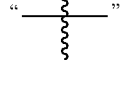

is replaced with H.

The term "pemetrexed" means a pharmacologically active agent, wherein Q is represented by the formula 3BB-1 ($R_1$ is H), 3BB-2 ($R_1$ is absent), or 3BB-3 ($R_1$ is absent), and the structure

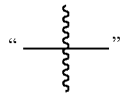

is replaced with H.

The term "penciclovir" means a pharmacologically active agent, wherein Q is represented by the formula 3CC-1 (R₁ is H) or 3CC-2 (R₁ is absent) and the structure

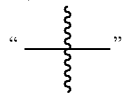

is replaced with H.

The term "pergolide" means a pharmacologically active agent, wherein Q is represented by the formula 3DD, R₁ is absent, and the structure

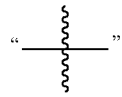

is replaced with H.

The term "perindopril" means a pharmacologically active agent, wherein Q is represented by the formula 2EE, R₁ is absent, and the structure

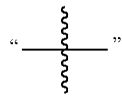

is replaced with H.

The term "propafenone" means a pharmacologically active agent, wherein Q is represented by the formula 3FF, R₁ is absent, and the structure

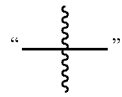

is replaced with H.

The term "quinapril" means a pharmacologically active agent, wherein Q is represented by the formula 3GG, R₁ is absent, and the structure

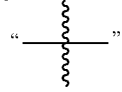

is replaced with H.

The term "rabeprazole" means a pharmacologically active agent, wherein Q is represented by the formula 3HH, R₁ is absent, and the structure

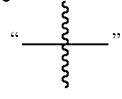

is replaced with H.

The term "ranitidine" means a pharmacologically active agent, wherein Q is represented by the formula 3II-1 or 3II-2, R₁ is absent, and the structure

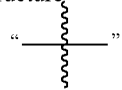

is replaced with H.

The term "rizatriptan" means a pharmacologically active agent, wherein Q is represented by the formula 3JJ, R₁ is absent, and the structure

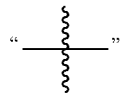

is replaced with H.

The term "sevelamer" means a pharmacologically active agent, wherein Q is represented by the formula 3KK, R₁ is H, and the structure

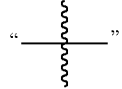

is replaced with H.

The term "sildenafil" means a pharmacologically active agent, wherein Q is represented by the formula 3LL, R₁ is absent, and the structure

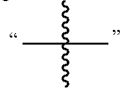

is replaced with H.

The term "sumatriptan" means a pharmacologically active agent, wherein Q is represented by the formula 3MM, R₁ is absent, and the structure

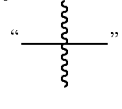

is replaced with H.

The term "tacrine" means a pharmacologically active agent, wherein Q is represented by the formula 3NN, R₁ is H, and the structure

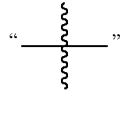

is replaced with H.

The term "tadalafil" means a pharmacologically active agent, wherein Q is represented by the formula 3OO, R₁ is absent, and the structure

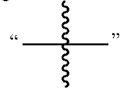

is replaced with H.

The term "tegaserod" means a pharmacologically active agent, wherein Q is represented by the formula 3PP-1 (R₁ is H), 3PP-2 (R₁ is absent), 3PP-3 (R₁ is absent), and the structure

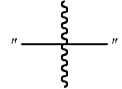

is replaced with H.

The term "tenofovir" means a pharmacologically active agent, wherein Q is represented by the formula 3QQ, $R_1$ is H, and the structure

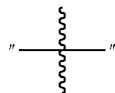

is replaced with H.

The term "terazosin" means a pharmacologically active agent, wherein Q is represented by the formula 3RR, $R_1$ is H, and the structure

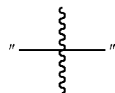

is replaced with H.

The term "tigecycline" means a pharmacologically active agent, wherein Q is represented by the formula 3SS-1 or 3SS-2, $R_1$ is H, and the structure

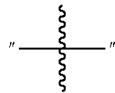

is replaced with H.

The term "tirofiban" means a pharmacologically active agent, wherein Q is represented by the formula 3TT, $R_1$ is absent, and the structure

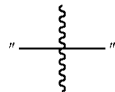

is replaced with H.

The term "torsemide" means a pharmacologically active agent, wherein Q is represented by the formula 3UU, $R_1$ is absent, and the structure

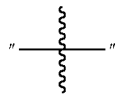

is replaced with H.

The term "trandolapril" means a pharmacologically active agent, wherein Q is represented by the formula 3VV, $R_1$ is absent, and the structure

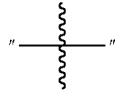

is replaced with H.

The term "trovafloxacin" means a pharmacologically active agent, wherein Q is represented by the formula 3WW, $R_1$ is H, and the structure

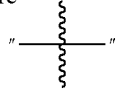

is replaced with H.

The term "valacyclovir" means a pharmacologically active agent, wherein Q is represented by the formula 3XX-1 or 3XX-2, $R_1$ is H, and the structure

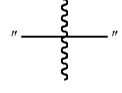

is replaced with H.

The term "valganciclovir" means a pharmacologically active agent, wherein Q is represented by the formula 3YY-1 or 3YY-2, $R_1$ is H, and the structure

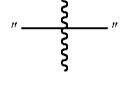

is replaced with H.

The term "valsartan" means a pharmacologically active agent, wherein Q is represented by the formula 3ZZ-1 or 3ZZ-2, $R_1$ is absent, and the structure

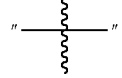

is replaced with H.

The term "vardenafil" means a pharmacologically active agent, wherein Q is represented by the formula 3AAA, $R_1$ is absent, and the structure

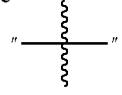

is replaced with H.

The term "zalcitabine" means a pharmacologically active agent, wherein Q is represented by the formula 3BBB, $R_1$ is H, and the structure

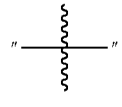

is replaced with H.

The term "zolmitriptan" means a pharmacologically active agent, wherein Q is represented by the formula 3CCC-1 or 3CCC-2, $R_1$ is absent, and the structure

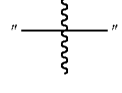

is replaced with H.

In another embodiment, the pharmacologically active agent, QH, is at least one member selected from the group consisting of a cholinergic (also referred to as ACh) agent, an adrenergic (also referred to as epinephrine) agent, a noradrenergic (also referred to as norepinephrine) agent, a dopaminergic agent, a serotonergic (also referred to as 5-hydroxytryptamine) agent, a glutamatergic agent, a GABAergic (gamma-aminobutyric acid) agent, a histaminergic agent (e.g., HTMT, amthamine, immepip, and alpha-methylhistamine (Tocris, Ellisville, Mo.)), a mono-amine oxidase inhibitor, a catechol-O-methyl transferase (COMT) inhibitor, a beta secretase inhibitor, a gamma secretase inhibitor, a potassium channel blocker, a calcium channel blocker (e.g., nimodipine), an adenosine receptor modulator, a cannabinoid receptor modulator (e.g., virodhamine), a nootropic (i.e., cognition enhancing agent) (e.g., safinamide, minaprine, indeloxazine), a neuropeptide pathway modulator, a neurotrophic (i.e., an agent that induces neuronal cell growth), phosphodiesterase (PDE) IV inhibitor, a phosphatase/calcineurin inhibitor, a carbonic anhydrase inhibitor (e.g., brinzolamide, dorzolamide), a receptor trafficking regulator, a trace amine receptor modulator, a sigma receptor modulator, imidazoline receptor modulator, a sodium/calcium exchange blocker (also referred to as a $Na^+Ca^{+2}$ exchanger or NCX), ACE (Angiotensen Converting Enzyme) inhibitors, antioxidants and NSAIDs thon-Steriodal Anti-Inflammatory Drugs).

The pharmacologically active agent, QH, can also be a trace amine neurotransmitter, such as octopamine, tyramine, or tryptamine.

An "agent," as used herein, refers to a compound that can produce a physical, chemical or biological effect that can be stimulatory (e.g., an activating agent) or inhibitory (e.g., a blocking agent). Agents that are stimulatory can be agonists. Agents that are inhibitory can be antagonists or inverse agonists. Inverse agonists are compounds that down-regulate receptor activated activity thereby acting in a manner that is the opposite of an agonist to the receptor. Thus, exposure or administration of an inverse agonist can result in a diminished response compared to exposure or administration of an agonist.

A cholinergic agent can be, for example, a compound that stimulates the action of ACh thereby mediating ACh-mediated cell signaling between two cells (a cholinergic agonist). Stimulation can be, for example, a result of facilitating binding of ACh to a cell surface receptor, interference with degradation of ACh, stimulation of release of ACh, stimulation of synthesis of ACh, activation of second messengers (e.g., phospholipase C, inositol 1,4,5-triphosphate, protein kinase C, protein kinase A) that mediate ACh cell signaling, alteration of ion (e.g., sodium, potassium) channels in target cells. An agent can also inhibit or prevent any one or more of these effects (e.g., a cholinergic antagonist).

Upon hydrolysis of the compound of the invention, the released amine can become a pharmacologically active agent which can specifically affect one or both of the two ACh receptor subtypes, muscarinic cholinergic receptors and nicotinic cholinergic receptors, thereby targeting a particular receptor subtype that mediates a particular biological process. In one embodiment, the cholinergic agent is selected from a muscarinic cholinergic receptor agonist, (Cutler, N. R., et al., *CNS Drugs* 3:467-481 (1995); Korczyn, A. D., *Drugs* 9: 2259-2267 (2000), the teachings of all of which are hereby incorporated by referenced in their entirety), a muscarinic cholinergic receptor antagonist, a nicotinic cholinergic receptor agonist, a nicotinic cholinergic receptor antagonist, an acetylcholinesterase inhibitor, a cholinergic antagonist, an allosteric modulator of a cholinergic receptor and an open channel blocker.

A muscarinic cholinergic receptor agonist or antagonist can mediate effects in a variety of tissues, including smooth muscle, cardiac muscle, exocrine glands and the nervous system of individuals. A nicotinic cholinergic receptor agonist or antagonist can also mediate effects by altering the biological, physical or chemical components of ganglia in the autonomic nervous system, at neuromuscular junctions of the peripheral or autonomic nervous system and in the central nervous system.

In another embodiment, hydrolysis of the compound of the invention, by reaction with a cholinesterase, causes formation of a cholinergic agonist selected from RJR2403 (Methyl-(4-pyridin-3-yl-but-3-enyl)-amine) (also referred to as TC2403), A85380 (3-(Azetidin-2-ylmethoxy)-pyridine), anatoxin A, epibatidine and anabasine (Tocris, Ellisville, Mo.); and TC1734 ([4-(5-Isopropoxy-pyridin-3-yl)-1-methyl-but-3-enyl]-methyl-amine) (Obinu, M. C. et al., *Progress in Neuropsychopharmacol. & Biol. Psychiatry* 26:913-918 (2002); Obinu, M. C. et al., *Internatl. J. Neuropyschopharamology* 3: Suppl 1 (S361) (2003); Lipiello, P. M. et al., *Soc. Neurosci. Abstr* 24: 88 (Part 1) (1998); Gatto, G., et al., *CNS Drug Reviews,* 10:147-166 (2004)).

In an additional embodiment, the hydrolysis of the compound of the invention, by reaction with a cholinesterase, causes a formation of an adrenergic agent selected from an alpha (e.g., $\alpha_1$, $\alpha_2$) receptor agonist, a beta (e.g., $\beta_1$, $\beta_2$, $\beta_3$) receptor agonist, an alpha receptor antagonist and a beta receptor antagonist. The adrenergic agents can modulate neurons and receptors involved in the actions of adrenaline and any neuronal or hormonal functions which are mediated or affected by adrenaline. Since noradrenaline can also act through alpha and beta receptors, the pharmacologically active agents can affect biological, chemical or physical processes associated with noradrenaline. In another embodiment, the adrenergic agent is a primary or secondary amine. Adrenergic agents include at least one member of the group selected from oxymetazoline, cirazoline, clonidine, A61603, agmatine, BRL 37344, BRL44408, cimaterol, dobutamine, efaroxan, HEAT, ICI 118551, ICI89406, ICL215001, idazoxan, procaterol, RX821002, SB206606, SR59230A, WB4101, xamoterol, ZD7114, efaroxan and clenbuterol (Tocris, Ellisville, Mo.); and adrenaline, brimonidine, and dipifevrin.

In yet another embodiment, hydrolysis of the compound of the invention, e.g., by reaction with a cholinesterase, causes formation of a noradrenergic agent selected from a norepinephrine re-uptake inhibitor and a norepinephrine releasing agent. The norepinephrine re-uptake inhibitor can prevent or minimize the removal of norepinephrine from a synapse, thereby increasing the amount of norepinephrine in the synapse. Prevention of norepinephrine removal can be active (e.g., by blocking a cellular process involved in re-uptake) or passive (e.g., by stabilizing norepinephrine). The norepinephrine agent can result in release of norepinephrine from a cell (e.g., a nerve cell, a secretory cell, an epithelial cell). Other compounds referred to herein as "re-uptake inhibitors" and "releasing agents," act in a similar manner, but specific for the particular pharmacologically active agent, such as a neurotransmitter. The norepinephrine re-uptake inhibitor can be, for example, viloxazine, and/or nisoxetine (Tocris, Ellisville, Mo.); maprotiline, atomoxetine, MCI225 (4-(2-Fluoro-phenyl)-6-methyl-2-piperazin-1-yl-thieno[2,3-d]pyrimidine hydrochloride), oxaprotiline, reboxetine, talopram, talsupram, and thionisoxetine; and amoxapine, desipramine, methylphenidate, nomifensine, nortriptyiline, and protriptyline (Sigma Chemical Co., St., Louis, Mo.).

In a further embodiment, hydrolysis of the compound of the invention, e.g., by reaction with a cholinesterase, causes formation of a serotonergic agent selected from a serotonergic antagonist, a serotonergic agonist, a serotonergic re-uptake inhibitor and a serotonin releasing agent. The serotonergic agents can, for example, affect neurotransmission or hormone release from endocrine glands. Serotonergic agents can include at least one member selected from quipazin, anpirtoline, N-(4-bromobenzyl)-5-methoxytryptamine, BW 723C86, 5-carboxamidotryptamine, m-CPP, N-desmethylclozapine, desmethylcitalopram, isamoltane, L-694247, MDL 72832, MDL 73005EF, alpha-methyl-5-hydroxytryptamine, 2-methyl-5-hydroxytryptamine, mianserin, MK212, 5-nonyloxytryptamine, 6-nitroquipazine, norfluoxetine, paroxetine, RS 67333, RS 67506, RS 23597-190, RS 39604, RU 24969, sertraline, desmethylsertraline, SR 57227, TFMPP, and fluvoxamine (Tocris, Ellisville, Mo.); and MMA1, RS17017 (1-(4-Amino-5-chloro-2-methoxy-phenyl)-5-piperidin-1-yl-pentan-1-one hydrochloride), RS 66331, SB271046 (5-Chloro-3-methyl-benzo[b]thiophene-2-sulfonic acid (4-methoxy-3-piperazin-1-yl-phenyl)-amide), SB 399885, and SL65.0155 (5-(8-Amino-7-chloro-2,3-dihydro-benzo[1,4]dioxin-5-yl)-3-(1-phenethyl-piperidin-4-yl)-3H-[1,3,4]oxadiazol-2-one hydrochloride).

In yet another embodiment, hydrolysis of the compound of the invention, e.g., by reaction with a cholinesterase, causes formation of a glutamatergic agent selected from an NMDA (N-methyl-D-aspartate) receptor agonist, an NMDA receptor antagonist, an NMDA glycine site agonist, an NMDA glycine site antagonist, an AMPA (α-amino-3-hydroxy-5-methyl-4-isoxazole proprionate) receptor agonist and an AMPA receptor antagonist, a kainate receptor agonist and a kainate receptor antagonist. Additionally, or alternatively, the glutamatergic agent can include an NMDA ion-channel modulator, an NMDA polyamine site agonist, an NMDA polyamine site antagonist, an AMPA/kainate agonist, an AMPA/kainate antagonist, a Group I metabotropic glutamate receptor agonist, a Group I metabotropic glutamate receptor antagonist, a Group II metabotropic glutamate receptor agonist, a Group II metabotropic glutamate receptor antagonist, a Group III metabotropic glutamate receptor agonist, a Group III metabotropic glutamate receptor antagonist, a quisqualate-sensitive AP6 site agonist, a quisqualate-sensitive AP6 site antagonist and an excitatory amino acid uptake inhibitor. Examples of metabotropic glutamate receptor compounds include 2-methyl-6-(phenylethynyl)-pyridine (MPEP), trans-ACPD, ACPT-I, ACPT-II, ACPT-III, tADA, AIDA, AP3, AP4, AP5, AP6, (2R,4R)-APDC, APICA, 3-carboxy-4-hydroxyphenylglycine, 4-carboxy-3-hydroxyphenylglycine, 4-carboxyphenylglycine, L-CCG-I, CHPG, CPPG, 1-cysteinesulfinic acid, DCG IV, 3,4-DCPG, 3,5-DHPG, E4CPG, EGLU, L-3'F2CCG-I, 1-glutamic acid, homoAMPA, 3-hydroxyphenylglycine, ibotenic acid, LY307452, LY341495, LY367385, MAP4, MCCG, MCPG, MPPG, MSOP, MSPG, MTPG, alpha-methyl-3-carboxymethylphenylglycine, o-phospho-1-serine, PPG, quisqualic acid, s-sulfo-1-cysteine, UBP1112, and spaglumic acid (Tocris, Ellisville, Mo.). Other glutamate receptor compounds include lamotrigine, riluzole, and salsolinol-1-carboxylic acid (Tocris, Ellisville, Mo.).

NMDA agents can include aspartic acid, D-cycloserine, ACBC, trans-ACBD, cis-ACPD, AP4, AP5, AP7, aspartic acid, 4-carboxyphenylglycine, CGP37849, CGP39551, CGS19755, CGP78608, chlorpheg, CPP, L-cysteinesulfinic acid, glutamic acid, glycine, HA-996, N-(4-hydroxyphenylacetyl)spermine, N-(4-hydroxyphenylpropanol)spermine, ibotenic acid, L689560, LY 235959, MK 801, NMDA, SDZ 220-040, SDZ 220-581, d-serine, (tetrazol-5-yl)glycine, memantine, spermine and spermidine (Tocris, Ellisville, Mo.); and amantadine (Sigma Chemical Co., St., Louis, Mo.). AMPA/kainate agents can include L-quisqualic acid, domoic acid, kainic acid, AMPA, ATPA, CFM-2, (S)-CPW 399, 5-fluorowillardiine, 5-iodowillardiine, willardiine, GAMS, GYKI, 52466, IDRA 21, SYM 2081, and SYM 2206 (Tocris, Ellisville, Mo.).

An excitatory amino acid uptake inhibitor can be dihydrokainic acid, cis-ACBD, L-CCG-II, chlorpheg, dihydrokainic acid, threo-3-hydroxyaspartic acid, threo-3-methylglutamic acid, MPDC, trans-2,4-PDC, SYM2081, and TBOA (Tocris, Ellisville, Mo.).

The NMDA receptor antagonist can be memantine (Tocris, Ellisville, Mo.) (Parsons, C. G., et al., *Neuropharmacol.*, 38:735-767 (1999), the teachings of which are hereby incorporated by reference in their entirety). The NMDA glycine receptor agonist can be D-cycloserine (Sigma Chemical Company, St. Louis, Mo.) (Land, C., et al., *Neurobiol. Learning Mem.*, 72:158-168 (1999), the teachings of which are hereby incorporated by reference in their entirety).

In a further embodiment, hydrolysis of the compound of the invention, e.g., by reaction with a cholinesterase, causes formation of a GABAergic agent which is selected from a GABAergic receptor antagonist, a GABAergic receptor agonist, a benzodiazepine site agonist, a benzodiazepine site antagonist, a benzodiazepine site inverse agonist and a GABA uptake inhibitor. The GABAergic can include, for example, muscimol, baclofen, saclofen, 1-amino-5-bromouracil, CACA, CGP35348 ((3-Amino-propyl)-diethoxymethyl-phosphinic acid), CGP46381 ((3-Amino-propyl)-cyclohexylmethyl-phosphinic acid), CGP 52432, CGP 54626, CGP 55845, GABA, GBLD 345, 2-hydroxysaclofen, isoguvacine, phaclofen, SB 205384, SCH 50911, SKF 97541, TACA THIP, TPMPA, and tracazolate (Tocris, Ellisville, Mo.); SR 95531 and SGS742 ((3-Amino-propyl)-butyl-phosphinic acid) (Kerr, D. I. B. et al., *J. Ong. Pharmac. Ther.* 67: 187-246 (1995); Froestl, W., et al., *Biochem. Pharmacol.*, 68:1479-1487 (2004)).

In another embodiment, hydrolysis of the compound of the invention, e.g., by reaction with a cholinesterase, causes formation of a dopaminergic agent selected from the group consisting of a dopaminergic antagonist, dopaminergic agonist, a dopaminergic re-uptake inhibitor, a dopaminergic releasing agent, and L-DOPA (levodopa) (3,4-dihydroxyphenylalanine, 3-hydroxytyrosine). Since dopamine is an intermediate in the synthesis of noradrenaline, adrenaline and melanin, any agent which affects dopamine can produce a physical, chemical or biological effect in biological processes associated with or mediated by noradrenaline, adrenaline and melanin. The dopaminergic agent can affect dopamine as a hormone or dopamine as a neurotransmitter. The dopaminergic agent can include, for example, dihydrexidine, A68930 (1-Aminomethyl-3-phenyl-isochroman-5,6-diol), SKF 38393, AJ 76, 4-phenyl-1,2,3,4-tetrahydroisoquinoline, and rimcazole (Tocris, Ellisville, Mo.); and A77636 (3-Adamantan-1-yl-1-aminomethyl-isochroman-5,6-diol), adrogolide, and SKF81297 (6-Chloro-1-phenyl-2,3,4,5-tetrahydro-1H-benzo[d]azepine-7,8-diol); pergolide (Sigma Chemical Company, St., Louis, Mo.) and pramipexole (also referred to as MIRAPEX™)

A "modulator," as used herein, refers to a compound that regulates, adjusts or adapts a biological pathway or receptor-mediated signal transduction pathway. The modulators can stimulate or inhibit a biological pathway or receptor-mediated signal transduction pathway. For example, an adenosine receptor modulator can increase the capacity of adenosine to bind the receptor, decrease the capacity of adenosine to bind the receptor, directly bind to the receptor (e.g., an agonist or inverse agonist) and have an effect or otherwise interact with the receptor to regulate, adjust or adapt a biological pathway associated with an adenosine receptor mediated signal transduction pathway.

In another embodiment, hydrolysis of the compound of the invention, e.g., by reaction with a cholinesterase, causes formation of at least one member selected from the group consisting of a mono-amine oxidase inhibitor, COMT (catechol-O-methyltransferase) inhibitor, beta secretase inhibitor or a gamma secretase inhibitor.

An inhibitor prevents an enzyme from participating in a biological process or diminishes the activity of the enzyme in the biological process. For example, a beta secretase inhibitor or a gamma secretase inhibitor can prevent the formation of beta-amyloid protein from amyloid precursor protein in the brain of a human. Accumulation of beta amyloid protein is associated with Alzheimer's disease in humans. Thus, a decrease in beta amyloid protein can ameliorate, prevent or diminish the onset or progression of Alzheimer's disease.

In a particular embodiment, the mono-amine oxidase inhibitor is at least one member selected from rasagiline (Kupsch, A., Curr. Opin. Investig. Drugs 3:794-979 (2002)), the teaching of which is hereby incorporated by reference in its entirety, 1-(benzofuran-2-yl)-2-propylaminopentane, 5-benzyloxy-2-indolylmethylamine, lazabemide, CHF3381 (2-(Indan-2-ylamino)-acetamide), milacemide, mofegeline, brofaromine, Ro-41-1049, RS-1636; and bifemelane, and tetrindol (Tocris, Ellisville, Mo.).

In another embodiment, hydrolysis of the compound of the invention, e.g., by reaction with a cholinesterase, causes formation of a potassium ion channel blocker, such as 4-amino pyridine. Since the selective permeability of a potassium channel is important to the resting membrane potential of a cell, blocking of a potassium ion channel can potentiate or prolong depolarization of a membrane, thereby augmenting cellular signaling, for example, of neurons.

The pharmacologically active agents can affect cells of the central nervous system, peripheral nervous system, autonomic nervous system and other tissues (e.g., smooth muscle, cardiac muscle, skeletal muscle) and organs (e.g., endocrine glands, exocrine glands).

In one embodiment, the pharmacologically active agent can be an exogenous agent (originating or produced outside of the individual). In another embodiment, the pharmacologically active agent can be an endogenous (originating or produced inside the individual) agent that has been purified from a biological source obtained from an individual.

The physical, chemical or biological effect that can be stimulated or inhibited by the compounds of the invention and, subsequently, the pharmacologically active agents of the invention can be between two or more cells. In one embodiment, the two or more cells are two or more nerve cells (pre-synaptic neuron, post-synaptic neuron). The nerve cells can be in the central nervous system, the peripheral nervous system or the autonomic nervous system. In another embodiment, the two or more cells can be at least one muscle cell (smooth muscle, skeletal muscle, cardiac muscle) and at least one nerve cell (pre-synaptic neuron, post-synaptic neuron). In still another embodiment, the two or more cells can be at least one nerve cell and at least one non-neuronal cell (e.g., a secretory cell of the adrenal medulla, a cell of an exocrine gland or endocrine gland, an epithelial cell of an organ or tissue). The two or more cells can be cells in vitro (e.g., cell culture) or cells in vivo (e.g., in an individual).

The pharmacologically active agent can be a nootropic agent (i.e., cognition enhancing agent), a neurotrophic agent (i.e., an agent which induces neuronal cell growth) and/or a neuroprotective agent.

In still another embodiment, the invention is a method of treating an individual. The method includes administering to the individual a compound of the invention. The compound inhibits a cholinesterase and, upon hydrolysis, e.g., by reaction with the cholinesterase, becomes at least a component of a pharmacologically active agent that treats the individual for a condition of the individual.

The pharmacologically active agent, QH, released by the compound of the invention is at least one member selected from the group consisting of a cholinergic agent, an adrenergic agent, a noradrenergic agent, a dopaminergic agent, a serotonergic agent, a glutamatergic agent, a GABAergic agent, a histaminergic agent, a mono-amine oxidase inhibitor, a COMT inhibitor, a beta secretase inhibitor, a gamma secretase inhibitor, a potassium channel blocker, a calcium channel blocker, an adenosine receptor modulator, a cannabinoid receptor modulator, a nootropic, a neuropeptide pathway modulator, a neurotrophic, a PDE IV inhibitor, a phosphatase/calcineurin inhibitor, a receptor trafficking regulator and a trace amine receptor modulator.

The compound of the invention can inhibit cholinesterase activity, which can be expressed as an IC50. The term "IC50," as used herein, refers to the concentration of a compound that inhibits an activity or effect by 50%, e.g., by reducing the frequency of a condition, such as memory or cognitive loss by 50%; by reducing binding of a competitor molecule to a protein (e.g., a receptor) by 50%; or by reducing the level of an activity (e.g., cholinesterase activity) by 50%.

As used herein, an "individual" is any mammal. A mammal can be a rodent (such as a rat, mouse or guinea pig), domesticated animal (such as a dog or cat), ruminant animal (such as a horse or a cow) or a primate (such as a monkey or a human). In a preferred embodiment, the individual is a human.

An individual suffering from a condition can be treated by the pharmacologically active agent. Said condition includes at least one condition selected from the group consisting of a central nervous system condition, a peripheral nervous system condition and an autonomic nervous system condition.

In a particular embodiment, the individual treated with the compounds of the invention has a central nervous system condition. A "central nervous system condition," as used herein, refers to any illness or ailment that affects the brain or spinal cord of the individual. Central nervous system conditions treated with the compounds of the invention, can, for example, be a consequence of a genetic disease, environmental exposure to a compound or secondary to a primary illness or disease. The central nervous system condition can be characterized by or a consequence of inadequate neurotransmitter release, synthesis, processing, re-uptake or cell signaling. The central nervous system condition can additionally, or alternatively, be characterized by or a consequence of failed or inadequate neuronal transmission due to disruptions in ion channels.

In a particular embodiment, the central nervous system condition is treated with a compound that includes a substituted stigmine or a substituted physostigmine. The compounds of the invention can be used to treat conditions including depression, anxiety and mental compounds of the invention can be Parkinson's disease, a memory impairment and a cognitive impairment.

The memory impairments can be in a human individual. Memory impairments that can be treated by the compounds of the invention include Alzheimer's disease, age-associated memory loss, an impairment in memory consolidation, an impairment in short term memory, mild cognitive impairment, an impairment in declarative memory and impairments in memory associated with or a consequence of multiple sclerosis and/or Parkinson's disease.

The memory impairment treated by the compounds of the invention can be a consequence of exposure to a muscarinic cholinergic receptor antagonist. In one embodiment, the muscarinic cholinergic receptor antagonist is atropine. In another embodiment, the muscarinic cholinergic receptor antagonist is scopolamine. In yet another embodiment, the muscarinic cholinergic receptor antagonist is homatropine.

A muscarinic cholinergic receptor antagonist includes any substance which blocks, diminishes, attenuates, inhibits, hinders, limits, decreases, reduces, restricts or interferes with the action of ACh thereby disrupting ACh-mediated cell signaling between presynaptic and postsynaptic neurons. The antagonist can, for example, oppose the action of ACh by acting in a manner which prevents ACh from binding to a muscarinic cholinergic receptor on a postsynaptic neuron, from mediating post-synaptic events following binding of ACh to a muscarinic cholinergic receptor, interfere with ACh degradation by acetylcholinesterase in the synaptic cleft or interfere with release of ACh from presynaptic neurons.

In still another embodiment, the compounds of the invention can be used to treat a peripheral nervous system condition in an individual. The peripheral nervous system condition can, for example, be a disease or illness consequent to or associated with neurons which supply innervation to a skeletal muscle (e.g., Myasthenia Gravis). Conditions of the peripheral nervous system can be, for example, an impairment in the release of acetylcholine from neurons at the neuromuscular junction of skeletal, smooth or cardiac muscle.

The compounds of the invention can be used to treat an autonomic nervous system condition (sympathetic nervous system, parasympathetic nervous system) in an individual. The autonomic nervous system conditions can be conditions which affect smooth muscle of viscera, glands (endocrine glands, exocrine glands), blood vessels or cardiac muscle. Autonomic nervous system conditions treated employing the compounds of the invention can be post-operative distension and urinary retention. Conditions of the autonomic nervous system can be an impairment in a function associated with the autonomic nervous system, for example, an impairment in the release of norepinephrine from sympathetic neurons or ACh from parasympathetic neurons at a synapse with a cell (e.g., epithelial, nervous, muscle, connective tissue) in an organ, blood vessel or gland. One skilled in the art would be capable of diagnosing an individual with a central nervous system condition, peripheral nervous system condition and an autonomic nervous system condition.

An "impairment in memory or cognition," as used herein, refers to a diminished capacity in memory and/or cognitive processes in the human. The cognitive and/or memory processes and impairments in cognitive and/or memory processes can be assessed or determined by established techniques. For example, memory can be assessed before, concomitantly with or after treatment of the individual with the compound of the invention one or more well established tests known to one of skill in the art. Such tests include the Passive Avoidance Testing (Principles of Neuropsychopharmacology), Feldman R. S., et al., Sinauer Assoc., Inc., Sunderland, Mass. (1997), the teachings of all of which are incorporated by reference in their entirety); Rey Auditory Verbal Learning Test (RAVLT) (L'examen clinique en psychologie), Rey A., Paris: Presses Universitaires de France (1964); a Wechsler Memory Scale; Wechsler Memory Scale-Revised (Wechsler, D., Wechsler Memory Scale-Revised Manual, NY, N.Y., The Psychological Corp. (1987)); California Verbal Learning Test-Second Edition (Delis, D. C., et al., The Californian Verbal Learning Test, Second Edition, Adult Version, Manual, San Antonio, Tex.: The Psychological Corporation (2000)); Cognitive Drug Research (CDR) Computerized Assessment Battery-Wesnes; Buschke's Selective Reminder Test (Buschke, H., et al., Neurology 24: 1019-1025 (1974)); Brief Visuospatial Memory Test-Revised; and Test of Everyday Attention (Perry, R. J., et al., *Neuropsychologia* 38: 252-271 (2000)).

In a particular embodiment, the memory of the human before, during or after administration of the compound of the invention is assessed or determined by a word recall test such as RAVLT.

In another embodiment, the invention described herein provides a method of treating a nervous system condition in an individual. The method includes administering to the individual a compound of the invention. The compound inhibits a cholinesterase thereby treating the nervous system condition of the individual. The compound, upon hydrolysis, e.g., by reaction with the cholinesterase, becomes at least a component of a pharmacologically active agent that further treats the nervous system condition in the individual. The pharmacologically active agent, QH, can, for example, sustain inhibition of the cholinesterase which was inhibited by the compound of the invention. The pharmacologically active agent can further treat the nervous system condition, for example, by delivering a compound to a neuron or synapse, sustaining polarization of a neuron, preventing re-uptake of a neurotransmitter, stimulating or maintaining the synthesis or release of a neurotransmitter.

In a particular embodiment, administration of the compound of the invention treats a central nervous system condition in an individual. The compound inhibits acetylcholinesterase thereby treating the central nervous system condition in the individual. The compound, upon hydrolysis, e.g., by reaction with the acetylcholinesterase, becomes at least one component of a pharmacologically active agent that further treats the central nervous system condition in the individual.

A further embodiment of the invention is a method of increasing acetylcholine in an in vitro sample. The method includes administering to the in vitro sample a compound. The compound inhibits a cholinesterase, thereby increasing acetylcholine in the in vitro sample. The compound, upon hydrolysis, e.g., by reaction with the cholinesterase, becomes at least a component of a pharmacologically active agent that further increases the acetylcholine in the in vitro sample.

The in vitro sample can be a cell-free sample or a sample containing cells. The cells employed can be mammalian cells (e.g., CHO cells), insect cells or bacterial cells. The method can be employed to assess the ability of the compound to inhibit cholinesterase and the pharmacologically active agent to affect biological, chemical or physical processes prior to use in an individual. The method can be packaged in a kit as an assay for screening the compounds of the invention for cholinesterase activity and pharmacological activity of the agents the compound becomes upon hydrolysis.

Another embodiment of the invention is a method of increasing acetylcholine in a tissue. The method includes administering to the tissue a compound of the invention. The compound inhibits a cholinesterase, thereby increasing acetylcholine in the tissue and, upon hydrolysis, e.g., by reaction with the cholinesterase, becomes at least a component of a pharmacologically active agent that further increases acetylcholine in the tissue.

The tissue can be a nervous tissue, a muscle tissue (cardiac, skeletal, smooth muscle) or a collection of any one or more of a tissue type selected from the group consisting of nervous tissue, muscle tissue, epithelial tissue and connective tissue. The tissue can be isolated (removed from the individual).

An additional embodiment of the invention is a method of increasing acetylcholine in an individual. The method includes administering to the individual a compound of the invention in the individual. The compound inhibits a cholinesterase (e.g., AchE, BuChE), thereby increasing acetylcholine. The compound, upon hydrolysis, e.g., by reaction with the cholinesterase, becomes at least a component of a pharmacologically active agent that further increases acetylcholine in the individual.

In one embodiment, the pharmacologically active agent increases acetylcholine in the central nervous system of the individual. In another embodiment, the pharmacologically active agent increases acetylcholine in the peripheral nervous system of the individual. In yet another embodiment, administration of the compound of the invention increases acetylcholine in the autonomic nervous system of the individual. Techniques to assess the increase of ACh in an in vitro sample, in a tissue and in an individual are well-known to one skilled in the art. (See, for example, Day, J. C., et al. *Methods* 23:21-39 (2001), the teachings of which are hereby incorporated by reference in its entirety).

The further increase in acetylcholine can be an increase mediated in a manner similar to the increase mediated by the compound of the invention (inhibition of AChE) or an increase in ACh by, for example, increasing the release of ACh, increasing the synthesis of ACh or otherwise preventing the inactivation of ACh.

In a further embodiment, the invention is a method of increasing transmission between two or more neurons. The method includes exposing the neurons to a compound of the invention. The compound inhibits a cholinesterase, thereby increasing transmission between the two or more neurons. The compound of the invention, upon hydrolysis, e.g., by reaction with the cholinesterase, becomes at least a component of a pharmacologically active agent that further increases transmission between the two or more neurons.

The further increase in transmission can be, for example, in a manner similar to the compound of the invention (by inhibiting cholinesterase) or by any other manner mediated by the pharmacologically active agent, such as stimulating release or synthesis of a neurotransmitter, inhibiting re-uptake of a neurotransmitter, alter ion channels of neurons.

The transmission can be increased between two or more neurons in vitro or in vivo. Techniques to determine an increase in transmission in vitro and in vivo are well known to one skilled in the art. For example, changes in depolarization of the post-synaptic neuron can be recorded by electrophysiological methods.

The compound of the invention can increase transmission between two or more neurons by, for example, increasing the amount of a neurotransmitter (e.g., cholinergic, adrenergic, noradrenergic, dopaminergic, serotonergic, glutamatergic, GABAergic, histaminergic) or diminishing or preventing the degradation of a neurotransmitter (e.g., by inhibiting monoamine oxidase, COMT) in the synapse. Additionally, or alternatively, the compound of the invention can increase transmission between two or more neurons, by modulating a neurotransmitter receptor (e.g., adenosine receptor, cannabinoid receptor, trace amine receptor) or blocking ion channels (e.g., potassium channel, sodium channel) in the neurons. Further, the compound of the invention can increase transmission between two or more neurons by inhibiting PDE IV, phosphatase/calcineurin inhibitor or regulating a receptor trafficking molecule, by inhibiting a phosphodiesterase or a phosphatase or by modulating receptor trafficking molecules (e.g., BARK, arrestin, ubiquitin E3 ligase).

An increase in transmission in an individual can minimize or alleviate central or peripheral nervous system conditions, such as memory and cognitive impairments. For example, an increase in cholinergic transmission (e.g., post-synaptic) in a human individual can minimize or alleviate the symptoms associated with Alzheimer's disease. An increase in dopaminergic transmission (e.g., post-synaptic) in a human individual can minimize or alleviate the symptoms associated with Parkinson's disease. A compound of the invention can, upon hydrolysis with a cholinesterase, become, for example, a dopaminergic agent which can increase transmission (pre- or post-synaptic) in the central nervous system in human individuals with Parkinson's disease, thereby providing an alternative to L-DOPA (Levodopa). The lipophilic phenyl carbamate, for example, of the compound of the invention can facilitate penetration of the compound through the blood brain barrier, thereby permitting delivery of a pharmacologically active agent, in particular, into the central nervous system. One skilled in the art can determine, using established techniques, the effect of the pharmacologically active agent on a human individual with a central or peripheral nervous system condition.

Another embodiment of the invention is a method of treating a cholinergic deficiency in an individual. The method includes administering to the individual a compound of the invention. The compound of the invention inhibits a cholinesterase thereby treating the cholinergic deficiency in the individual. The compound of the invention, upon hydrolysis, e.g., by reaction with the cholinesterase, becomes at least a component of a pharmacologically active agent that further treats the cholinergic deficiency in the individual. Further treatment can be, for example, by inhibition of AChE and/or BuChE, or by increasing release or synthesis of ACh.

The cholinergic deficiency can be a nervous system deficiency. For example, the compound of the invention can be used to treat a human individual having Alzheimer's disease. Presynaptic neurons degenerate rapidly in Alzheimer's disease which limits the efficacy of ChE inhibition as the disease progresses (Cutler, N. R., et al. *CNS Drugs* 3:467-481 (1995)). ChE continues to be present in the synapses of neurons in an individual with Alzheimer's disease, hydrolyzing what little ACh may be present in the synapse. Thus, the compounds of the invention can be become a cholinergic agonist thereby ameliorating the cholinergic deficiency by increasing ACh-mediated synaptic transmission in the central nervous system of individuals suffering from Alzheimer's disease, mild cognitive impairment, age associated memory impairment, age associated memory loss, natural aging, vascular dementia, dementia with Lewis bodies and/or Parkinson's disease.

In an additional embodiment, the invention is a method of treating an impairment in memory in an individual. The method includes administering to the individual a compound of the invention. The compound inhibits a cholinesterase thereby treating the impairment in memory in the individual. The compound, upon hydrolysis, e.g., by reaction with the cholinesterase, becomes at least a component of a pharmacologically active agent that further treats the impairment in memory in the individual. Further treatment of the memory can be treatment similar to the compound of the invention or in a manner different than the compound of the invention which is characteristic of the pharmacologically active agent.

The memory impairment can be a memory impairment selected from the group consisting of an impairment in memory consolidation, an impairment in long-term memory and an impairment in short-term memory. One skilled in the art would be capable of identifying an individual with a memory impairment and assessing the impairment.

In a particular embodiment, a human individual has an impairment in memory associated with a condition selected from the group consisting of Alzheimer's disease, Parkinson's disease, age-associated memory loss, mild cognitive impairment and multiple sclerosis.

In another embodiment the human individual treated with the compound of the invention has age-related cognitive decline.

A further embodiment of the invention is a method of delivering a pharmacologically active agent to a tissue. The method includes administering to the tissue a compound of the invention. The compound of the invention inhibits a cholinesterase and, upon hydrolysis, e.g., by reaction with the cholinesterase, becomes at least a component of a pharmacologically active agent, thereby delivering the pharmacologically active agent to the tissue.

The tissue can be an in vitro tissue sample or can be a tissue in vivo (in an individual). The tissue can be muscle tissue, nervous tissue or any combination of muscle, nervous, connective or epithelial tissue. The compound of the invention can be employed to deliver a pharmacologically active agent to a tissue that is proximal or distal to a tissue having a cholinesterase that is inhibited by the compound of the invention. For example, a compound of the invention can be employed to deliver a pharmacologically active agent, such as a cholinergic agent, to a muscle tissue. The compound of the invention can bind a cholinesterase (acetylcholinesterase, butyrylcholinesterase) thereby inhibiting the activity of the cholinesterase and, upon hydrolysis (with, for example, a cholinesterase), become a cholinergic agent. The pharmacologically active agent can be delivered to a muscle cell proximate to the site of binding of the compound of the invention to the cholinesterse or to a muscle cell distal to the site of binding. Similarly, the compound can bind to a cholinesterase in a neuron of the nervous system and deliver a cholinergic agent proximal or distal to the site of binding.

The compound of the invention can bind to a cholinesterase and, upon hydrolysis, e.g., by reaction with the cholinesterase, deliver, for example, a dopaminergic agent, serotonergic agent, adrenergic agent, noradrenergic agent, glutamatergic agent, GABAergic agent, histaminergic agent, monoamine oxidase inhibitor, COMT inhibitor, beta secretase inhibitor, gamma secretase inhibitor, potassium channel blocker, calcium channel blocker, adenosine receptor modulator, cannabinoid receptor modulator, nootropic, neuropeptide pathway modulator, neurotrophic, PDE IV inhibitor, phosphatase/calcineurin inhibitor, receptor trafficking regulator or trace amine receptor modulator to a neuron proximate or distal to the site of binding of the compound of the invention. Thus, the compounds of the invention provide a method of delivering a pharmacologically active agent to the central nervous system. The pharmacologically active agents can diffuse to varying regions of the brain and mediate their effects.

The invention includes a method of treating a condition of an individual by administering a compound of the invention, wherein the condition is a nervous system condition selected from delayed gastric emptying, attention deficit hyperactivity disorder (ADHD), phobia, sleep disorder, stroke, psychiatric disorder, pain, anticholinergic drug overdose, tobacco dependence, Parkinson's disease, memory impairment, and cognitive impairment. The invention includes use of a compound of the invention in the manufacture of a medicament for treating a condition of an individual, wherein the condition is a nervous system condition selected from delayed gastric emptying, attention deficit hyperactivity disorder (ADHD), phobia, sleep disorder, stroke, psychiatric disorder, pain, anticholinergic drug overdose, tobacco dependence, Parkinson's disease, memory impairment, and cognitive impairment.

The invention includes a method of treating a condition in an individual by administering a compound of the invention, wherein the condition is selected from glaucoma, oncologic condition, delayed gastric emptying, attention deficit hyperactivity disorder (ADHD), phobia, stroke, multiple sclerosis, sleep disorder, psychiatric disorder, pain, anticholinergic drug overdose, tobacco dependence, cardiovascular condition e.g., hypertension, bacterial infection, Meniere's disease, viral infection, allergies, and spasticity. The invention includes use of a compound of the invention in the manufacture of a medicament for treating a condition in an individual, wherein the condition is selected from glaucoma, oncologic condition, delayed gastric emptying, attention deficit hyperactivity disorder (ADHD), phobia, stroke, multiple sclerosis, sleep disorder, psychiatric disorder, pain, anticholinergic drug overdose, tobacco dependence, cardiovascular condition e.g., hypertension, bacterial infection, Meniere's disease, viral infection, allergies, and spasticity.

In one embodiment, the invention includes a method of treating a condition of an individual by administering a compound of the invention, wherein the condition is selected from delayed gastric emptying, attention deficit hyperactivity disorder (ADHD), phobia, sleep disorder, stroke, psychiatric disorder, pain, anticholinergic drug overdose, and tobacco dependence. The invention includes use of a compound of the invention in the manufacture of a medicament for treating a condition of an individual, wherein the condition is selected from delayed gastric emptying, attention deficit hyperactivity disorder (ADHD), phobia, sleep disorder, stroke, psychiatric disorder, pain, anticholinergic drug overdose, and tobacco dependence.

In one embodiment, the invention includes a method of treating a condition of an individual by administering a compound of the invention, wherein the condition is anticholinergic drug overdose. The invention includes use of a compound of the invention in the manufacture of a medicament for treating a condition of an individual, wherein the condition is anticholinergic drug overdose.

In one embodiment, the invention includes the methods discussed above, wherein the individual is a human.

The compounds of the invention can be employed in the methods, pharmaceutical compositions, kits and assays of the invention in a single dose or in multiple doses. The multiple doses can be administered as multiple doses in a single day, as a single daily dose administered for more than one day, as multiple doses administered daily for more than one day, or as a single dose on any given day followed or preceded by multiple doses in the intervening days. The multiple doses can be administered for a day, days, a week, weeks, a month, months, a year or years.

The compounds of the invention can be administered in the methods of the invention to an individual acutely (briefly or short-term) or chronically (prolonged or long-term). For example, the compounds of the invention can be used in methods to treat an individual by administering the compound of the invention to the individual once a day, multiple times (e.g., 2, 3, 4) in a day, for a day, days, a week, weeks, a month, months or years.

In one embodiment, the dose of the compound of the invention can be about 0.1 mg, about 1 mg, about 2.5 mg, about 5 mg, about 10 mg, about 15 mg, about 20 mg, about 25 mg, about 40 mg, about 50 mg, about 75 mg, about 90 mg, about 100 mg, about 150 mg, about 200 mg, about 250 mg, about 500 mg, about 750 mg or about 1000 mg.

In another embodiment, the dose of the compound of the invention can be between about 1 mg to about 100 mg; between about 2 mg to about 50 mg; or between about 5 mg to about 25 mg.

In still another embodiment, each dose of a multiple dose can be about 0.1 mg, about 1 mg, about 2.5 mg, about 5 mg, about 10 mg, about 20 mg, about 25 mg, about 40 mg, about 50 mg, about 75 mg, about 90 mg, about 100 mg, about 150 mg, about 200 mg, about 250 mg, about 500 mg, about 750 mg or about 1000 mg.

In a further embodiment, each dose of a multiple dose can be between about 1 mg to about 100 mg; between about 2 mg to about 50 mg; or between about 5 mg to about 25 mg.

The compound of the invention and the pharmacologically active agent are administered in the methods of the invention or employed in the assays and kits of the invention in an effective amount. The term "effective amount," "amount effective," or "therapeutically effective amount," when referring to the amount of the compound of the invention or pharmacologically active agent, is defined as that amount, or dose, of the compound or pharmacologically active agent that is sufficient for therapeutic efficacy (e.g., an amount sufficient to treat a nervous system condition in an individual; increase ACh in an in vitro sample, in a tissue or in an individual; increase transmission between two or more neurons; treat a cholinergic deficiency; treat an impairment in memory; treat an impairment in cognition; deliver a pharmacologically active agent to a tissue or an individual).

The compound of the invention can optionally be used in the methods, kits and assays of the invention with an acceptable carrier. The selection of an acceptable carrier will depend upon the method, kit or assay. For example, an acceptable carrier in an in vitro method, assay or kit can be saline, a suitable buffer or cell culture media.

The compound of the invention can be administered alone or as admixtures with conventional excipients, for example, pharmaceutically, or physiologically, acceptable organic, or inorganic carrier substances suitable for enteral or parenteral application which do not deleteriously react with the compound employed in the method. Suitable pharmaceutically acceptable carriers include water, salt solutions (such as Ringer's solution), alcohols, oils, gelatins and carbohydrates such as lactose, amylose or starch, fatty acid esters, hydroxymethycellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances which do not deleteriously react with the compounds employed in the methods of the invention. The preparations can also be combined, when desired, with other active substances to reduce metabolic degradation.

Preferred methods of administration of the compounds of the invention are oral administration (such as a tablet or capsule). The compound alone, or when combined with an admixture, can be administered in a single or in more than one dose over a period of time to confer the desired effect (e.g., improve a nervous system condition, increase acetylcholine, increase transmission between two or more neurons, treat a cholinergic deficiency, treat a memory impairment, treat a cognitive impairment, deliver a pharmacologically active agent).

The compounds of the invention can be administered to a target site in an individual. The target site selected can depend on the condition to be treated. For example, a local injection in a skeletal muscle (the target site) can be employed to treat a peripheral nervous system condition, or local injection in the cerebral spinal fluid, sinuses or ventricles of the brain (target sites) can be employed to treat a central nervous system condition. In another example an eye drop, an ointment, a gel or an ocular injection containing the compound can be employed to treat glaucoma in an individual.

When parenteral application is needed or desired, particularly suitable admixtures for the compounds are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampules are convenient unit dosages. The compounds are employed in the methods, assays or kits of the invention can also be incorporated into liposomes or administered by transdermal pumps or patches. Pharmaceutical admixtures suitable for use in the present invention are well-known to those of skill in the art and are described, for example, in Pharmaceutical Sciences (17th Ed., Mack Pub. Co., Easton, Pa.) and WO 96/05309, the teachings of which are hereby incorporated by reference.

The dosage and frequency (single or multiple doses) administered to an individual can vary depending upon a variety of factors, including, for example, the nervous system condition to be treated, the type of cholinergic deficiency in the individual, the duration of the nervous system condition, the degree of memory impairment (e.g., impairment in memory consolidation, impairment in short-term memory), the degree of cognitive impairment (e.g., attention, alertness, executive function, wakefulness, arousal, vigilance, executive function, reaction time), the pharmacologically active agent to be delivered or cognition; size, age, sex, health, body weight, body mass index and diet of the individual; nature and extent of symptoms of the condition or impairment in memory or cognition, kind of concurrent treatment, complications from the condition or impairment, or other health-related problems of the human being treated.

Other therapeutic regimens or agents can be used in conjunction with the methods and compounds of the invention employed in the methods of the invention. Adjustment and manipulation of established dosages (e.g., frequency and duration) are well within the ability of those skilled in the art.

Representative compounds of the invention include but are not limited to:

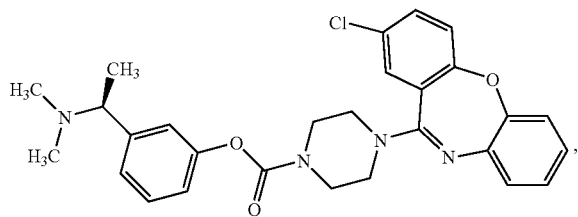
(3)

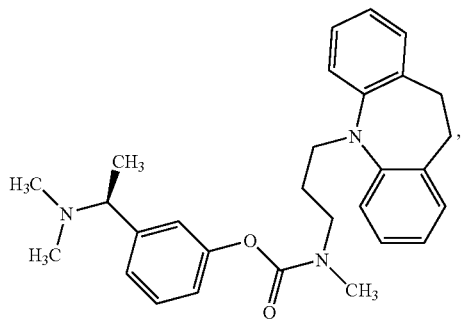
(4)

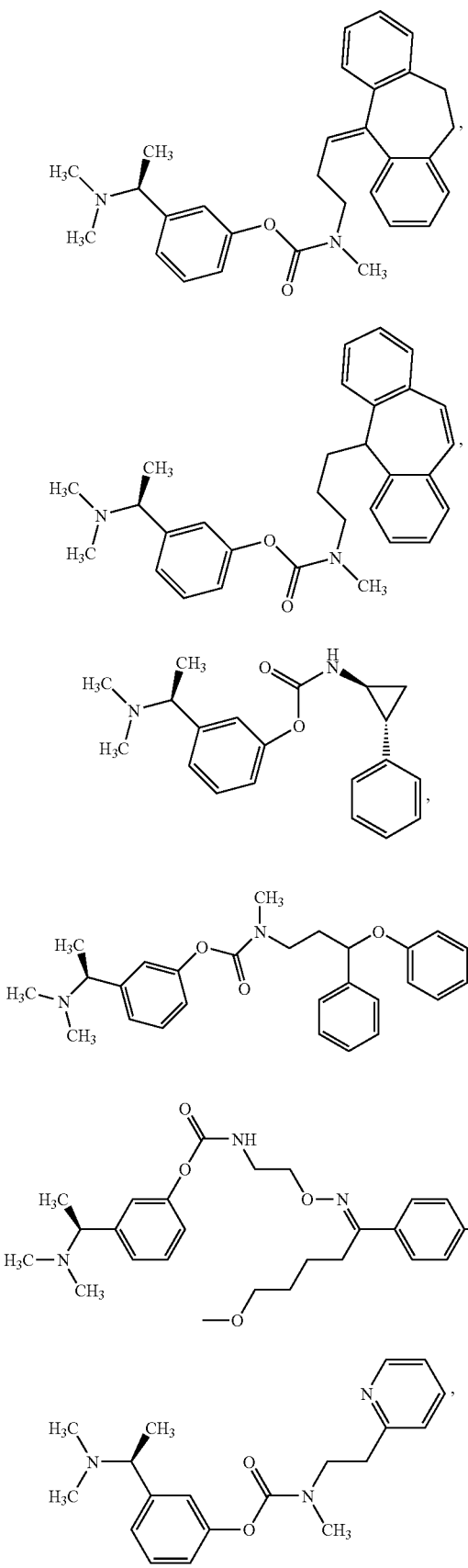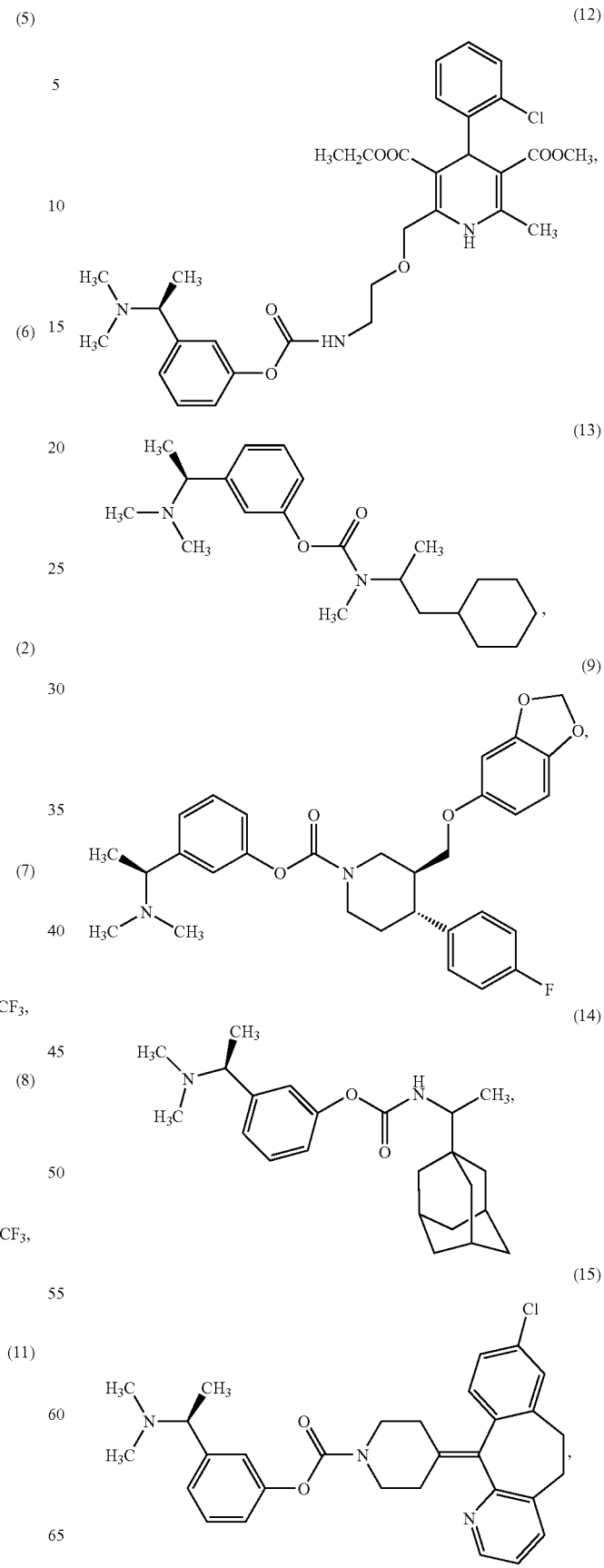

(10)
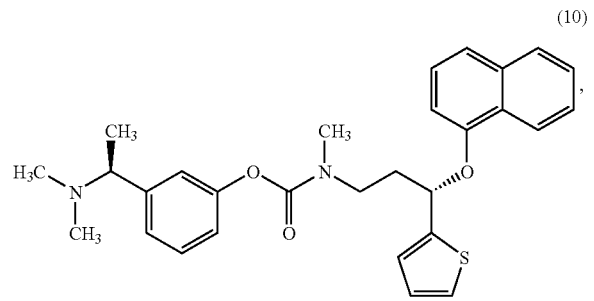
(16)
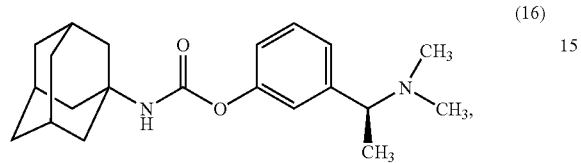
(17)
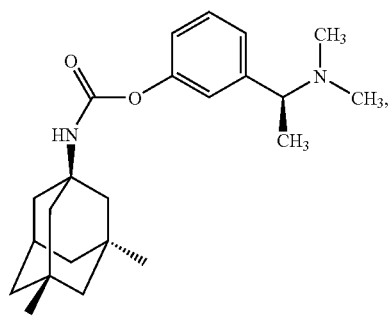
(18)
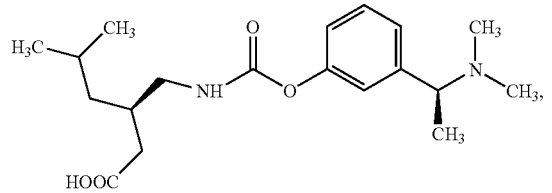
(19)
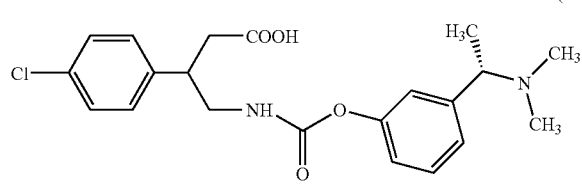
(20)
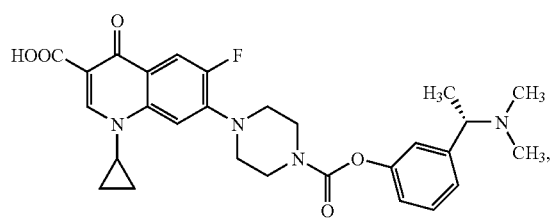
(21)
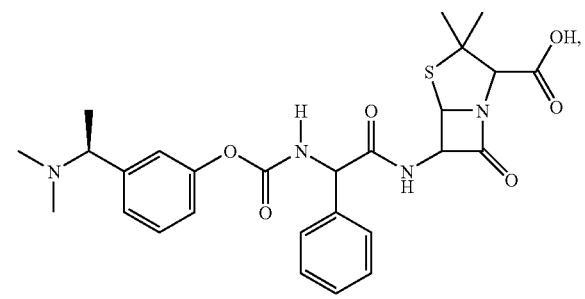
(22)
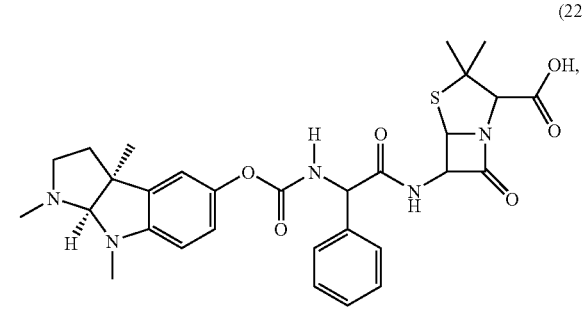
(23)
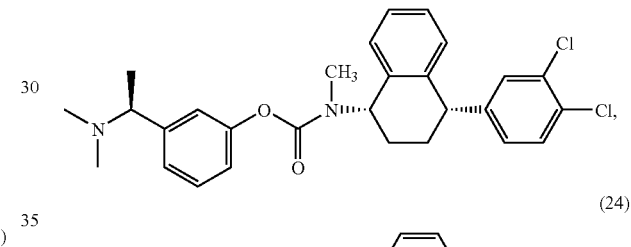
(24)
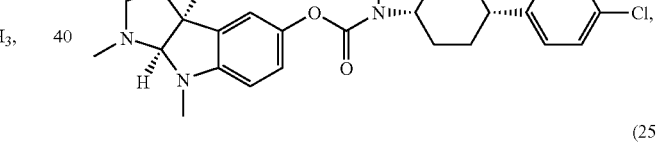
(25)
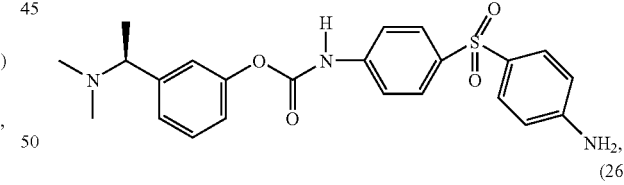
(26)
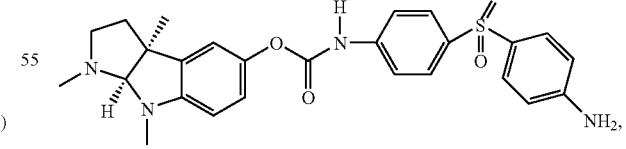
(27)
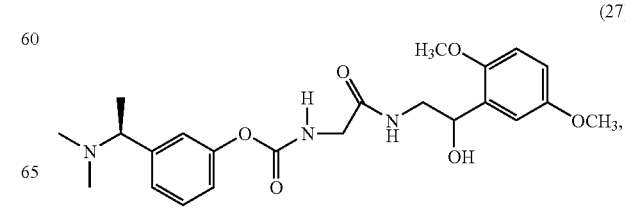

(28)

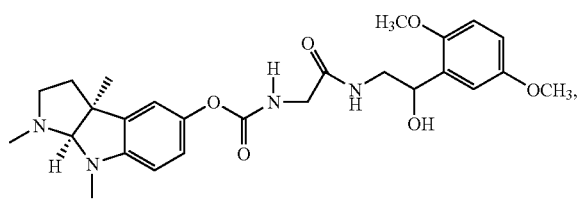

(29)

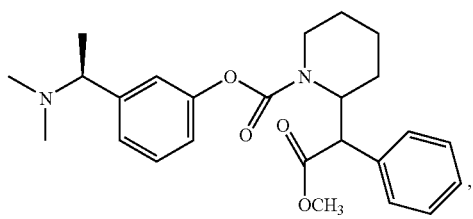

(30)

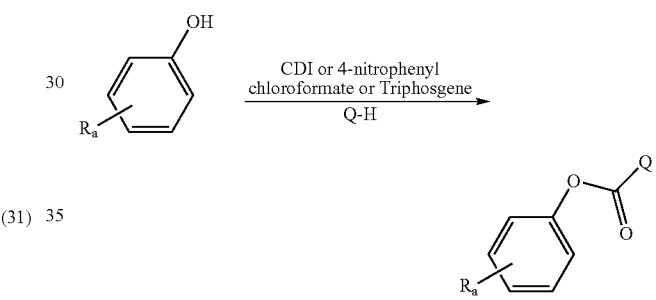

(31)

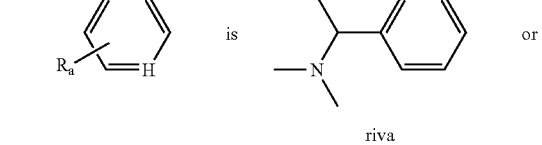

The compounds of the invention were evaluated as follows:

Acetylcholinesterase activity of compound of the invention was determined at 25° C. by a modification of the colorimetric method of Ellmann, et al. (*Biochem. Pharmacol.*, 7:88-95 (1961)). The enzyme, compound, and buffer were preincubated for 30 minutes. At the end of the preincubation period, the substrate acetylthiocholine was added. The final assay mixture contained 10 mM Tris-buffer (pH 8), 0.3 mM Acetylthiocholine and 0.33 mM DTNB and 0.08 U/ml enzyme. At least five (5) different concentrations of the compound were assayed per $IC_{50}$ experiment.

Hydrolysis of acetylthiocholine was monitored indirectly by measurement of the formation of the conjugate between thiocholine and DTNB.

To assess the effects of the compounds of the invention on scopolamine-induced amnesia, rats are injected with saline or scopolamine hydrochloride (0.75 mg/kg) 30 minutes prior to training on the Inhibitory Avoidance task. Immediately following the training trial, rats are injected with saline or compound. Retention for the task in scopolamine or saline treated rats, is assessed 24 hours later.

An in vitro screening assay with compounds of the invention was completed according to the methods described in Ellman G L et al., *Biochem Pharmacol.*, 7:88-95 (1961) and in Nadarajah B, *J. Anal. Toxicol.*, 16:192-193 (1992), both of which are herein incorporated by reference in their entireties.

The induction of hypothermia was determined for compounds of the invention according to the methods described in Freedman, et al., *European Journal of Pharmacology*, 187 (1990), 193-199, which is incorporated by reference herein. Dose range and time course for cholinergic effects of the compounds of the invention was also determined.

The present invention is further illustrated by the following examples, which are not intended to be limiting in any way.

EXAMPLES

Example 1

Compound Synthesis

Compounds of the invention are produced by coupling of $R_a$-phenol and Q-H using methods known to those skilled in the art. For example,

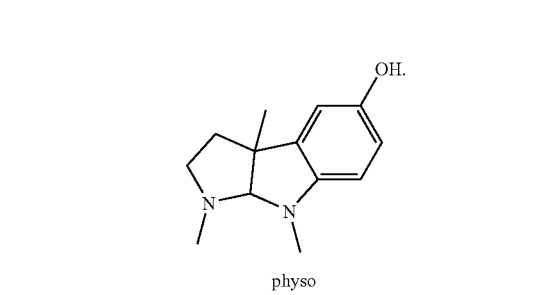

wherein $R_a$ represents the appropriate phenyl substituents for a stigmine, such as rivastigmine or physostigmine, and Q represents an amine-containing pharmacologically active agent. For example, Exemplary compounds are shown in Table A.

TABLE A

| Starting material | Reagents/conditions | Results |
|---|---|---|
| Desipramine (300 mg, 1.0 mmol)<br>Q = P<br>$R_1$ = $CH_3$ | Desipramine is treated with sodium bicarbonate and riva carbamate imidazole solution (2.0 mmol, 2.0 eq.) in dichloromethane (8 mL). | 4 (240 mg, 52% yield, >95% by HPLC.) isolated by column chromatography. |
| Fluvoxamine maleate (100 mg, 0.23 mmol)<br>Q = S<br>$R_1$ = H | Fluvoxamine is treated with sodium bicarbonate and riva carbamate imidazole solution (0.66 mmol, 3.0 eq.) in dichloromethane (7 mL). | 8 (10 mg, 8% yield, 90% purity by HPLC) isolated by preparative TLC. |
| Fluoxetine hydrochloride (100 mg, 0.29 mmol)<br>Q = R<br>$R_1$ is $CH_3$ | Fluoxetine is treated with diisopropylethylamine (0.63 mmol, 2.2 eq.) and riva carbamate imidazole solution (0.63 mmol, 2.2 eq) in dichloromethane (6 mL). | 7 isolated by preparative TLC to give 30 mg, 20% yield, 80% purity by HPLC. |
| Betahistine dihydrochloride (400 mg, 1.9 mmol)<br>Q = Z<br>$R_1$ is $CH_3$ | Betahistine is treated with diisopropylethylamine (4.0 mmol, 4.2 eq.) and riva carbamate imidazole solution (4.0 mmol, 4.2 eq) in dichloromethane (6 mL). | 11 HPLC showed 16% of desired product. |
| Paroxetine (87 mg, 0.26 mmol)<br>Q = Y<br>$R_1$ is absent | Riva carbamate soln in dichloromethane (S-rivastigmine coupled with carbonyldiimidazole) 1.2 mmol., dichloromethane (4 mL) | 9 (49 mg, 83% purity). |
| Ampicillin (150 mg, 0.43 mmol)<br>Q = SS<br>$R_1$ is H | Ampicillin is treated with diisopropylethylamine (2 mmol, 5.0 eq.) and riva carbamate imidazole solution (1 mmol, 2.5 eq.) in dichloromethane (5 mL). | 21 |
| Ampicillin (150 mg, 0.43 mmol)<br>Q = SS<br>$R_1$ is H | Ampicillin is treated with diisopropylethylamine (2 mmol, 5.0 eq.) and physo carbamate imidazole solution (1 mmol, 2.5 eq.) in dichloromethane (5 mL). | 22 |
| Sertraline maleate (250 mg, 0.73 mmol)<br>Q = JJJ<br>$R_1$ is $CH_3$ | Sertraline is treated with sodium bicarbonate and riva carbamate imidazole solution (1.5 mmol, 2.05 eq.) in the presence of diisopropylethylamine (2.87 mmol, 3.9 eq.) in dichloromethane (15 mL). | 23 |
| Sertraline maleate (250 mg, 0.73 mmol)<br>Q = JJJ<br>$R_1$ is $CH_3$ | Sertraline is treated with sodium bicarbonate and physo carbamate imidazole solution (1.5 mmol, 2.05 eq.) in the presence of diisopropylethylamine (2.87 mmol, 3.9 eq.) in dichloromethane (15 mL). | 24 |
| Dapsone (250 mg. 1 mmol)<br>Q = YY<br>$R_1$ is H | Riva carbamate soln. (1 mmol), diisopropylethylamine (1.2 mmol), dichloromethane (9 mL) | 25 |
| Dapsone (250 mg. 1 mmol)<br>Q = YY<br>$R_1$ is H | Physo carbamate soln. (1 mmol), diisopropylethylamine (1.2 mmol), dichloromethane (9 mL) | 26 |
| Midodrine HCl (125 mg, 0.4 mmol)<br>Q = EEE<br>$R_1$ is H | Riva carbamate soln (0.5 mmol), dichloromethane (4 mL), diisopropylethylamine (1.2 mmol) | 27 |
| Midodrine HCl (125 mg, 0.4 mmol)<br>Q = EEE<br>$R_1$ is H | Physo carbamate soln (0.5 mmol), dichloromethane (4 mL), diisopropylethylamine (1.2 mmol) | 28 |
| Baclofen (200 mg, 0.94 mmol)<br>Q = UU<br>R1 is H | Riva carbamate soln (1.1 mmol), dichloromethane (7 mL), diisopropylethylamine (2.4 mmol) | 19 (5%), urea derivative (26%) and two additional peaks. |
| Betahistine di-HCl (418 mg, 2.0 mmol)<br>Q = Z<br>$R_1$ is $CH_3$ | Betahistine is treated with 2.0 M aq. soln. of $Na_2CO_3$, dried and concentrated, react with the carbamate soln (8 mL of 0.25 M soln in dichloromethane, dichloromethane (2 mL). | 11 was purified on a silica column, being dried under high vacuum. |
| Amlodipine (410 mg, 1.0 mmol)<br>Q = AA<br>$R_1$ is H | Riva carbamate soln (4 mL of 0.25 M soln in dichloromethane), dichloromethane (6 mL) | 12 LC/MS showed the product mass corresponding to the product (30%). |
| Methylphenidate HCl (270 mg, 1.0 mmol) | 1)Methylphenidate is treated with 2.0 M aq. soln. of $Na_2CO_3$, dried and concentrated, riva carbamate soln | 29 |

TABLE A-continued

| Starting material | Reagents/conditions | Results |
|---|---|---|
| Q = FFF<br>R₁ is absent | (2.4 mL of 0.25 M soln in dichloromethane), dichloromethane (2 mL)<br>2) diisopropylethylamine (130 mg, 1.0 mmol) added and stirred | |
| Methylphenidate HCl (270 mg, 1.0 mmol)<br>Q = FFF<br>R₁ is absent | 1) Methylphenidate is treated with 2.0 M aq. soln. of Na₂CO₃, dried and concentrated, react with physo carbamate soln (2.4 mL of 0.25 M soln in dichloromethane), dichloromethane (2 mL)<br>2) diisopropylethylamine (130 mg, 1.0 mmol) added and stirred | 30 |
| Gabapentin (100 mg, 0.58 mmol)<br>Q = CCC<br>R₁ is H | Chlorotrimethylsilane (0.58 mmol), carbonyldiimidazole (0.58 mmol), (S)-rivastigmine phenol (0.58 mmol), triethylamine (1.2 mmol), acetonitrile (0.5 mL), CHCl₃ dichloromethane (2.5 mL) | 31 25 mg of the desired product and 21 mg of TFA salt of the desired product were isolated using preparative HPLC. |
| Protriptyline HCl (2 g, 6.67 mmol)<br>Q = U<br>R₁ is CH₃<br>Protriptyline conjugate (1.15 g, 2.5 mmol) | Carbonyldiimidazole (6.67 mmol), (S)-rivastigmine phenol (6.67 mmol), diisopropylethylamine (10.0 mmol), dichloromethane (60 mL)<br>1.0 M HCl in ether (4.5 mL), CHCl₃ (10 mL) | 6 Purified twice on silica column chromatography to give 1.15 g of the desired product (HPLC purity >99%).<br>1.21 g of the desired product was isolated (HPLC purity >99%). |
| Fluoxetine HCl (2 g, 6 mmol)<br>Q = R<br>R₁ is CH₃<br>Fluoxetine conjugate (1.05 g, 2.1 mmol) | Carbonyldiimidazole (6 mmol), (S)-rivastigmine phenol (6 mmol), diisopropylethylamine (9 mmol), dichloromethane (40 mL)<br>1.0 M HCl in ether (4.5 mL), CHCl₃ (10 mL) | 7 Purified on a silica column chromatography to give 1.05 g of the desired product (HPLC purity >99%)<br>970 mg of the desired product was isolated (HPLC purity >99%). |
| Duloxetine (740 mg, 2.5 mmol)<br>Q = T<br>R₁ is CH₃ | Carbonyldiimidazole (2.6 mmol), (S)-rivastigmine phenol (2.7 mmol), dichloromethane (10 mL) | 10 |
| Fluvoxamine maleate (434 mg, 1 mmol)<br>Q = S<br>R₁ is H | Carbonyldiimidazole (1.05 mmol), (S)-rivastigmine phenol (1.1 mmol), diisopropylethylamine (3 mmol), dichloromethane (6 mL) | 8 LC/MS of the reaction mixture showed the mass of the product. |
| Fluvoxamine maleate (2.5 g, 5.7 mmol)<br>Q = S<br>R₁ is H | Carbonyldiimidazole (6.05 mmol), (S)-rivastigmine phenol (6.3 mmol), diisopropylethylamine (17.3 mmol), dichloromethane (40 mL) | 8 LC/MS of the reaction mixture showed the mass of the product. |

Example 2

Preparation of Hydrochloride Salts

Example 2A: A compound of the invention is dissolved in chloroform (3 ml per mmol compound). A solution of 1M HCl in ether (1.5-2 molar equivalents) is added dropwise at 0° C. Upon completion of addition of hydrochloric acid, the mixture is allowed to warm to room temperature. Solvents are removed by evaporation and the residue dried under vacuum to yield the hydrochloride salt of the compound.

Example 2B: A compound is dissolved in water and adjusted to a pH of ~10 using 2.0 M aq. solution of Na₂CO₃. The compound is then extracted with dichloromethane (2×30 mL), dried (Na₂SO₄) and concentrated. The residue is passed through a silica column using heptanes (74%), ethyl acetate (25%) and triethylamine (1%) as the solvent. The fractions are evaporated using a rotovap and dried under high vacuum overnight. The residue is taken up in water (6 mL), followed by the addition of 2.0 M HCl (3 mL). The solution is then lyophilized to give the compound as its HCl salt.

Example 3

Inhibition of Acetylcholinesterase In Vitro

All reagents employed in these experiment were of analytical grade. Acetylthiocholine iodide and 5,5'-dithiobis-(2-nitro)benzoic acid (DTNB) and human recombinant acetylcholinesterase (C1682) were purchased from e.g., Sigma Chemical Co (St. Louis, Mo.).

Acetylcholinesterase activity of compound of the invention was determined at 25° C. by a modification of the colorimetric method of Ellmann, et al. (*Biochem. Pharmacol.,* 7:88-95 (1961)). The enzyme, compound, and buffer were preincubated for 30 minutes. At the end of the preincubation period, the substrate acetylthiocholine was added. The final assay mixture contained 10 mM Tris-buffer (pH 8), 0.3 mM Acetylthiocholine and 0.33 mM DTNB and 0.08 U/ml enzyme. At least five (5) different concentrations of the compound were assayed per $IC_{50}$ experiment.

Hydrolysis of acetylthiocholine was monitored indirectly by measurement of the formation of the conjugate between thiocholine and DTNB. Optical density at 405 nm was-recorded during 5 minutes employing a microplate spectrophotometer and plotted against time. The inverse of the initial rates for a range of inhibitor concentrations was plotted against concentration (Dixon Plot) to give the $IC_{50}$ value (the concentration at which enzyme activity is inhibited by 50%) as the opposite value of the x-intercept (Burlingham, et al., *J. Chem. Ed.*, 80:214-218 (2003)).

The results are summarized as follows:

| Cmpd # | Name | Compound Structure | AChE IC50 (μM) |
|---|---|---|---|
| 1 | S-rivastigmine | 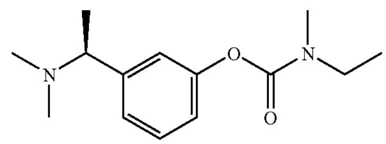 | 35.5 |
| 1A | Physostigmine | 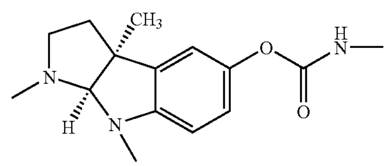 | 0.07 |
| 2 | S-riva tranylcypromine | 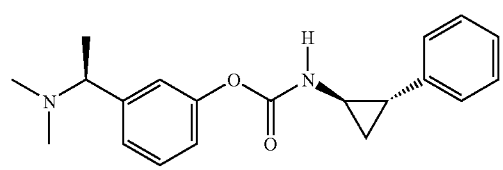 | 0.2 |
| 3 | S-riva-amoxapine | 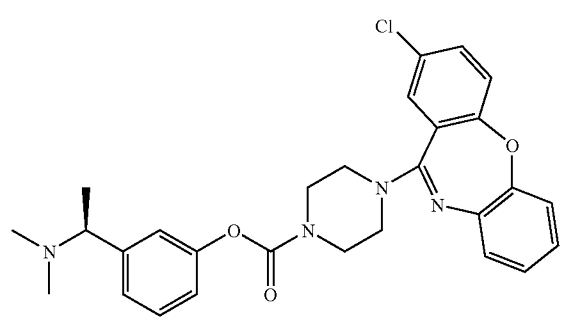 | 20.9 |
| 4 | S-riva-desipramine | 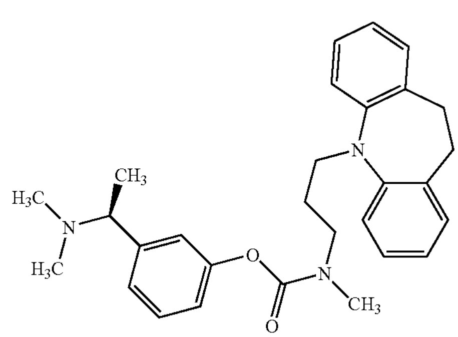 | 0.2 |

-continued

| Cmpd # | Name | Compound Structure | AChE IC50 (μM) |
|---|---|---|---|
| 5 | S-riva-nortriptyline | 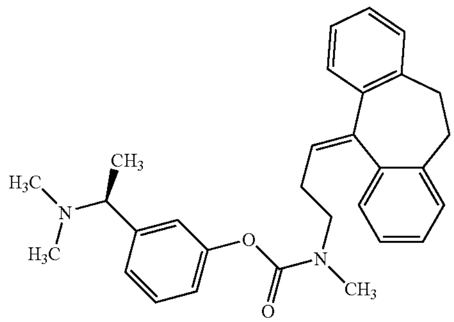 | 0.5 |
| 6 | S-riva-protriptyline | 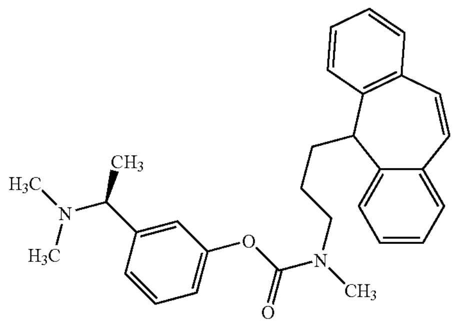 | 0.5 |
| 7 | S-riva fluoxetine | 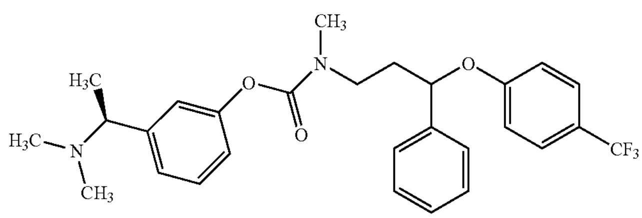 | 4.8 |
| 8 | S-riva fluvoxamine | 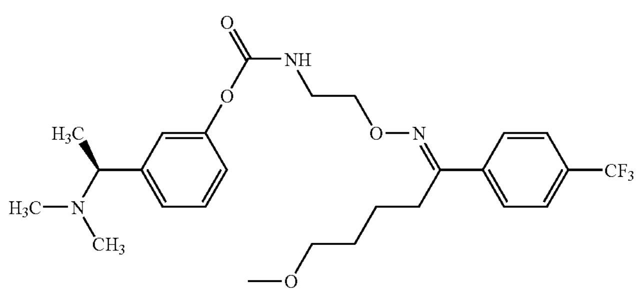 | 6.1 |
| 9 | S-riva paroxetine | 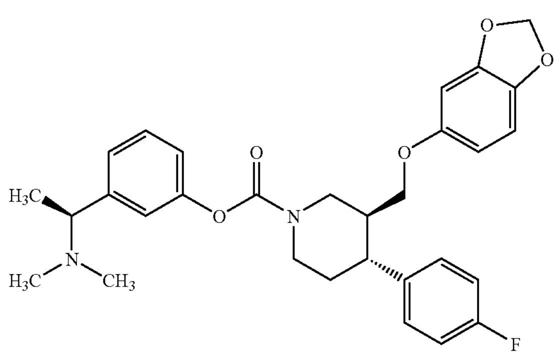 | 9.5 |

-continued
| Cmpd # | Name | Compound Structure | AChE IC50 (μM) |
|---|---|---|---|
| 10 | S-riva duloxetine | 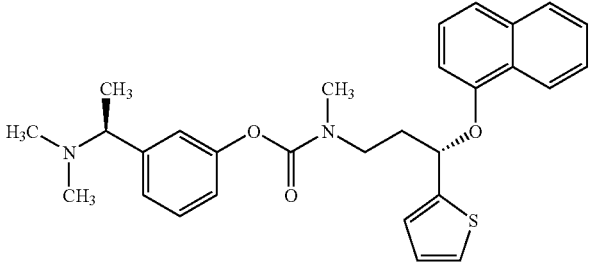 | 0.2-0.5 |
| 11 | S-riva betahistine | 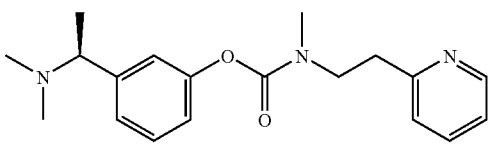 | 13.3 |
| 12 | S-riva amplodipine | 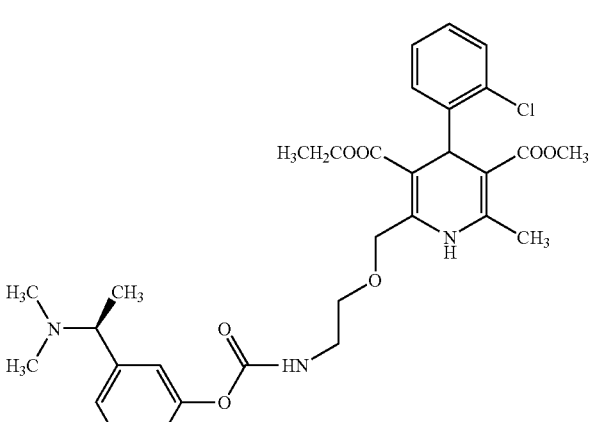 | 3.7 |
| 13 | S-riva propylhexedrine | 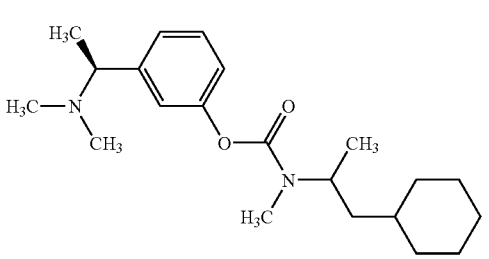 | 0.9 |
| 14 | S-riva-rimantadine | 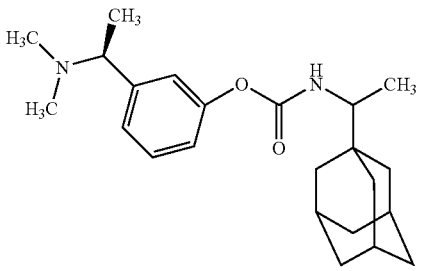 | 4.5 |

| Cmpd # | Name | Compound Structure | AChE IC50 (μM) |
|---|---|---|---|
| 15 | S-riva-desloratidine | 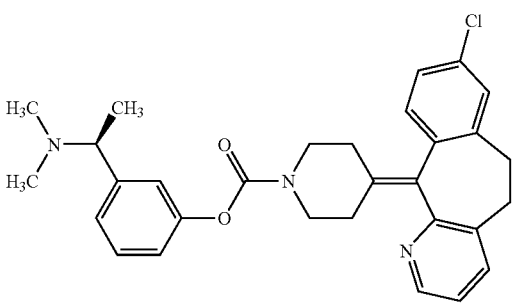 | 12.5 |
| 16 | S-riva-amantadine | 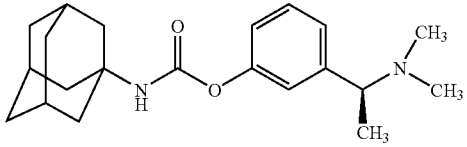 | 72.1 |
| 17 | S-riva memantine | 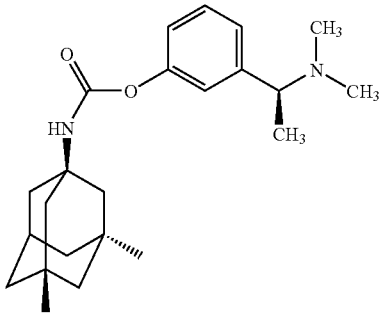 | 5.8 |
| 18 | S-riva pregabalin | 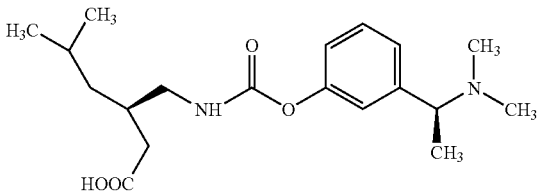 | 24.9 |
| 19 | S-riva baclofen | 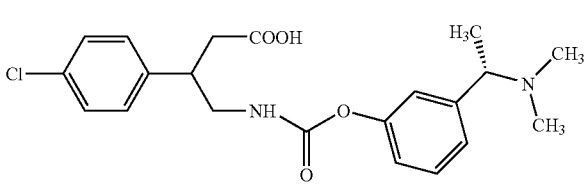 | 16.9 |
| 20 | S-riva ciprofloxacin | 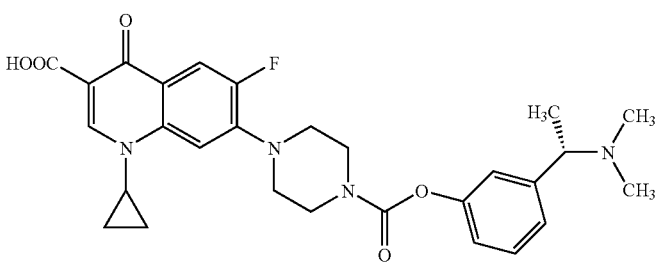 | 53.6 |

These data show that the compounds of the invention inhibit acetylcholinesterase in vitro. Inhibition of acetylcholinesterase by compounds of the invention can be greater than inhibition of acetycholinesterase by a stigmine, such as rivastigmine. Compounds synthesized from stigmines resulted in similar or increased activity compared to the stigmine. Thus, structural alterations in stigmines, compounds with known enzymatic activity, did not decrease or inhibit the enzymatic activity of the stigmine.

Example 4

Inhibition of Cholinesterase in Brain

Male Wistar rats are injected intraperitoneally (i.p.) with rivastigmine or a compound of the invention. The cholinergic behavioral effect is observed in the animals. Animals are decapitated 3 hours after injection and the brains are rapidly removed. The brain tissue is diced into small pieces, placed on ice and immediately homogenized with a Polytron PT1200 (Kinematic AG) in 10 ml ice cold Tris with 0.1% Triton-X and protease inhibitors. The protease inhibitors in the extraction buffer are Antipain (10 M), Aprotinin (5 TIU/mg protein), Bestatin (60 nm), Leupeptin (10 M) and Pepstatin (1 M). The final dilution of the homogenate in the final assay mixture is 120-fold.

Total cholinesterase activity is determined by a modification of the colorimetric method of Ellmann, et al. (*Biochem. Pharmacol.*, 7:88-95 (1961)), as described above. Hydrolysis of acetylthiocholine is monitored indirectly by measurement of the formation of the conjugate between thiocholine and DTNB. Optical density at 405 nm is recorded during five (5) minutes employing a a microplate spectrophotometer and plotted against time. The initial rates are calculated from the slope of the linear portion of the graph.

Cholinesterase activity is normalized for protein content of the homogenate. Relative cholinesterase activity is calculated as the ratio of normalized cholinesterase activity in a rat treated with a control compound or a compound of the invention over normalized cholinesterase activity in saline treated rats.

Example 5

Alleviation of Scopolamine Induced Amnesia in Multiple Trial Passive Avoidance Assay Inhibitory avoidance is used as a cognitive performance screen because the discrete nature of the task allows for precise pharmacological manipulation and for the ability to selectively study acquisition, consolidation, or recall or learned information. This task is widely used to assess the facilitory effects of centrally acting drugs in both normal, untreated animals, and in animals made amnestic by the use of scopolamine, a muscarinic cholinergic receptor antagonist that produces marked amnesia.

The inhibitory avoidance apparatus used in these experiments consists of a light chamber and a dark chamber, which are joined by means of a sliding guillotine door. Training involved placing a rat inside the light chamber with its head facing away from the door. Ten seconds later, the sliding door is opened, and the latency to enter the dark chamber is recorded (100 second maximum). When the rat enters the dark chamber, it receives a continuous footshock (0.4 mA) through the metal grid floor until it returns to the light chamber. This sequence of events continues until the rat remains in the light chamber for a period of 100 consecutive seconds or until a maximum of 5 footshocks have been received.

Retention testing, or the ability of the rat to remember the previous events in the inhibitory avoidance apparatus, is conducted 24 hours after the initial testing. The rat is placed into the light chamber with its head facing away from the door. Ten seconds later, the door is opened, allowing the rat access to the dark chamber. No footshock is administered during retention testing. Latency to enter the dark chamber is recorded (900 seconds maximum) and used as a measure of memory.

To assess the effects of the compounds of the invention on scopolamine-induced amnesia, rats are injected with saline or scopolamine hydrochloride (0.75 mg/kg) 30 minutes prior to training on the Inhibitory Avoidance task. Immediately following the training trial, rats are injected with saline or compound.

Retention for the task in scopolamine or saline treated rats, is assessed as described above, 24 hours later. No compound (drug) is administered to the rat prior to the retention test and no shock was given during retention testing. For retention testing, the rat is placed into the light chamber. Fifteen seconds later, the door is automatically opened and latency to enter the dark compartment is measured. The latency to enter the dark chamber is the primary measure of memory on this task. Compounds of the invention are evaluated in this protocol. Compounds and rivastigmine (control) are injected i.p. into rats. The dose that increases the latency the most i.e., the effective dose for each compound, the performance relative to the unimpaired (saline) control group as well as the performance relative to the impaired (scopolamine) group at the most effective dose is determined.

Example 6

In Vitro Screening

An in vitro screening assay with compounds of the invention was completed according to the methods described in Ellman G L et al., Biochem Pharmacol., 7:88-95 (1961) and in Nadarajah B, J. Anal. Toxicol., 16:192-193 (1992), both of which are herein incorporated by reference in their entireties. The assay method was completed according to the following:

| | |
|---|---|
| Source | Human recombinant HEK-293 cells |
| Substrate | 700 µM acetylthiocholine |
| Vehicle | 1% DMSO |
| Pre-Incubation Time/Temp. | 15 minutes at 25° C. |
| Incubation Time/Temp. | 20 minutes at 25° C. |
| Incubation Buffer | 0.1 M sodium phosphate, pH 7.4 |
| Quantitation Method | Spectrophotometric quantitation of thiocholine |
| Significance Criteria | ≧50% of max stimulation or inhibition |

The assay results are summarized below:

| # | Compound | Mechanism/indication | AChEI (%) 10 µM | AChEI (%) 1 µM | BuChEI (%) 10 µM | BuChEI (%) 1 µM |
|---|---|---|---|---|---|---|
| 1 | S-rivastigmine | ChEI/memory | 19 | | 100 | 45 |
| 32 | [structure] | | 99 | 93 | 42 | |
| 2 | S-rivastigmine-tranylcypromine | MAO-B inh/Parkinson's | 97 | 84 | 67 | 23 |
| 3 | S-rivastigmine-amoxapine | NE reuptake/depression | 16 | | 6 | |
| 4 | S-rivastigmine-desipramine | NE reuptake/depression | 99 | 91 | 60 | 16 |
| 5 | S-rivastigmine-nortriptyline | NE reuptake/depression | 99 | 81 | 55 | 24 |
| 6 | S-rivastigmine-protriptyline | NE reuptake/depression | 99 | 81 | 53 | 16 |
| 7 | S-rivastigmine-fluoxetine | SSRI/depression | 76 | 11 | 15 | |
| 8 | S-rivastigmine-fluvoxamine | SSRI/depression | 76 | 17 | 6 | |
| 9 | S-rivastigmine-paroxetine | SSRI/depression | 69 | 9 | 4 | |
| 10 | S-rivastigmine-duloxetine | Dual reuptake/depression | 100 | 88 | 36 | |
| 11 | S-rivastigmine-betahistine | Histamine/Meniere's | 47 | | 100 | 45 |
| 12 | S-rivastigmine-amlodipine | Ca channel/hypertension | 79 | 20 | 6 | |
| 13 | S-rivastigmine-propylhexedrine | Adrenergic/decongestant | 99 | 62 | 100 | 37 |
| 14 | S-rivastigmine-rimantadine | Antiviral/influenza | 77 | 28 | 13 | |
| 15 | S-rivastigmine-desloratidine | Antihistamine/allergy | 36 | | 6 | |

Example 7

Measurement of Hypothermia and Determination of the Dose Range and Time Course for Cholinergic Effects The induction of hypothermia was determined for compounds of the invention according to the methods described in Freedman, et al., *European Journal of Pharmacology*, 187 (1990), 193-199, which is incorporated by reference herein. Male BKTO mice (20-30g) were housed individually in perspex cages at anbient temperature for at least 60 min prior to experiment. Mice were restrained for up to 1 min every 20 min in a Perspex restraining cage and rectal temperature determined with a thermometer e.g., Jenway 200 or Sensotek BAT-12. Measurement of temperature was estimated using either a rounded 2.5 mm diameter probe inserted 2.4 cm into the rectum or a rounded 1.5 mm probe inserted 1.6 cm into the rectum. In both cases the probe insertion was lubricated with liquid parafilm. Mice were treated with a low dose of the compound of the invention. Test substances were administered by the i.p. route over a range typically of 0.0001-1.0 mg/kg.

The dose range and time course for cholinergic effects of the compounds of the invention was determined as described below.

Subjects: Two hundred eight male CD IGS (Sprague Dawley derived) rats were received at 126-150 grams and maintained four per cage on a regular light/dark cycle (lights on 0600-1800) with ad libitum food and water for about 1 week before commencement of experimentation.

Apparatus: Injection was done with a 25-gauge ⅝-inch needle on a 1-mL tuberculin syringe. Observation was done in a 5½-×10-inch polycarbonate rat housing cage. Temperature was taken with a rat rectal probe on a Model BAT-12 electronic thermometer.

Compound Preparation: Test compounds were dissolved for example, in 0.9% saline. Concentrations for lower doses were prepared by taking aliquots from higher concentrations and diluting. Injection volumes were 1 mL/kg, if the test compound was sufficiently soluble. If less soluble, maximum injection volume were 5 mL/kg. Route of administration was s.c.

As sample protocol is as follows:
Treatment Groups included (N=3, with 6 for Saline)
 Saline
 [(S)-Rivastigmine] at 1, 3, 10, 30, and 100 mg/kg
 (R)-Rivastigmine at 1, 3, 10, 30, and 100 mg/kg
 Test Compounds
 Test Compounds were dosed at 1, 3, 10, 30, and 100 mg/kg
Procedure: The rats were brought to the test room in the home cage. Baseline temperature were be taken just before injection. After injection s.c., the rat was placed in the observation cage. At 0.5, 1, 2, and 4 hours after injection, it was observed briefly for gross signs; salivation was scored as absent, clearly present, or copious; and rectal temperature was taken. In observation for gross signs, special attention was paid to fasciculation (muscle twitch), tremor/ataxia, and abnormal gait. (NB: The experiment has been designed to allow assessment of one rat per time point per minute. Salivation score and temperature were determined within this constraint, but only the most salient of gross signs were noted. After the 4-hour observation point, or sooner if signs of distress were observed, the rat was euthanized by $CO_2$ inhalation.

Data Analysis: Gross signs, salivation score, and temperature at each time point were tabulated for inspection. This is a combination of within-subject design for control and between-subjects design for dose effect. That is, the effect of the compound was measured against the reading taken immediately before injection, and the difference between doses of the compound was measured between groups of three rats. As a precaution against the possibility of large effects caused by repeatedly measuring rectal temperature, a vehicle group (N=6) was included in the pilot with (s)-rivastigmine.

Results of the hypothermia and dose determination are shown below.

| Cmpd # | Name | Compound Structure | Hypothermia MED (mg/kg) | Max Tolerated Dose | TI MTD/MED |
|---|---|---|---|---|---|
| 1 | S-rivastigmine | 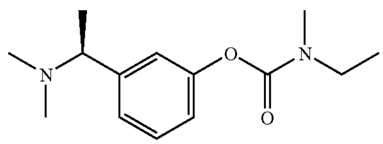 | ≦0.1 | 10 | ≧100 |
| 3 | S-riva-amoxapine | 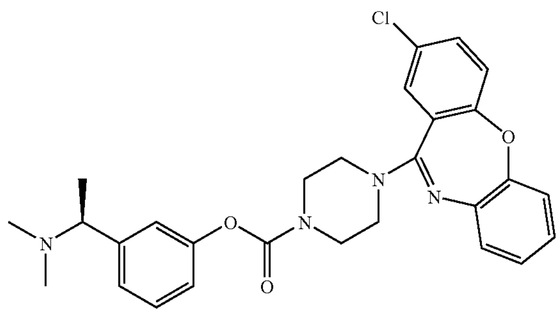 | 10 | ≧100 | ≧10 |
| 4 | S-riva-desipramine | 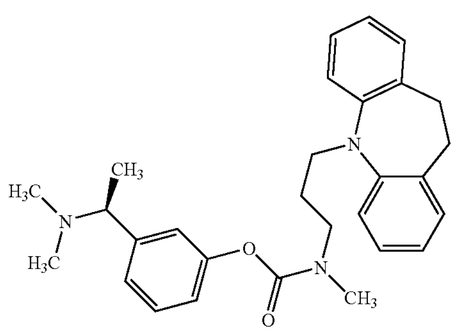 | 3 | ≧100 | ≧30 |
| 5 | S-riva-nortriptyline | 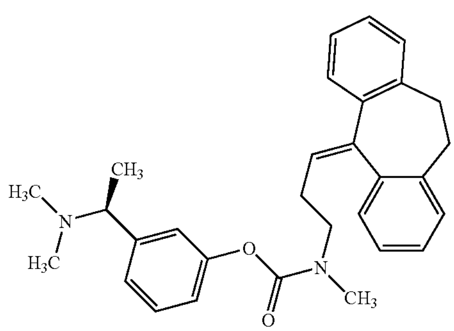 | ≦1 | ≧100 | ≧100 |

-continued

| Cmpd # | Name | Compound Structure | Hypothermia MED (mg/kg) | Max Tolerated Dose | TI MTD/MED |
|---|---|---|---|---|---|
| 6 | S-riva-protriptyline | 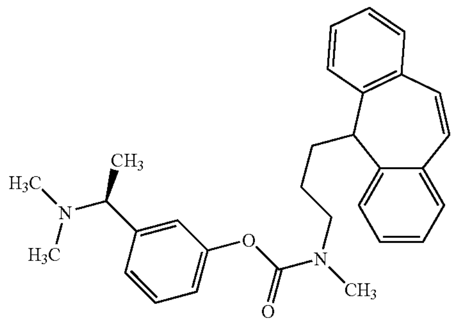 | 100 | >100 | >1 |
| 2 | S-riva-tranylcypromine | 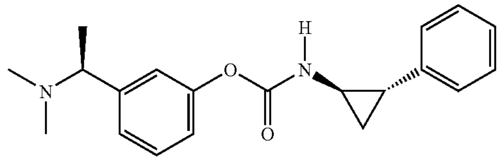 | 10 | 30 | 3 |
| 7 | S-riva-fluoxetine | 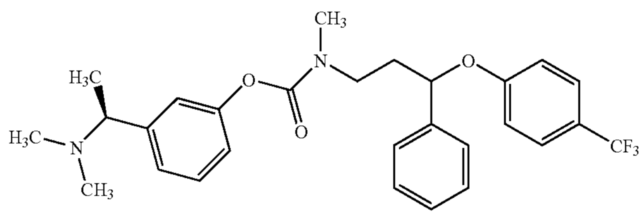 | 3 | ≧100 | ≧30 |
| 11 | S-riva-betahistine | 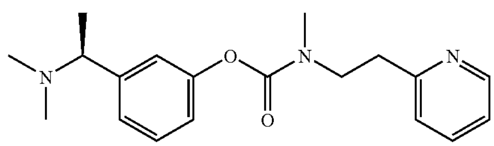 | <1 | 30 | ≧30 |
| 13 | S-riva-propylhexedrine | 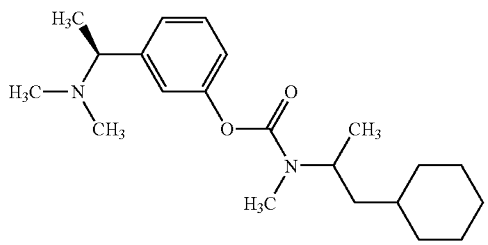 | 10 | ≧100 | ≧10 |
| 15 | S-riva-desloratidine | 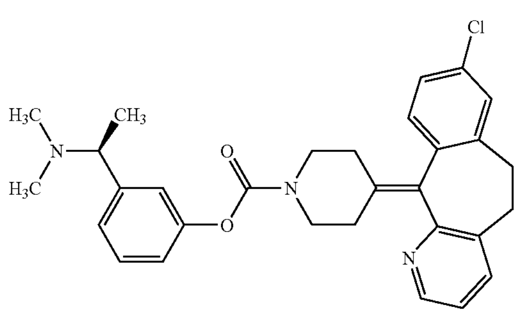 | 3 | ≧100 | >30 |

EQUIVALENTS

While this invention has been particularly shown and described with references to preferred embodiments thereof, it will be understood by those skilled in the art that various changes in form and details may be made therein without departing from the scope of the invention.

The invention claimed is:

1. A compound according to formula I:

(I)

pharmaceutically acceptable salt wherein
Q is selected from:

(V), (P), (Q'), (U), (X), (R), (S), (Z), (AA), (BB)

-continued (Y)
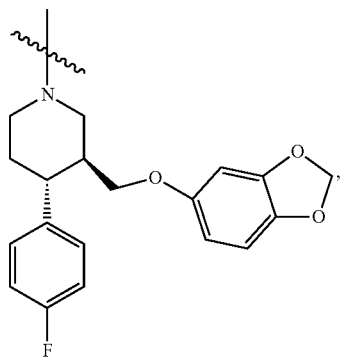

(CC)
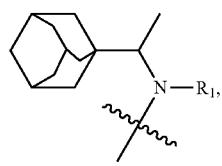

(DD)
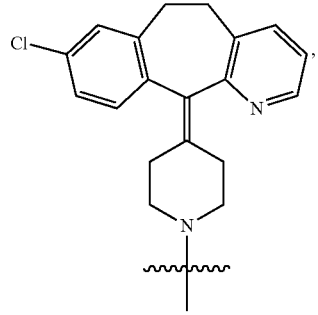

(T)
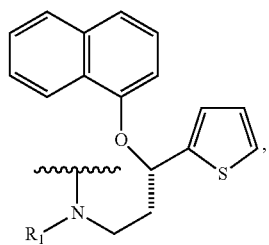

(SSS)
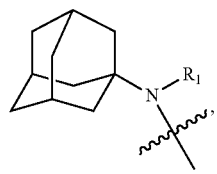

(TTT)
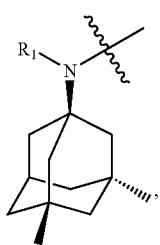

-continued (MM)
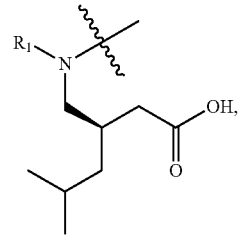

(UU)
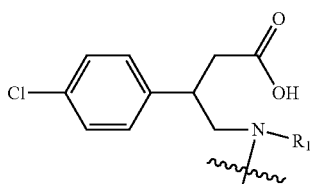

(XX)
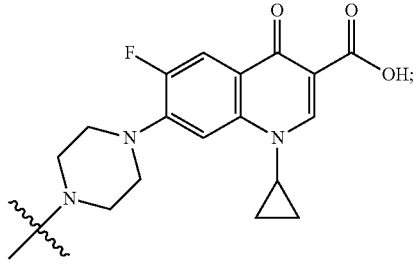
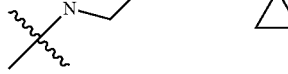

$R_1$ is selected from hydrogen and unsubstituted alkyl, or $R_1$ is absent;

$R_3$, $R_4$ and $R_5$ are each, independently selected from unsubstituted alkyl and hydrogen.

2. The compound according to claim 1, wherein at least one of $R_3$, $R_4$, and $R_5$ is unsubstituted alkyl.

3. The compound according to claim 1, wherein $R_1$ is absent.

4. The compound according to claim 1, wherein $R_1$ is selected from hydrogen, substituted and unsubstituted alkyl.

5. A compound selected from compounds:

(2)
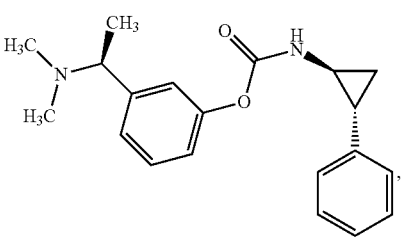

(3)
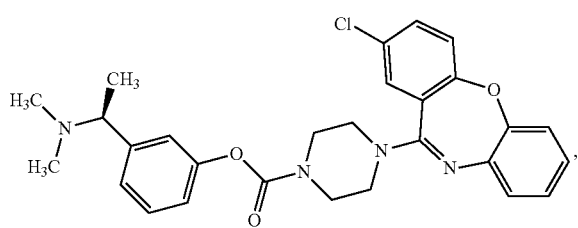

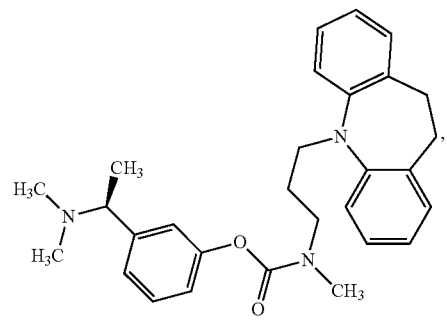
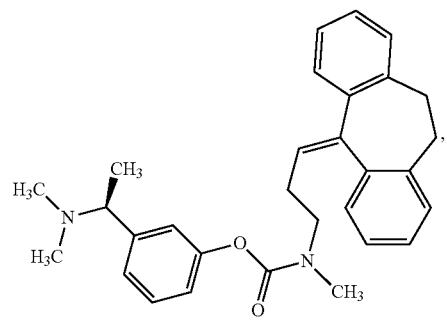
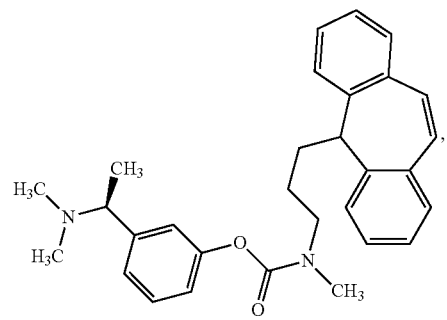
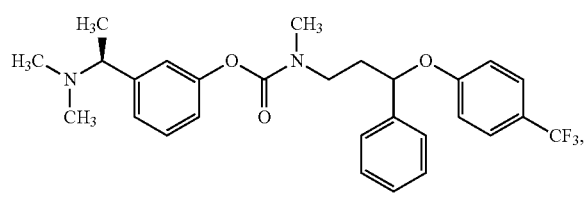
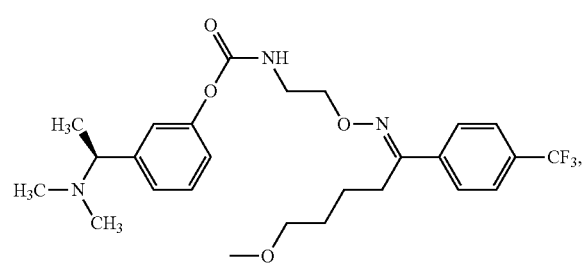

273
-continued
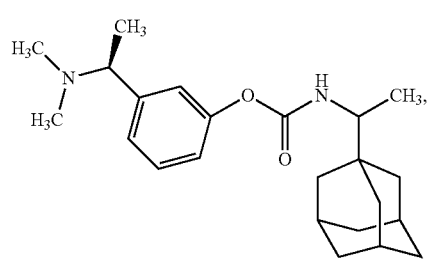
(14)
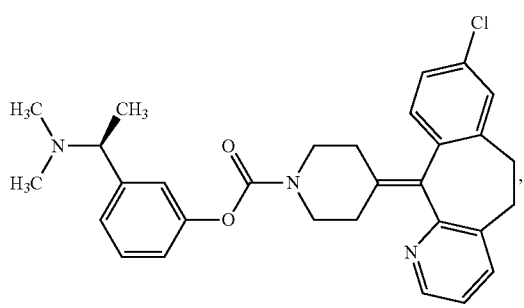
(15)
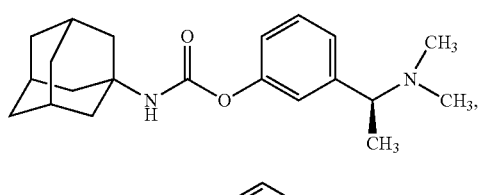
(16)
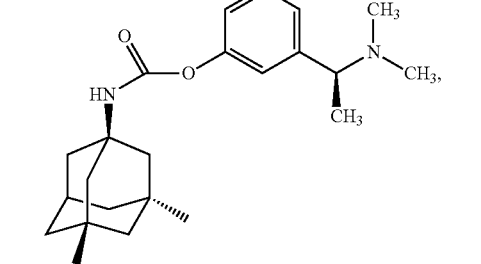
(17)
274
-continued
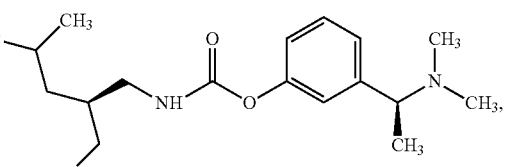
(18)
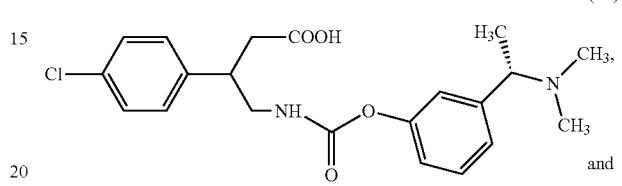
(19)
and
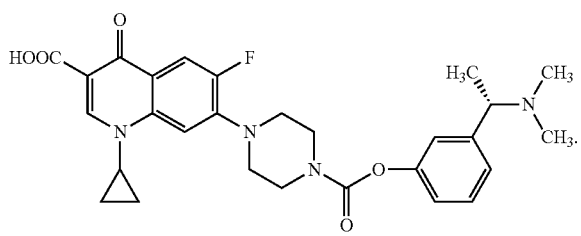
(20)
6. A pharmaceutical composition comprising the compound according to claim 1 or a pharmaceutically acceptable salt thereof.
\* \* \* \* \*